US005869312A

United States Patent [19]
Cochran et al.

[11] Patent Number: 5,869,312
[45] Date of Patent: *Feb. 9, 1999

[54] RECOMBINANT SWINEPOX VIRUS

[75] Inventors: Mark D. Cochran, Carlsbad; David E. Junker, San Diego, both of Calif.

[73] Assignee: Syntro Corporation, Lenexa, Kans.

[ * ] Notice: The term of this patent shall not extend beyond the expiration date of Pat. No. 5,382,425.

[21] Appl. No.: 97,554

[22] Filed: Jul. 22, 1993

Related U.S. Application Data

[63] Continuation-in-part of Ser. No. 820,154, Jan. 13, 1992, Pat. No. 5,382,425.

[30] Foreign Application Priority Data

Jan. 13, 1993 [WO] WIPO ............... PCT/US93/00324

[51] Int. Cl.$^6$ .................................................. C12N 07/01
[52] U.S. Cl. ..................................... 435/235.1; 435/320.1
[58] Field of Search ...................... 435/235.1; 424/199.1, 424/229.1, 232.1

[56] References Cited

U.S. PATENT DOCUMENTS

| | | | |
|---|---|---|---|
| 5,338,683 | 8/1994 | Paoletti | 435/320.1 |
| 5,382,425 | 1/1995 | Cochran et al. | 435/69.1 |

FOREIGN PATENT DOCUMENTS

| | | | |
|---|---|---|---|
| 0261940 | 3/1988 | European Pat. Off. | C12N 15/00 |
| 0284416 | 9/1988 | European Pat. Off. | C12N 15/00 |
| WO8903429 | 4/1989 | WIPO | C12P 21/00 |
| WO8912684 | 12/1989 | WIPO | C12N 15/00 |

OTHER PUBLICATIONS

Davison, A.J. et al. 1989a. J. Mol. Biol. vol. 210 pp.749–769.

Davison, A.J. et al. 1989b. J. Mol. Biol. vol. 210 pp. 771–784.

R.A. Bhat, et al. (1989), "Efficient Expression of Small RNA Polymerase III Genses From a Noval Simina 40 Vector and Their Effect on Viral Gene Expression", Nucleic Acids Research 17: 1159–1176.

J.J. Esposito, et al. (1988), "Successful Oral Rabies Vaccination of Raccoons with Raccoon Poxvirus Recombinats Expressing Rabies Virus Glycprotein", Virology 165: 313–316.

S. Joshi, et al. (1991), "Inhibition of Human Immunodeficiency Virus Type 1 Multiplication by Antisense and Sense RNA Expession", Journal of Virology; 65: 5524–5530.

C. Flexner, et al. (1990), "Attenuation and Immunogenicity in Primates of Vaccinia Virus Recombinats Expressing Human Interleukin–2", Vaccines 8: 17–21.

L. Kasza (1981) Diseases of Swine, 254–260, Ed. A.D. Leman, et al., The Iowa State University Press.

R.F. Massung and R.W. Moyer, (1991) "The Molecular Biology of Swinepox Virus; A Caharacterization of the Viral DNA", Virology 180: 347–354.

R.F. Massung and R.W. Moyer, (1991) "The Molecular Biology of Swinepox Virus; The Infectious Cycle", Virology 180: 355–365.

J. Taylor, et al. (1991) "Efficacy Studies on a Canarypox–rabies Recombinant Virus", Vaccine 9:190–193.

W.M. Schnitzlein and D.N. Tripathy (1991), "Identification and Nucleotide Sequence of the Thymidine Kinase Gene of Swinepox Virus", Virology 181: 727–732.

(List continued on next page.)

*Primary Examiner*—Mary E. Mosher
*Attorney, Agent, or Firm*—John P. White; Cooper & Dunham LLP

[57] ABSTRACT

The present invention relates to a recombinant swinepox virus capable of replication comprising foreign DNA inserted into a site in the swinepox viral DNA which is not essential for replication of the swinepox virus. The invention further relates to homology vectors which produce recombinant swinepox viruses by inserting foreign DNA into swinepox viral DNA.

4 Claims, 44 Drawing Sheets

OTHER PUBLICATIONS

M. Wachsman, et al. (1989) "Antigen–presenting Capacity of Epidermal Cells Infected with Vaccinia Virus Recombinants Containing the Herpes Simplex Virus Glcoprotein D, and Protective Immunity", Journal of General Virology 70: 2513–2520.

P.P Williams, et al. (1989) "Immunologival Responses of Cross–bred and In–bred Miniature Pigs to Swine Poxvirus", Veterinary Immunology and Immunopathology 23: 149–159.

J.A. Feller, et al. (1991) "Isolation and Molecular Characterization of the Swinepox Virus Thymidine Kinase Gene", Virology 183: 578–585.

M. Riviere, et al. (1992) "Protection of Mice and Swine from Pseudorabies Virus Conferred by Vaccinia Virus–Based Recombinants", Journal of Virology 66:3423–3434 (Exhibit 1).

R.F. Massung, et al. (1993) "DNA Sequence Analysis of Conserved and Unique Regions of Swinepox Virus: Identification of Genetic Elements Supporting Phenotypic Observations Including a Novel G Protein–Coupled Receptor Homologue", Virology 197: 511–528 (Exhibit 2).

T. Tuboly, et al. (1993) "Potential Viral Vectors For the Stimulation of Mucosal Antibody Responses Against Enteric Viral Antigens in Pigs", Research in Veterinary Science 54: 345–350 (Exhibit 3).

P.L. Foley, et al. (1991) "Swinepox Virus as a Vector for the Delivery of Immunogens", Annals New York Academy of Sciences 646: 220–222 (Exhibit 4).

M.L. van der Leek, et al. (1994) "Evaluation of Swinepox Virus as a Vaccine Vector in Pigs Using an Aujeszky's (Pseudorabies) Virus Gene Insert Coding For Glycoproteins gp50 and gp63", The Veterinary Record 134: 13–18 (Exhibit 5).

FIG. 2A

```
AATGTATCCAGAGTTGTTGAATGCCTTATCGTACCTAATATTAATATAGAGTTATTAACT
GAATAAGTATATATAAATGATTGTTTTATAATGTTTGTTATCGCATTTAGTTTTGCTGT
ATGGTTATCATATACATTTTAAGGCCGTATATGATAAATGAAAATATATAAGCACTTAT
TTTTGTTAGTATAATAACACAATGCCGTCGTATATGTATCCGAAGAACGCAAGAAAGTA
                     MetProSer..........
ATTTCAAAGATTATATCATTACAACTTGATGATTATAAAAACTTCCTAAAAATATATAAT
ACCATGTTAGAATTTGGTCTACATGGAAATCTACCAGCTTGTATGTATAAAGATGCCGTA
TCATATGATATAATAAATAAGATTTTTACCTTATATTGTGTTATGTTAAAGATTTA
ATAAATGTTATAAAATCATCATCTGTAATAGATACTAGATTACATCAATCTGTATTAAAA
CATCGTAGAGCGTTAATAGATACGGCGATCAAGACATTATCACTTTAATGATCATTAAT
AAGTTACTATCGATAGATGATATATCCTATATATTAGATAAAAAAATAATTCATGTAAC
                               ..........IleHisVal
```

FIG. 2B

```
GAGATATTAAATCATGTAAATGCTCGATATGTTCCGACTCTATAACACATCATATATATG
AspIleLysSer..........
AACAACATCATGTAGATATTTAATGCATGGATGACATCCTAATCTTATAGATGTATTGTTCA
ATCTAACTAGATATTTAATGCATGGATGACATCCTAATCTTATAAGCGTAAAAGGAT
GGGTCCCCTTATTGGATTATTAACGGGTGATATAGGTATTATTAAAACTATATTCCA
CCATGAATATAAATGGGCTACGGTATGGAGAGTATTACGTTATCTTCATACGATATGAGTA
ATAAATTAGTCTCTATTATTAATACACCCATATGAGTAATAACCGTTACTACATGTT
GTTCACTCATTCAATGAATATTATTCAAAAATTGTGATTTAATAAATGTTATTTTAGAATATA
TGATATCTTATTATTATATAGAATACTGTACTAGAATCATCAGGCATATATTTTGTCAGATGC
TTATTTCAAAAGTCGTAAAATCGTAATAATACTGTACTAGAATCATCAGGCATATATTTTGTCAGATGC
GTGTACAGACAAATTGAATTGGAAATAGATGAGCTCATTATTAATGGATCTATGCCTG
TACAGCTTATGCATTTACTTCTAAAGGTAGCTACCATAATATATTAGAGAGAAATCAAAGAAA
                     .....LysGluI
le----
ACCTTGTCTAATTGTATCTTGTATTTTGGATCTGATCGAAGATTATTAAATAATCGTATG
AAAAGTAGTAGATAGTTTATATCGTTACTGGACATGATATTATGTTTAGTTAATTCT
TCTTTGGCATGAATTCTACACGTCGGANAAGGTAATGTATCTATAATGGTATAAAGCTT
```

FIG. 3B

```
                           10         20         30         40         50         60         70
                            *          *          *          *          *          *          *
(A) VV          MFMYPEFARKALSKLISKKLNIEKVSSKHQLVLLDYGLHGLLPKSLYLEAINSDILNVRFFPPEIINVT
    orf 01L     :: ::: :: :     :  ::  ::      ::      :: :: : :: :  : ::  ::: :   ::
(B) SPV         MPSYMYPKNARKVISKIISLQLDIKKLPKKYINTMLEFGLHGNLPACMYKDAVSYDINNIRFLPYNCVMVK
    AccI-ClaI                                                 AccI 80         90         100        110        120
                            *          *           *          *          *
                DIVKALQNSCRVDEYLKAVSLYHKNSLMVSGPNVVK-LMIEYNLLTHSDLEWLINENVVKA
                :  :      ::   ::       :: :   ::  :  ::  ::   :::: : : :
                DLINVIKSSSVIDTRLHQSVLKHRRALIDYGDQDIITLMIINKLLSIDDISYILDKKIIHV
                                                                    ClaI 570        580        590        600        610
                    *          *          *          *          *
(C) VV orf 01L  VLNDQYAKIVIFFNTIIEYIIATIYYRLTVLNNYTNVKHFVSKVLHTVMEA
                ::::: :::::: : ::  :: : ::  : :: :::: :: :::: ::
(D) SPV         SLNEYYSKIVILINVILEYMISIILYRILIVKRFNNIKEFISKVVNTVLES
    EcoRV-EcoRI             EcoRV 620        630        640        650        660
                    *          *          *          *          *
                CGVLFSYIKVNDKIEHELEEMVDKGTVPSYLYHLSINVISISIILDDINGTR-    TERM
                : :: :::  :  :: :: ::::          : :  ::   :     :
                SGIYFCQMRVHEQIELELIDELIINGSMPVQLMHLLLKVATIILEEIKEI-  → EcoRI
                                                                       TERM
```

| DNA | Origin | Sites | Size |
|---|---|---|---|
| Vector | pSP64 | HindIII - BamHI | ~2972 BP |
| Fragment 1 | SPV HindIII M | HindIII- AccI | ~2156 BP |
| Fragment 2 | pJF751 | BamHI - PvuII | ~3010 BP |
| Fragment 3 | SPV HindIII M | AccI - BglII | ~1146 BP |

| DNA | Origin | Sites | Size |
|---|---|---|---|
| Vector | pSP64 | HindIII - BamHI | ~2972 BP |
| Fragment 1 | SPV HindIII M | HindIII - AccI | ~2156 BP |
| Fragment 2 | pJF751 | BamHI - PvuII | ~3002 BP |
| Fragment 3 | PRV BamHI #7 | EcoRI* - StuI | ~1558 BP |
| Fragment 4 | SPV HindIII | AccI - BglII | ~1146 BP |

\* introduced via PCR cloning

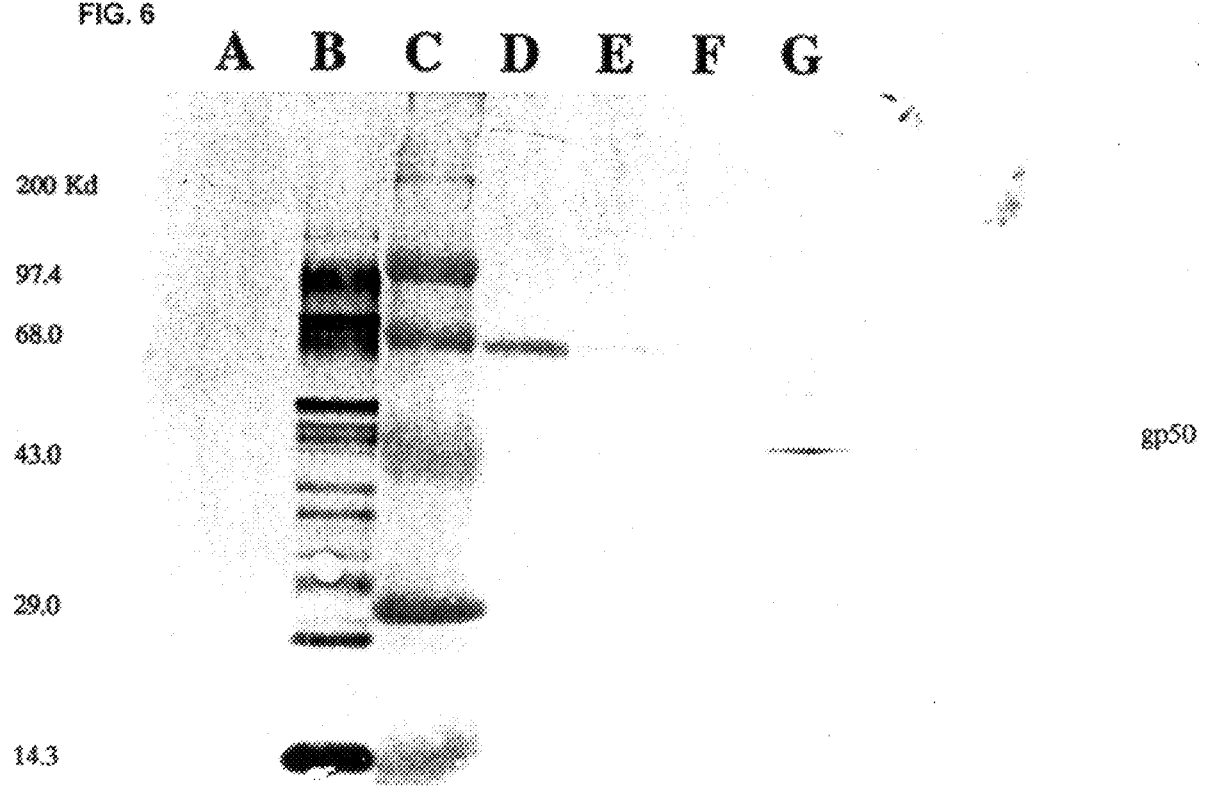

FIG. 7

```
ACGGGTAGAACGGTAAGAGAGGCCGCCCCTCAATTGCGAGCCAGACTTCACAACCTCCGT
                                        AvaII
                                        ┌─/──┐
TCTACCGCTTCACCGACAACAGTCCTCAATCATGGACCGCGCCGTTAGCCAAGTTGCGTT
                              MetAspArg............
AGAGAATGATGAAAGAGAGGCAAAAAATACATGGCGCTTGATATTCCGGATTGCAATCTT
ATTCTTAACAGTAGTGACCTTGGCTATATCTGTAGCCTCCCTTTTATATAGCATGGGGGC
TAGCACACCTAGCGATCTTGTAGGCATACCGACTAGGATTTCCAGGGCAGAAGAAAAGAT
TACATCTACACTTGGTTCCAATCAAGATGTAGTAGATAGGATATATAAGCAAGTGGCCCT
TGAGTCTCCATTGGCATTGTTAAATACTGAGACCACAATTATGAACGCAATAACATCTCT
CTCTTATCAGATTAATGGAGCTGCAAACAACAGCGGGTGGGGGCACCTATTCATGACCC
AGATTATATAGGGGGGATAGGCAAAGAACTCATTGTAGATGATGCTAGTGATGTCACATC
ATTCTATCCCTCTGCATTTCAAGAACATCTGAATTTTATCCCGGCGCCTACTACAGGATC
AGGTTGCACTCGAATACCCTCATTTGACATGAGTGCTACCCATTACTGCTACACCCATAA
TGTAATATTGTCTGGATGCAGAGATCACTCACACTCACATCAGTATTTAGCACTTGGTGT
GCTCCGGACATCTGCAACAGGGAGGGTATTCTTTTCTACTCTGCGTTCCATCAACCTGGA
CGACACCCAAAATCGGAAGTCTTGCAGTGTGAGTGCAACTCCCCTGGGTTGTGATATGCT
GTGCTCGAAAGCCACGGAGACAGAGGAAGAAGATTATAACTCAGCTGTCCCTACGCGGAT
GGTACATGGGAGGTTAGGGTTCGACGGCCAATATCACGAAAAGGACCTAGATGTCACAAC
ATTATTCGGGGACTGGGTGGCCAACTACCCAGGAGTAGGGGGTGGATCTTTTATTGACAG
CCGCGTGTGGTTCTCAGTCTACGGAGGGTTAAAACCCAATACACCCAGTGACACTGTACA
GGAAGGGAAATATGTGATATACAAGCGATACAATGACACATGCCCAGATGAGCAAGACTA
CCAGATTCGAATGGCCAAGTCTTCGTATAAGCCTGGACGGTTTGGTGGGAAACGCATACA
GCAGGCTATCTTATCTATCAAAGTGTCAACATCCTTAGGCGAAGACCCGGTACTGACTGT
ACCGCCCAACACAGTCACACTCATGGGGGCCGAAGGCAGAATTCTCACAGTAGGGACATC
CCATTTCTTGTATCAGCGAGGGTCATCATACTTCTCTCCCGCGTTATTATATCCTATGAC
AGTCAGCAACAAAACAGCCACTCTTCATAGTCCTTATACATTCAATGCCTTCACTCGGCC
AGGTAGTATCCCTTGCCAGGCTTCAGCAAGATGCCCCAACTCATGTGTTACTGGAGTCTA
TACAGATCCATATCCCCTAATCTTCTATAGAAACCACACCTTGCGAGGGGTATTCGGGAC
AATGCTTGATGGTAACAAGCAAGACTTAACCCTGCGTCTGCAGTATTCGATAGCACATC
CCGCAGTCGCATAACTCGAGTGAGTTCAAGCAGCATCAAAGCAGCATACACAACATCAAC
TTGTTTTAAAGTGGTCAAGACCAATAAGACCTATTGTCTCAGCATTGCTGAAATATCTAA
TACTCTCTTCGGAGAATTCAGAATCGTCCCGTTACTAGTTGAGATCCTCAAAGATGACGG
GGTTAGAGAAGCCAGGTCTGGCTAGTTGAGTCAACTATGAAAGAGTTGGAAAGATGGCAT
............ArgSerGly---
                                                        NaeI
                                                      ┌──/─┐
TGTATCACCTATCTTCTGCGACATCAAGAATCAAACCGAATGCCGGC
```

| DNA | Origin | Sites | Size |
| --- | --- | --- | --- |
| Vector | pSP64 | Bam HI—Hind III | ~2972 BP |
| Fragment 1 | SPV HindIII G | Hind III—Nde I | ~ 670 BP |
| Fragment 2 | pJF751 | Bam HI—Pvu II | ~3010 BP |
| Fragment 3 | SPV HindIII G | Nde I—Bam HI | ~1069 BP |

FIG. 9C

JUNCTION C

```
         Pvu II
GAA ATC ⌐CAG CTG┐ AGC GCC GGT CGC TAC CAT TAC CAG TTG GTC TGG TGT CAA AAA GAT
Glu Ile  Gln Leu  Ser Ala Gly Arg Tyr His Tyr Gln Leu Val Trp Cys Gln Lys Asp
         ↓                                                        E. coli Lac Z (1024) →
         pJF 751
```

JUNCTION C
(CONT.)

```
CCA TAA TTA ATT AAC
Pro *
```

JUNCTION C
(CONT.)

```
          [Nde I]
CCG GGT CGA CCT ATG AAC GTA AAC CAT TTG GTA ATA TTC TTA ATC TTA TAC CAT TAT CGG
                    ↑
                   SPV TK
```

JUNCTION D

```
          Bam HI                              Sac I  EcoR I
TCT ACT ATT GTA TAT ATA GGA TCC CCG GGC GAG CTC GAA TTC GTA ATC ATG GTC ATA GCT GTT TCC
                ↓                             ←    pSP64    →
              SPV Hind III G
```

| DNA | Origin | Sites | Size |
|---|---|---|---|
| Vector | pSP64 | Hind III—Bam HI | ~2972 BP |
| Fragment 1 | SPV HindIII M | Bgl II—Acc I | ~1146 BP |
| Fragment 2 | pJF751 | Bam HI—Pvu II | ~3002 BP |
| Fragment 3 | PRV BamHI 2 & 9 | Nco I—Nco I | ~2378 BP |
| Fragment 4 | SPV HindIII M | Acc I—Hind III | ~2156 BP |

FIG. 10D

JUNCTION D

```
     [Nco I]
   C CAT GCT CTA GAG GAT CCC CGG GCG AGC TCG AAT TCG GAT CCA TAA TTA ATT
         →                                           EcoRI
         PRV Bam HI #9
```

JUNCTION D (CONT.)

```
   AAT TAA TTT TTA TCC CGG GTC GAC CGG GTC GAC CTG CAG CCT ACA TGG AAA TCT ACC
                                                        [Acc I]      →
                        ←                                            SPV Hind III M
                        SPV Hind III M
```

JUNCTION E

```
                                             HindIII
   TAA TGT ATC TAT AAT GGT ATA AAG CTT GTA TTC TAT AGT GTC ACC TAA ATC
                                         →
                                         pSP64
```

| DNA | Origin | Sites | Size |
|---|---|---|---|
| Vector | pSP64 | Hind III—Bam HI | ~2972 BP |
| Fragment 1 | SPV HindIII M | Bgl II—Acc I | ~1146 BP |
| Fragment 2 | pJF751 | Bam HI—Pvu II | ~3002 BP |
| Fragment 3 | PRV BamHI 2 & 9 | Nco I—Nco I | ~2378 BP |
| Fragment 4 | SPV HindIII M | Acc I—Hind III | ~2156 BP |

FIG. 11B

JUNCTION A

ACA GGA AAC AGC TAT GAC CAT GAT TAC GAA TTC GAG CTC GCC CGG GGA TCT [Bam HI/Bgl II]

→ SPV Hind III M

← pSP64

JUNCTION B

AA ATA TAT AAA TAC CAT GTT AGA ATT TGG TCT GCT GCA GGT CGA CTC TAG AAT TTC ATT TTG
[Acc I]

← SPV Hind III M

LP1 →

JUNCTION B (CONT.)

TTT TTT TCT ATG CTA TAA ATG AAT TCG GAT CCC GTC GTT TTA
                              MET Asn Ser Asp Pro Val Val Leu
                              EcoRI  BamHI

LP1 →

← pJF 751

E. coli Lac Z (10) →

FIG. 11D
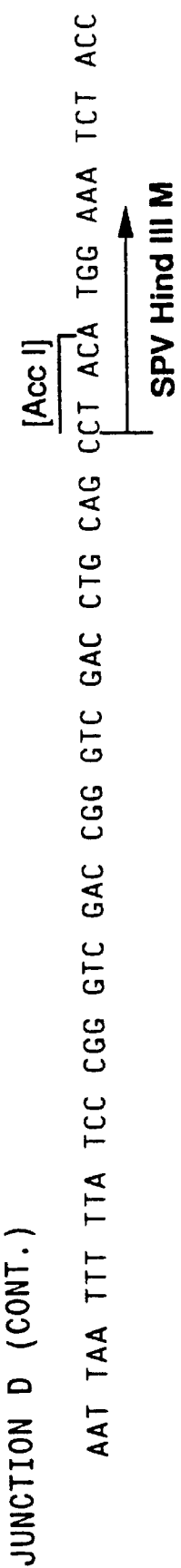
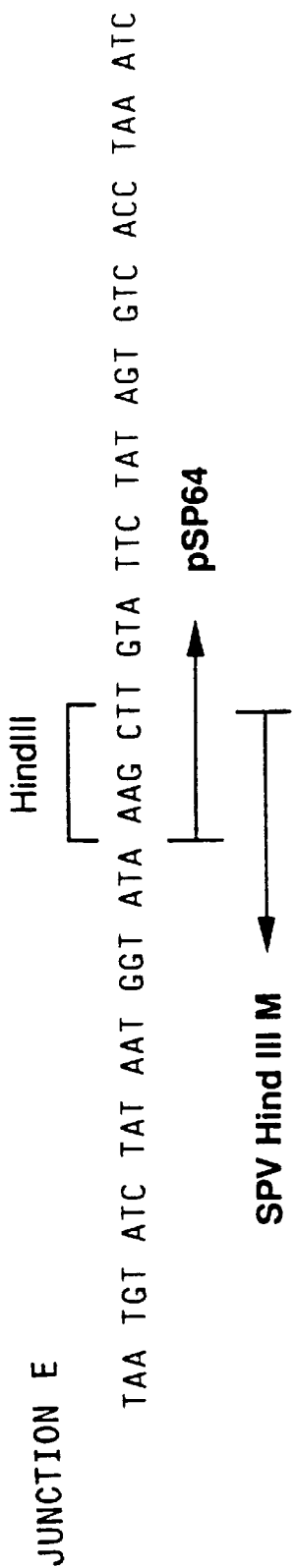

FIG. 12D

JUNCTION D

```
     [Nco I]
   C CAT GCT CTA GAG GAT CCC CGG GCG AGC TCG AAT TCG GAT CCA TAA TTA ATT
                                                      └─────┘
         PRV Bam HI #9 →                                EcoRI
```

JUNCTION D (CONT.)

```
                                                                [Acc I]
   AAT TAA TTT TTA TCC CGG GTC GAC CGG GTC GAC CTG CAG CCT ACA TGG AAA TCT ACC
                                                                        SPV Hind III M →
```

JUNCTION E

```
                                        HindIII
                                        ┌─────┐
   TAA TGT ATC TAT AAT GGT ATA AAG CTT GTA TTC TAT AGT GTC ACC TAA ATC
                                   ← pSP64
   ← SPV Hind III M
```

| DNA | Origin | Sites | Size |
|---|---|---|---|
| Vector | pSP64 | Hind III–Bam HI | ~2972 BP |
| Fragment 1 | SPV HindIII M | Bgl II–Acc I | ~1146 BP |
| Fragment 2 | ILT Asp718I 5.1 kb | Eco RI†–Mbo I | ~939 BP |
| Fragment 3 | pJF751 | Bam HI–Pvu II | ~3002 BP |
| Fragment 4 | SPV HindIII M | Acc I–Hind III | ~2156 BP |

† Restriction site introduced by PCR cloning

FIG. 13D

JUNCTION D

```
        Pvu II
GAA ATC CAG CTG AGC GCC GGT CGC TAC CAT TAC CAG TTG GTC TGG TGT CAA AAA GAT
Glu Ile Gln Leu Ser Ala Gly Arg Tyr His Tyr Gln Leu Val Trp Cys Gln Lys Asp
         pJF 751 →                                              E. coli Lac Z (1024) →
```

JUNCTION D (CONT.)

```
                              Acc I        Pst I
CCA TAA TTA ATT AAC CCG GGT CGA CCT GCA G
Pro  *                                    SPV Hind III M ↑
```

JUNCTION E

```
                                     HindIII
TAA TGT ATC TAT AAT GGT ATA AAG CTT GTA TTC TAT AGT GTC ACC TAA ATC
                                    pSP64 ↑
SPV Hind III M ↓
```

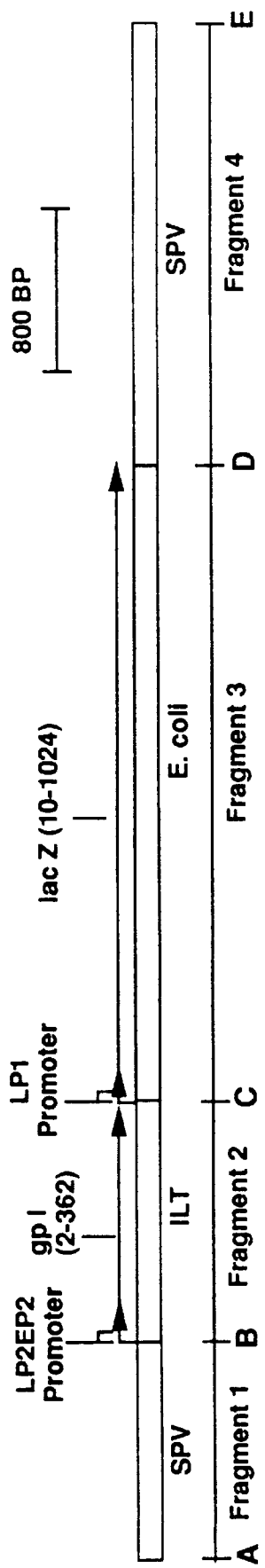

FIG. 14D

JUNCTION D

```
                Pvu II
GAA ATC  CAG CTG  AGC GCC GGT CGC TAC CAT TAC CAG TTG GTC TGG TGT CAA AAA GAT
Glu Ile  Gln Leu  Ser Ala Gly Arg Tyr His Tyr Gln Leu Val Trp Cys Gln Lys Asp
         ──────→                                                ───────────→
         pJF 751                                                E. coli Lac Z (1024)
```

JUNCTION D (CONT.)

```
                    Asc I                     Acc I              Not I
CCA TAA TTA ATT AAC CCG GGT CGA GGC GCG CCG GGT CGA CCT GCA GGC GGC CGC
Pro *                                                                  ──────→
                                                                       SPV Hind III M
```

JUNCTION E

```
                Hind III
TAA TGT ATC TAT AAT GGT ATA AAG CTT GTA TTC TAT AGT GTC ACC TAA ATC
────                    ──────────→
SPV Hind III M          pSP64
```

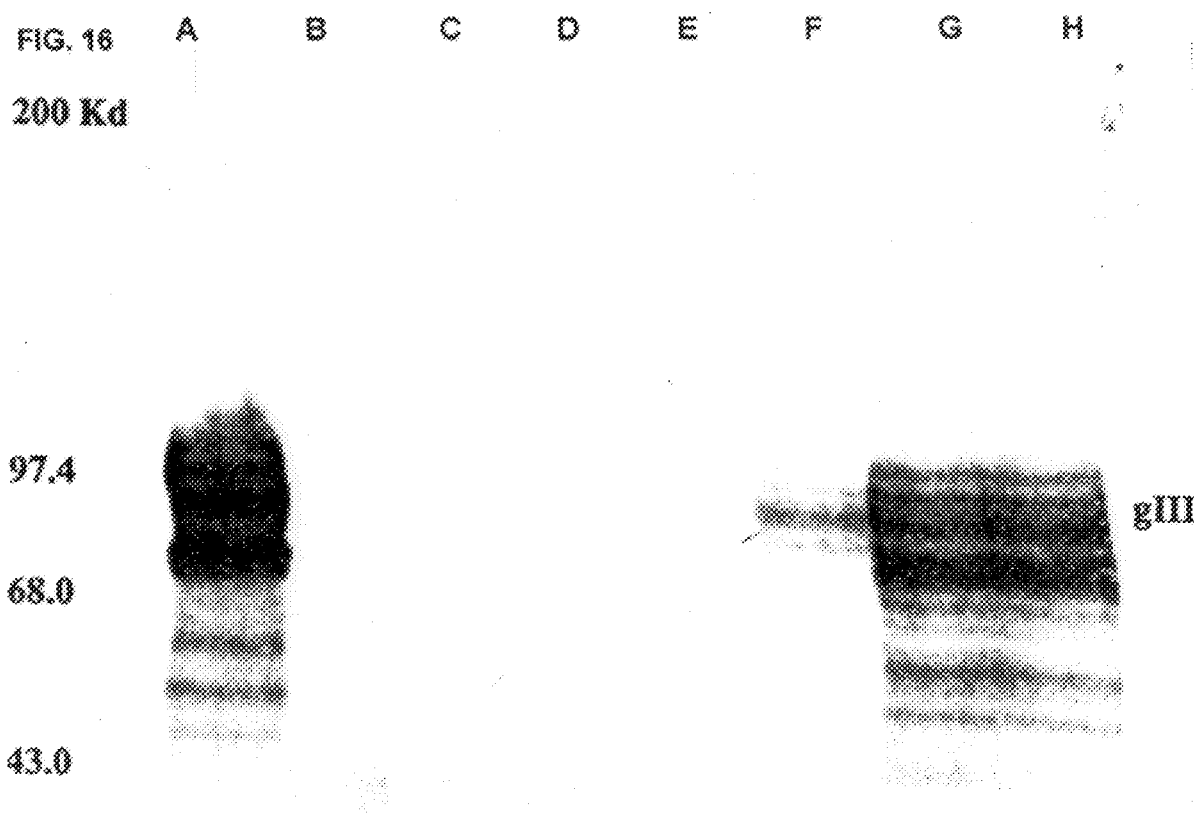

RECOMBINANT SWINEPOX VIRUS

This application is a continuation-in-part of U.S. Ser. No. 07/820,154 filed Jan. 13, 1992, now U.S. Pat. No. 5,382,425, the contents of which are incorporated by reference into the present application. Within this application several publications are referenced by arabic numerals within parentheses. Full citations for these publications may be found at the end of the specification immediately preceding the claims. The disclosures of these publications are hereby incorporated by reference into this application in order to more fully describe the state of the art to which this invention pertains.

BACKGROUND OF THE INVENTION

Swinepox virus (SPV) belongs to the family poxviridae. Viruses belonging to this group are large, double-stranded DNA viruses that characteristically develop in the cytoplasm of the host cell. SPV is the only member of the genus Suipoxvirus. Several features distinguish SPV from other poxviruses. SPV exhibits species specificity (18) compared to other poxviruses such as vaccinia which exhibit a broad host range. SPV infection of tissue culture cell lines also differs dramatically from other poxviruses (24). It has also been demonstrated that SPV does not exhibit antigenic cross-reactivity with vaccinia virus and shows no gross detectable homology at the DNA level with the ortho, lepori, avi or entomopox virus groups (24). Accordingly, what is known and described in the prior art regarding other poxviruses does not pertain a priori to swinepox virus. SPV is only mildly pathogenic, being characterized by a self-limiting infection with lesions detected only in the skin and regional lymph nodes. Although the SPV infection is quite limited, pigs which have recovered from SPV are refractory to challenge with SPV, indicating development of active immunity (18).

The present invention concerns the use of SPV as a vector for the delivery of vaccine antigens and therapeutic agents to swine. The following properties of SPV support this rationale: SPV is only mildly pathogenic in swine, SPV is species specific, and SPV elicits a protective immune response. Accordingly, SPV is an excellent candidate for a viral vector delivery system, having little intrinsic risk which must be balanced against the benefit contributed by the vector's vaccine and therapeutic properties.

The prior art for this invention stems first from the ability to clone and analyze DNA while in bacterial plasmids. The techniques that are available are detailed for the most part in Maniatis et al., 1983 and Sambrook et al., 1989. These publications teach state of the art general recombinant DNA techniques.

Among the poxviruses, five (vaccinia, fowlpox, canarypox, pigeon, and raccoon pox) have been engineered, previous to this disclosure, to contain foreign DNA sequences. Vaccinia virus has been used extensively to vector foreign genes (25) and is the subject of U.S. Pat. Nos. 4,603,112 and 4,722,848. Similarly, fowlpox has been used to vector foreign genes and is the subject of several patent applications EPA 0 284 416, PCT WO 89/03429, and PCT WO 89/12684. Raccoon pox (10) and Canarypox (31) have been utilized to express antigens from the rabies virus. These examples of insertions of foreign genes into poxviruses do not include an example from the genus Suipoxvirus. Thus, they do not teach methods to genetically engineer swinepox viruses, that is, where to make insertions and how to get expression in swinepox virus.

The idea of using live viruses as delivery systems for antigens has a very long history going back to the first live virus vaccines. The antigens delivered were not foreign but were naturally expressed by the live virus in the vaccines. The use of viruses to deliver foreign antigens in the modern sense became obvious with the recombinant vaccinia virus studies. The vaccinia virus was the vector and various antigens from other disease causing viruses were the foreign antigens, and the vaccine was created by genetic engineering. While the concept became obvious with these disclosures, what was not obvious was the answer to a more practical question of what makes the best candidate virus vector. In answering this question, details of the pathogenicity of the virus, its site of replication, the kind of immune response it elicits, the potential it has to express foreign antigens, its suitability for genetic engineering, its probability of being licensed by regulatory agencies, etc, are all factors in the selection. The prior art does not teach these questions of utility.

The prior art relating to the use of poxviruses to deliver therapeutic agents relates to the use of a vaccinia virus to deliver interleukin-2 (12). In this case, although the interleukin-2 had an attenuating effect on the vaccinia vector, the host did not demonstrate any therapeutic benefit.

The therapeutic agent that is delivered by a viral vector of the present invention must be a biological molecule that is a by-product of swinepox virus replication. This limits the therapeutic agent in the first analysis to either DNA, RNA or protein. There are examples of therapeutic agents from each of these classes of compounds in the form of anti-sense DNA, anti-sense RNA (16), ribozymes (34), suppressor tRNAs (2), interferon-inducing double stranded RNA and numerous examples of protein therapeutics, from hormones, e.g., insulin, to lymphokines, e.g., interferons and interleukins, to natural opiates. The discovery of these therapeutic agents and the elucidation of their structure and function does not make obvious the ability to use them in a viral vector delivery system.

SUMMARY OF THE INVENTION

The invention provides a recombinant swinepox virus capable of replication which comprises swinepox viral DNA and foreign DNA encoding RNA which does not naturally occur in an animal into which the recombinant swinepox virus is introduced. The foreign DNA is inserted into the swinepox viral DNA at a site which is not essential for replication of the swinepox virus and is under the control of a promoter.

This invention provides a homology vector for producing a recombinant swinepox virus by inserting foreign DNA into the genomic DNA of a swinepox virus which comprises a double-stranded DNA molecule. This molecule consists essentially of double-stranded foreign DNA encoding RNA which does not naturally occur in an animal into which the recombinant swinepox virus is introduced. At one end of this foreign DNA is double-stranded swinepox viral DNA homologous to genomic DNA located at one side of a site on the genomic DNA which is not essential for replication of the swinepox virus. At the other end of the foreign DNA is double-stranded swinepox viral DNA homologous to genomic DNA located at the other side of the same site on the genomic DNA.

BRIEF DESCRIPTION OF THE FIGURES

FIGS. 2A–2B DNA sequence from homology vector 515-85.1. The sequence of two regions of the homology vector 515-85.1 are shown. The first region (FIG. 2A) (SEQ ID NO:1) covers a 599 base pair sequence which flanks the unique AccI site as indicated in FIGS. 3A–3B. The beginning (Met) and end (Val) of a 115 amino acid ORF is indicated by the translation of amino acids below the DNA sequence. The second region (FIG. 2B) (SEQ ID NO:3) covers the 899 base pairs upstream of the unique HindIII site as indicated in FIGS. 3A–3B. The beginning (Asp) and end (Ile) of a 220 amino acid ORF is indicated by the translation of amino acids below the DNA sequence.

FIGS. 3A–3B Homology between the 515.85.1 ORF and the Vaccinia virus 01L ORF. The first line shows a restriction map of the SPV HindIII M fragment. The second map shows a restriction map of the DNA insertion in plasmid 515-85.1. The location of the 515-85.1 [VV 01L-like] ORF is indicated on the map. The locations of the DNA sequences shown in FIGS. 2A–2B are indicated below the map by heavy bars. The third line shows the homology between the VV 01L ORF (SEQ ID NO:5) and the 515-85.1 ORF (SEQ ID NO:6) at their respective N-termini. The fourth line shows the homology between the VV 01L ORF (SEQ ID NO:7) and the 515-85.1 ORF (SEQ ID NO:8) at their respective C-termini.

FIG. 6 Western blot of lysates from recombinant SPV infected cells with anti-serum to PRV. Lanes (A) uninfected Vero cell lysate, (B) S-PRV-000 (pseudorabies virus S62/26) infected cell lysate, (C) pre-stained molecular weight markers, (D) uninfected EMSK cell lysate, (E) S-SPV-000 infected cell lysate, (F) S-SPV-003 infected cell lysate, (G) S-SPV-008 infected cell lysate. Cell lysates were prepared as described in the PREPARATION OF INFECTED CELL LYSATES. Approximately ⅕ of the total lysate sample was loaded in each lane.

FIG. 7 DNA sequence of NDV Hemagglutinin-Neuraminidase gene (HN) (SEQ ID NO: 29). The sequence of 1907 base pairs of the NDV HN cDNA clone are shown. The translational start and stop of the HN gene is indicated by the amino acid translation below the DNA sequence.

FIGS. 8A–8C Detailed description of the DNA insertion in Homology Vector 538-46.26. Diagram showing the orientation of DNA fragments assembled in plasmid 538-46.26. The origin of each fragment is indicated in the table. The sequences located at each of the junctions between fragments is also shown (SEQ ID NO's: 31, 32, 34, 37, and 40). The restriction sites used to generate each fragment as well as the synthetic linker sequences which were used to join the fragments are described for each junction. The synthetic linker sequences are underlined by a heavy bar. The location of several gene coding regions and regulatory elements is also given. The following two conventions are used: numbers in parenthesis ( ) refer to amino acids, and restriction sites in brackets [ ] indicate the remnants of sites which were destroyed during construction. The following abbreviations are used, swinepox virus (SPV), Newcastle Disease virus (NDV), hemagglutinin-neuraminidase (HN), early promoter 1 (EP1), late promoter 1 (LP1), late promoter 2 (LP2), lactose operon Z gene (lacZ), and *Escherichia coli* (*E. coli*).

FIGS. 9A–9C Detailed description of Swinepox Virus S-SPV-010 and the DNA insertion in Homology Vector 561-36.26. Diagram showing the orientation of DNA fragments assembled in plasmid 561-36.26. The origin of each fragment is indicated in the table. The sequences located at each of the junctions between fragments is also shown (SEQ ID. NO: 47, 48, 49, 50, 51, 52). The restriction sites used to generate each fragment as well as synthetic linker sequences which are used to join the fragments are described for each junction. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), *Escherichia coli* (*E. coli*), thymidine kinase (TK), pox synthetic late promoter 1 (LP1), base pairs (BP).

FIGS. 10A–10D Detailed description of Swinepox Virus S-SPV-011 and the DNA insertion in Homology Vector 570-91.21. Diagram showing the orientation of DNA fragments assembled in plasmid 570-91.21. The origin of each fragment is indicated in the table. The sequences located at each of the junctions between fragments is also shown (SEQ ID NO: 53, 54, 55, 56, 57, 58, 59, 60). The restriction sites used to generate each fragment as well as synthetic linker sequences which are used to join the fragments are described for each junction. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), pseudorabies virus (PRV), *Escherichia coli* (*E. coli*), pox synthetic late promoter 1 (LP1), pox synthetic early promoter 2 (EP2) (SEQ ID NO: 45), gIII (gpC), base pairs (BP).

FIGS. 11A–11D Detailed description of Swinepox Virus S-SPV-012 and the DNA insertion in Homology Vector 570-91.41. Diagram showing the orientation of DNA fragments assembled in plasmid 570-91.41. The origin of each fragment is indicated in the table. The sequences located at each of the junctions between fragments is also shown (SEQ ID NO: 61, 62, 63, 64, 65, 66, 67, 68). The restriction sites used to generate each fragment as well as synthetic linker sequences which are used to join the fragments are described for each junction. The location of several gene coding regions and regulatory elements is also given. The following two conventions are used: numbers in parentheses, ( ), refer to amino acids, and restriction sites brackets, [ ], indicate the remnants of sites which are destroyed during construction. The following abbreviations are used: swinepox virus (SPV), pseudorabies virus (PRV), *Escherichia coli* (*E. coli*), pox synthetic late promoter 1 (LP1), pox synthetic early promoter 1 late promoter 2 (EP1LP2) (SEQ ID NO: 43), gIII (gpC), base pairs (BP).

FIGS. 12A–12D Detailed description of Swinepox Virus S-PRV-013 and the DNA insertion in Homology Vector 570-91.64. Diagram showing the orientation of DNA fragments assembled in plasmid 570-91.64. The origin of each fragment is indicated in the table. The sequences located at each of the junctions between fragments is also shown (SEQ ID NO: 69, 70, 71, 72, 73, 74, 75, 76). The restriction sites used to generate each fragment as well as synthetic linker sequences which are used to join the fragments are described for each junction. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), pseudorabies virus (PRV), *Escherichia coli* (*E. coli*), pox synthetic late promoter 1 (LP1), pox synthetic late promoter 2 early promoter 2 (LP2EP2) (SEQ ID NO: 44), gIII (gpC) base pairs (BP).

FIGS. 13A–13D Detailed description of Swinepox Virus S-PRV-014 and the DNA insertion in Homology Vector 599-65.25. Diagram showing the orientation of DNA fragments assembled in plasmid 599-65.25. The origin of each fragment is indicated in the table. The sequences located at each of the junctions between fragments is also shown (SEQ ID NO: 77, 78, 79, 80, 81, 82, 83, 84). The restriction sites used to generate each fragment as well as synthetic linker sequences which are used to join the fragments are described for each junction. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), infectious laryngotracheitis virus (ILT), *Escherichia coli* (*E. coli*), pox synthetic late promoter 1 (LP1), pox synthetic early promoter 1 late promoter 2 (EP1LP2), glycoprotein G (gpG), polymerase chain reaction (PCR), base pairs (BP).

FIGS. 14A–14D Detailed description of Swinepox Virus S-SPV-016 and the DNA insertion in Homology Vector 624-20.1C. Diagram showing the orientation of DNA fragments assembled in plasmid 624-20.1C. The origin of each fragment is indicated in the table. The sequences located at each of the junctions between fragments is also shown (SEQ ID NO: 85, 86, 87, 88, 89, 90, 91, 92, 93). The restriction sites are used to generate each fragment as well as synthetic linker sequences which are used to join the fragments are described for each junction. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), infectious laryngotracheitis virus (ILT), *Escherichia coli* (*E. coli*), pox synthetic late promoter 1 (LP1), pox synthetic late promoter 2 early promoter 2 (LP2EP2), glycoprotein I (gpI), polymerase chain reaction (PCR), base pairs (BP).

FIG. 16 Western blot of lysates from recombinant SPV infected cells with polyclonal goat anti-PRV gIII (gpc). Lanes (A) S-PRV-002 (U.S. Pat. No. 4,877,737, issued Oct. 31, 1989) infected cell lysate, (B) molecular weight markers, (C) mock-infected EMSK cell lysate, (D) S-SPV-003 infected cell lysate, (E) S-SPV-008 infected cell lysate, (F) S-SPV-011 infected cell lysate, (G) S-SPV-012 infected cell lysate, (H) S-SPV-013 infected cell lysate. Cell lysates are prepared as described in the PREPARATION OF INFECTED CELL LYSATES. Approximately ⅕ of the total lysates sample is loaded in each lane.

DETAILED DESCRIPTION OF THE INVENTION

Figure 1:
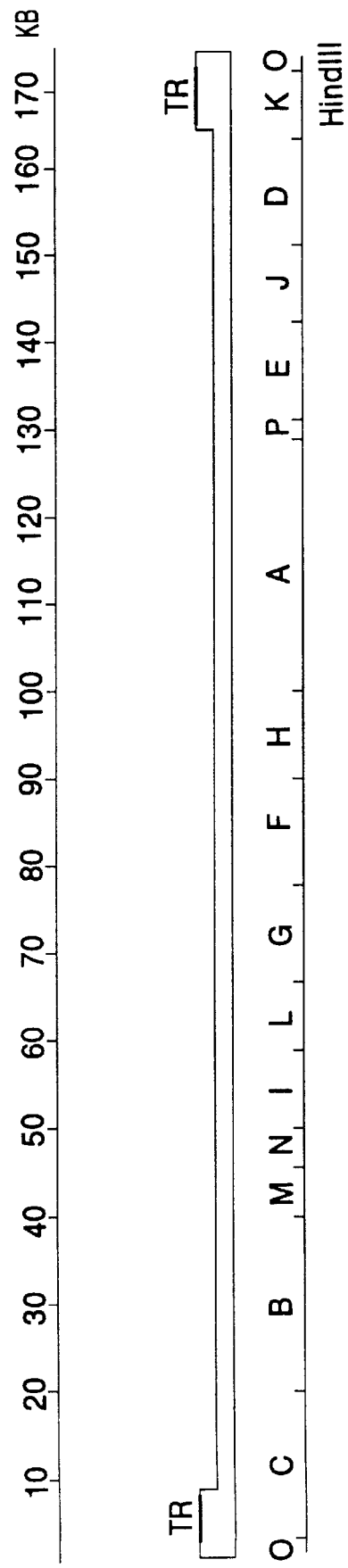
FIG. 1 Details of the SPV Kasza Strain. Diagram of SPV genomic DNA showing the unique long and Terminal repeat (TR) regions. A restriction map for the enzyme HindIII is indicated (23). Fragments are lettered in order of decreasing size. Note that the terminal repeats are greater than 2.1 kb but less than 9.7 kb in size.

The present invention provides a recombinant swinepox virus (SPV) capable of replication in an animal into which the recombinant swinepox virus is introduced which comprises swinepox viral DNA and foreign DNA encoding RNA which does not naturally occur in the animal into which the recombinant swinepox virus is introduced, the foreign DNA being inserted into the swinepox viral DNA at an insertion site which is not essential for replication of the swinepox virus and being under the control of a promoter.

For purposes of this invention, "a recombinant swinepox virus capable of replication" is a live swinepox virus which has been generated by the recombinant methods well known to those of skill in the art, e.g., the methods set forth in HOMOLOGOUS RECOMBINATION PROCEDURE FOR GENERATING RECOMBINANT SPV in *Materials and Methods* and has not had genetic material essential for the replication of the recombinant swinepox virus deleted.

For purposes of this invention, "an insertion site which is not essential for replication of the swinepox virus" is a location in the swinepox viral genome where a sequence of DNA is not necessary for viral replication, for example, complex protein binding sequences, sequences which code for reverse transcriptase or an essential glycoprotein, DNA sequences necessary for packaging, etc. For purposes of this invention, a "promoter" is a specific DNA sequence on the DNA molecule to which the foreign RNA polymerase attaches and at which transcription of the foreign RNA is initiated.

The invention further provides foreign RNA which encodes a polypeptide. Preferably, the polypeptide is antigenic in the animal. Preferably, this antigenic polypeptide is a linear polymer of more than 10 amino acids linked by peptide bonds which stimulates the animal to produce antibodies.

The invention further provides an insertion site present within the larger HindIII to BglII subfragment of the HindIII M fragment of swinepox viral DNA. Preferably, the insertion site is within an open reading frame contained in the HindIII to BglII subfragment. Preferably, the insertion site is the AccI restriction endonuclease site located in the HindIII to BglII subfragment.

The invention further provides an insertion site within an open reading frame encoding swinepox thymidine kinase. Preferably, the insertion site is the NdeI restriction endonuclease site located within the swinepox virus thymidine kinase gene.

For purposes of this invention, an "open reading frame" is a segment of DNA which contains codons that can be transcribed into RNA which can be translated into an amino acid sequence and which does not contain a termination codon.

The invention further provides a recombinant swinepox virus capable of replication which contains a foreign DNA encoding a polypeptide which is a detectable marker. Preferably the detectable marker is the polypeptide E. coli β-galactosidase. Preferably, the insertion site for the foreign DNA encoding E. coli β-galactosidase is the AccI restriction endonuclease site located within the HindIII M fragment of the swinepox viral DNA. Preferably, this recombinant swinepox virus is designated S-SPV-003 (ATCC Accession No. VR 2335). The S-SPV-003 swinepox virus has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2335. For purposes of this invention, a "polypeptide which is a detectable marker" includes the bimer, trimer and tetramer form of the polypeptide. E. coli β-galactosidase is a tetramer composed of four polypeptides or monomer sub-units.

The invention further provides a recombinant swinepox virus capable of replication which contains foreign DNA encoding an antigenic polypeptide which is or is from pseudorabies virus (PRV) g50 (gpD), pseudorabies virus (PRV) II (gpB), Pseudorabies virus (PRV) gIII (gpC), Pseudorabies virus (PRV) glycoprotein H, Transmissible gastroenteritis (TGE) glycoprotein 195, Transmissible gastroenteritis (TGE) matrix protein, swine rotavirus glycoprotein 38, swine parvovirus capsid protein, Serpulina hydodysenteriae protective antigen, Bovine Viral Diarrhea (BVD) glycoprotein 55, Newcastle Disease Virus (NDV) hemagglutinin-neuraminidase, swine flu hemagglutinin or swine flu neuraminidase. Preferably, the antigenic polypeptide is Pseudorabies Virus (PRV) g50 (gpD). Preferably, the antigenic protein is Newcastle Disease Virus (NDV) hemagglutinin-neuraminidase.

The invention further provides a recombinant swinepox virus capable of replication which contains foreign DNA encoding an antigenic polypeptide which is or is from Serpulina hyodysenteriae, Foot and Mouth Disease Virus, Hog Cholera Virus, Swine Influenza Virus, African Swine Fever Virus or Mycoplasma hyopneumoniae.

The invention further provides for a recombinant swinepox virus capable of replication which contains foreign DNA encoding pseudorabies virus (PRV) g50 (gpD). This recombinant swinepox virus can be further engineered to contain foreign DNA encoding a detectable marker, such as E. coli B-galactosidase. A preferred site within the swinepox viral genome for insertion of the foreign DNA encoding PRV g50 (gpD) and E. coli B-galactosidase is the AccI site within the HindIII M fragment of the swinepox viral DNA. Preferably, this recombinant swinepox virus is designated S-SPV-008 (ATCC Accession No. VR 2339). The S-SPV-008 swinepox virus has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2339.

The invention further provides for a recombinant swinepox virus capable of replication which contains foreign DNA encoding pseudorabies virus (PRV) gIII (gpC). This recombinant swinepox virus can also be further engineered to contain foreign DNA encoding a detectable marker, such as E. coli B-galactosidase. A preferred site within the swinepox viral DNA for insertion of the foreign DNA encoding PRV C gene and E. coli B-galactosidase is the AccI site within the HindIII M fragment of the swinepox viral DNA. Preferably, this recombinant swinepox virus is designated S-SPV-011, S-SPV-012, or S-SPV-013. The swinepox virus designated S-SPV-013 has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2418.

The invention further provides for a recombinant swinepox virus capable of replication which contains foreign DNA encoding pseudorabies virus (PRV) gII (gpB). This recombinant swinepox virus can also be further engineered to contain foreign DNA encoding a detectable marker, such as E. coli B-galactosidase. A preferred site within the swinepox viral DNA for insertion of the foreign DNA encoding PRV gII (gpB) and E. coli B-galactosidase is the AccI site within the HindIII M fragment of the swinepox viral DNA. Preferably, this recombinant swinepox virus is designated S-SPV-015.

The invention further provides for a recombinant swinepox virus capable of replication which contains foreign DNA encoding pseudorabies virus (PRV) g50 (gpD) and foreign DNA encoding pseudorabies virus (PRV) gIII (gpC). This recombinant swinepox virus can also be further engineered to contain foreign DNA encoding a detectable marker, such as E. coli B-galactosidase. A preferred site within the swinepox viral DNA for insertion of the foreign DNA encoding PRV g50 (gpD), PRV gIII (gpC) and E. coli B-galactosidase is the AccI site within the HindIII M fragment of the swinepox viral DNA.

The invention further provides for a recombinant swinepox virus capable of replication which contains foreign DNA encoding pseudorabies virus (PRV) g50 (gpD) and foreign DNA encoding pseudorabies virus (PRV) gII (gpB).

This recombinant swinepox virus can also be further engineered to contain foreign DNA encoding a detectable marker, such as E. coli B-galactosidase. A preferred site within the swinepox viral genome for insertion of foreign DNA encoding PRV g50 (gpD), PRV gII (gpB) and E. coli B-galactosidase is the AccI site within the HindIII M fragment of the swinepox viral DNA.

The invention further provides for a recombinant swinepox virus capable of replication which contains foreign DNA encoding pseudorabies virus (PRV) gIII (gpC) and foreign DNA encoding pseudorabies virus (PRV) gII (gpB). This recombinant swinepox virus can also be further engineered to contain foreign DNA encoding a detectable marker, such as E. coli B-galactosidase. A preferred site within the swinepox viral genome for insertion of foreign DNA encoding PRV gIII (gpC), PRV gII (gpB) and E. coli B-galactosidase is the AccI site within the HindIII M fragment of the swinepox viral DNA.

The invention further provides for a recombinant swinepox virus capable of replication which contains foreign DNA encoding pseudorabies virus (PRV) g50 (gpD), foreign DNA encoding pseudorabies virus (PRV) gIII (gpC), and foreign DNA encoding pseudorabies virus (PRV) gII (gpB). This recombinant swinepox virus can also be further engineered to contain foreign DNA encoding a detectable marker, such as E. coli B-galactosidase.

A preferred site within the swinepox viral genome for insertion of foreign DNA encoding PRV g50 (gpD), PRV gIII (gpC), PRV gII (gpB) and E. coli B-galactosidase is the AccI site within the HindIII M fragment of the swinepox viral DNA.

The invention further provides for a recombinant swinepox virus capable of replication which contains foreign DNA encoding RNA encoding the antigenic polypeptide Newcastle Disease Virus (NDV) hemagglutinin-neuraminidase further comprising foreign DNA encoding a polypeptide which is a detectable marker. Preferably, this recombinant swinepox virus is designated S-SPV-009 (ATCC Accession No. VR 2344). The S-SPV-009 swinepox virus has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2344.

The invention further provides that the inserted foreign DNA is under the control of a promoter. Preferably, the promoter is a swinepox viral promoter. Preferably, the promoter is a synthetic pox viral promoter. For purposes of this invention, the promoters were generated by methods well known to those of skill in the art, for example, as set forth in the STRATEGY FOR THE CONSTRUCTION OF SYNTHETIC POX VIRAL PROMOTERS in *Materials and Methods*. For purposes of this invention, a synthetic pox promoter includes a synthetic late pox promoter, a synthetic early pox promoter or a synthetic early/late pox promoter.

The invention provides for a homology vector for producing a recombinant swinepox virus by inserting foreign DNA into the genomic DNA of a swinepox virus. The homology vector comprises a double-stranded DNA molecule consisting essentially of a double-stranded foreign DNA encoding RNA which does not naturally occur in an animal into which the recombinant swinepox virus is introduced, with at one end of the foreign DNA, double-stranded swinepox viral DNA homologous to genomic DNA located at one side of a site on the genomic DNA which is not essential for replication of the swinepox virus, and at the other end of the foreign DNA, double-stranded swinepox viral DNA homologous to genomic DNA located at the other side of the same site on the genomic DNA. Preferably, the RNA encodes a polypeptide.

In one embodiment, the polypeptide is a detectable marker. Preferably, the polypeptide which is a detectable marker is E. coli β-galactosidase.

In one embodiment, the polypeptide is antigenic in the animal. Preferably, the antigenic polypeptide is or is from pseudorabies virus (PRV) g50 (gpD), pseudorabies virus (PRV) gII (gpB), Pseudorabies virus (PRV) gIII (gpC), Pseudorabies virus (PRV) glycoprotein H, Transmissible gastroenteritis (TGE) glycoprotein 195, Transmissible gastroenteritis (TGE) matrix protein, swine rotavirus glycoprotein 38, swine parvovirus capsid protein, *Serpulina hyodysenteriae* protective antigen, Bovine Viral Diarrhea (BVD) glycoprotein 55, Newcastle Disease Virus (NDV) hemagglutinin-neuraminidase, swine flu hemagglutinin or swine flu neuraminidase. Preferably, the antigenic polypeptide is or is from *Serpulina hyodysenteriae*, Foot and Mouth Disease Virus, Hog Cholera Virus, Swine Influenza Virus, African Swine Fever Virus or *Mycoplasma hyopneumoniae*.

In one embodiment of the invention, the double-stranded swinepox viral DNA is homologous to genomic DNA present within the larger HindIII to BglII subfragment of the HindIII M fragment of swinepox virus. Preferably, the double-stranded swinepox viral DNA is homologous to genomic DNA present within the open reading frame contained in this HindIII to BglII subfragment. Preferably, the double-stranded swinepox viral DNA is homologous to genomic DNA present within the AccI restriction endonuclease site located in this HindIII to BglII subfragment.

For purposes of this invention, a "homology vector" is a plasmid constructed to insert foreign DNA in a specific site on the genome of a swinepox virus.

In one embodiment of the invention, the double-stranded swinepox viral DNA in the homology vector is homologous to genomic DNA present within the open reading frame encoding swinepox thymidine kinase. Preferably, the double-stranded swinepox viral DNA is homologous to genomic DNA present within the NdeI restriction endonuclease site located in the open reading frame encoding swinepox thymidine kinase.

The invention further provides a homology vector where foreign DNA further comprises a synthetic pox viral promoter.

The invention further provides a vaccine which comprises an effective immunizing amount of a recombinant swinepox virus of the present invention and a suitable carrier.

Suitable carriers for the pseudorabies virus are well known in the art and include proteins, sugars, etc. One example of such a suitable carrier is a physiologically balanced culture medium containing one or more stabilizing agents such as stabilized, hydrolyzed proteins, lactose, etc.

For purposes of this invention, an "effective immunizing amount" of the recombinant swinepox virus of the present invention is within the range of $10^3$ to $10^9$ PFU/dose.

The present invention also provides a method of immunizing an animal, wherein the animal is a swine, bovine, equine, caprine or ovine. For purposes of this invention, this includes immunizing the animal against the virus or viruses which cause the disease or diseases pseudorabies, transmissible gastroenteritis, swine rotavirus, swine parvovirus, *Serpulina hyodysenteriae*, bovine viral diarrhea, Newcastle disease, swine flu, foot and mouth disease, hog cholera, African swine fever or *Mycoplasma hyopneumoniae*. The method comprises administering to the animal an effective immunizing dose of the vaccine of the present invention. The vaccine may be administered by any of the methods well known to those skilled in the art, for example, by intramuscular, subcutaneous, intraperitoneal or intravenous injection. Alternatively, the vaccine may be administered intranasally or orally.

The present invention also provides a method for testing a swine to determine whether the swine has been vaccinated with the vaccine of the present invention, particularly the embodiment which contains the recombinant swinepox virus S-SPV-008 (ATCC Accession No. VR 2339), or is infected with a naturally-occurring, wild-type pseudorabies virus. This method comprises obtaining from the swine to be tested a sample of a suitable body fluid, detecting in the sample the presence of antibodies to pseudorabies virus, the absence of such antibodies indicating that the swine has been neither vaccinated nor infected, and for the swine in which antibodies to pseudorabies virus are present, detecting in the sample the absence of antibodies to pseudorabies virus antigens which are normally present in the body fluid of a swine infected by the naturally-occurring pseudorabies virus but which are not present in a vaccinated swine indicating that the swine was vaccinated and is not infected.

The present invention also provides a host cell infected with a recombinant swinepox virus capable of replication. In one embodiment, the host cell is a mammalian cell.

Preferably, the mammalian cell is a Vero cell. Preferably, the mammalian cell is an ESK-4 cell, PK-15 cell or EMSK cell.

For purposes of this invention a "host cell" is a cell used to propagate a vector and its insert. Infecting the cells was accomplished by methods well known to those of skill in the art, for example, as set forth in INFECTION—TRANSFECTION PROCEDURE in *Material and Methods*.

Methods for constructing, selecting and purifying recombinant swinepox virus, including S-SPV-003, S-SPV-008, S-SPV-011, S-SPV-012, S-SPV-013 and S-SPV-015 are detailed below in *Materials and Methods*.

MATERIALS AND METHODS

PREPARATION OF SWINEPOX VIRUS STOCK SAMPLES. Swinepox virus (SPV) samples were prepared by infecting embryonic swine kidney (EMSK) cells, ESK-4 cells, PK-15 cells or Vero cells at a multiplicity of infection of 0.01 PFU/cell in a 1:1 mixture of Iscove's Modified Dulbecco's Medium (IMDM) and RPMI 1640 medium containing 2 mM glutamine, 100 units/ml penicillin, 100 units/ml streptomycin (these components were obtained from Sigma or equivalent supplier, and hereafter are referred to as EMSK negative medium). Prior to infection, the cell monolayers were washed once with EMSK negative medium to remove traces of fetal bovine serum. The SPV contained in the initial inoculum (0.5 ml for 10 cm plate; 10 ml for T175 cm flask) was then allowed to absorb onto the cell monolayer for two hours, being redistributed every half hour. After this period, the original inoculum was brought up to the recommended volume with the addition of complete EMSK medium (EMSK negative medium plus 5% fetal bovine serum). The plates were incubated at 37° C. in 5% $CO_2$ until cytopathic effect was complete. The medium and cells were harvested and frozen in a 50 ml conical screw cap tube at −70° C. Upon thawing at 37° C., the virus stock was aliquoted into 1.0 ml vials and refrozen at −70° C. The titers were usually about $10^6$ PFU/ml.

PREPARATION OF SPV DNA. For swinepox virus DNA isolation, a confluent monolayer of EMSK cells in a T175 $cm^2$ flask was infected at a multiplicity of 0.1 and incubated 4–6 days until the cells were showing 100% cytopathic effect. The infected cells were then harvested by scraping the cells into the medium and centrifuging at 3000 rpm for 5 minutes in a clinical centrifuge. The medium was decanted, and the cell pellet was gently resuspended in 1.0 ml Phosphate Buffer Saline (PBS: 1.5 g $Na_2HPO_4$, 0.2 g $KH_2PO_4$, 0.8 g NaCL and 0.2 g KCl per liter $H_2O$) (per T175) and subjected to two successive freeze-thaws (−70° C. to 37° C.). Upon the last thaw, the cells (on ice) were sonicated two times for 30 seconds each with 45 seconds cooling time in between. Cellular debris was then removed by centrifuging (Sorvall RC-5B superspeed centrifuge) at 3000 rpm for 5 minutes in a HB4 rotor at 4° C. SPV virions, present in the supernatant, were then pelleted by centrifugation at 15,000 rpm for 20 minutes at 4° C. in a SS34 rotor (Sorvall) and resuspended in 10 mM Tris (pH 7.5). This fraction was then layered onto a 36% sucrose gradient (w/v in 10 mM tris pH 7.5) and centrifuged (Beckman L8-70M Ultracentrifuge) at 18,000 rpm for 60 minutes in a SW41 rotor (Beckman) at 4° C. The virion pellet was resuspended in 1.0 ml of 10 mM tris pH 7.5 and sonicated on ice for 30 seconds. This fraction was layered onto a 20% to 50% continuous sucrose gradient and centrifuged 16,000 rpm for 60 minutes in a SW41 rotor at 4° C. The SPV virion band located about three quarters down the gradient was harvested, diluted with 20% sucrose and pelleted by centrifugation at 18,000 rpm for 60 minutes in a SW41 rotor at 4° C. The resultant pellet was then washed once with 10 mM Tris pH 7.5 to remove traces of sucrose and finally resuspended in 10 mM Tris pH 7.5. SPV DNA was then extracted from the purified virions by lysis (4 hours at 60° C.) induced by the addition of EDTA, SDS, and proteinase K to final concentrations of 20 mM, 0.5% and 0.5 mg/ml, respectively. After digestion, three phenol:chloroform (1:1) extractions were conducted and the sample precipitated by the addition of two volumes of absolute ethanol and incubation at −20° C. for 30 minutes. The sample was then centrifuged in an Eppendorf minifuge for 5 minutes at full speed. The supernatant was decanted, and the pellet air dried and rehydrated in 0.01M Tris pH 7.5, 1 mM EDTA at 4° C.

PREPARATION OF INFECTED CELL LYSATES. For cell lysate preparation, serum free medium was used. A confluent monolayer of cells (EMSK, ESK-4, PK-15 or Vero for SPV or VERO for PRV) in a 25 $cm^2$ flask or a 60 mm petri dish was infected with 100 µl of virus sample. After cytopathic effect was complete, the medium and cells were harvested and the cells were pelleted at 3000 rpm for 5 minutes in a clinical centrifuge. The cell pellet was resuspended in 250 µl of disruption buffer (2% sodium dodecyl sulfate, 2% β-mercapto-ethanol). The samples were sonicated for 30 seconds on ice and stored at −20° C.

WESTERN BLOTTING PROCEDURE. Samples of lysates and protein standards were run on a polyacrylamide gel according to the procedure of Laemnli (1970). After gel electrophoresis the proteins were transferred and processed according to Sambrook et al. (1982). The primary antibody was a swine anti-PRV serum (Shope strain; lot370, PDV8201, NVSL, Ames, IA) diluted 1:100 with 5% non-fat dry milk in Tris-sodium chloride, and sodium Azide (TSA: 6.61 g Tris-HCl, 0.97 g Tris-base, 9.0 g NaCl and 2.0 g Sodium Azide per liter $H_2O$). The secondary antibody was a goat anti-swine alkaline phosphatase conjugate diluted 1:1000 with TSA.

MOLECULAR BIOLOGICAL TECHNIQUES. Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described by Maniatis et al. (1982) and Sambrook et al. (1989). Except as noted, these were used with minor variation.

DNA SEQUENCING. Sequencing was performed using the USB Sequenase Kit and $^{35}$S-dATP (NEN). Reactions using both the dGTP mixes and the dITP mixes were performed to clarify areas of compression. Alternatively, compressed areas were resolved on formamide gels. Templates were double-stranded plasmid subclones or single stranded M13 subclones, and primers were either made to the vector just outside the insert to be sequenced, or to previously obtained sequence. Sequence obtained was assembled and compared using Dnastar software. Manipulation and comparison of sequences obtained was performed with Superclone™ and Supersee™ programs from Coral Software.

CLONING WITH THE POLYMERASE CHAIN REACTION. The polymerase chain reaction (PCR) was used to introduce restriction sites convenient for the manipulation of various DNAs. The procedures used are described by Innis, et al. (1990). In general, amplified fragments were less than 500 base pairs in size and critical regions of amplified fragments were confirmed by DNA sequencing. The primers used in each case are detailed in the descriptions of the construction of homology vectors below.

HOMOLOGOUS RECOMBINATION PROCEDURE FOR GENERATING RECOMBINANT SPV. This method relies upon the homologous recombination between the swinepox virus DNA and the plasmid homology vector DNA which occurs in the tissue culture cells containing both swinepox virus DNA and transfected plasmid homology vector. For homologous recombination to occur, the monolayers of EMSK cells are infected with S-SPV-001 (Kasza SPV strain, 17) at a multiplicity of infection of 0.01 PFU/cell to introduce replicating SPV (i.e. DNA synthesis) into the cells. The plasmid homology vector DNA is then transfected into these cells according to the INFECTION—TRANSFECTION PROCEDURE. The construction of homology vectors used in this procedure is described below INFECTION—TRANSFECTION PROCEDURE. 6 cm plates of EMSK cells (about 80% confluent) were infected with S-SPV-001 at a multiplicity of infection of 0.01 PFU/cell in EMSK negative medium and incubated at 37° C. in a humidified 5% $CO_2$ environment for 5 hours. The transfection procedure used is essentially that recommended for Lipofectin™ Reagent (BRL). Briefly, for each 6 cm plate, 15 $\mu$g of plasmid DNA was diluted up to 100 $\mu$l with $H_2O$. Separately, 50 micrograms of Lipofectin Reagent was diluted to 100 $\mu$l with $H_2O$. The 100 $\mu$l of diluted Lipofectin Reagent was then added dropwise to the diluted plasmid DNA contained in a polystyrene 5 ml snap cap tube and mixed gently. The mixture was then incubated for 15–20 minutes at room temperature. During this time, the virus inoculum was removed from the 6 cm plates and the cell monolayers washed once with EMSK negative medium. Three ml of EMSK negative medium was then added to the plasmid DNA/lipofectin mixture and the contents pipetted onto the cell monolayer. The cells were incubated overnight (about 16 hours) at 37° C. in a humidified 5% $CO_2$ environment. The next day the 3 ml of EMSK negative medium was removed and replaced with 5 ml EMSK complete medium. The cells were incubated at 37° C. in 5% $CO_2$ for 3–7 days until cytopathic effect from the virus was 80–100%. Virus was harvested as described above for the preparation of virus stocks. This stock was referred to as a transfection stock and was subsequently screened for recombinant virus by the BLUOGAL SCREEN FOR RECOMBINANT SWINEPOX VIRUS OR CPRG SCREEN FOR RECOMBINANT SWINEPOX VIRUS.

SCREEN FOR RECOMBINANT SPV EXPRESSING B-GALACTOSIDASE (BLUOGAL AND CPRG ASSAYS). When the *E. coli* β-galactosidase (lacZ) marker gene was incorporated into a recombinant virus the plaques containing the recombinants were visualized by one of two simple methods. In the first method, the chemical Bluogal™ (Bethesda Research Labs) was incorporated (200 $\mu$g/ml) into the agarose overlay during the plaque assay, and plaques expressing active β-galactosidase turned blue. The blue plaques were then picked onto fresh cells (EMSK) and purified by further blue plaque isolation. In the second method, CPRG (Boehringer Mannheim) was incorporated (400 $\mu$g/ml) into the agarose overlay during the plaque assay, and plaques expressing active β-galactosidase turned red. The red plaques were then picked onto fresh cells (EMSK) and purified by further red plaque isolation. In both cases viruses were typically purified with three rounds of plaque purification.

SCREEN FOR FOREIGN GENE EXPRESSION IN RECOMBINANT SPV USING BLACK PLAQUE ASSAYS. To analyze expression of foreign antigens expressed by recombinant swinepox viruses, monolayers of EMSK cells were infected with recombinant SPV, overlayed with nutrient agarose media and incubated for 6–7 days at 37° C. for plaque development to occur. The agarose overlay was then removed from the dish, the cells fixed with 100% methanol for 10 minutes at room temperature and the cells air dried. Fixation of the cells results in cytoplasmic antigen as well as surface antigen detection whereas specific surface antigen expression can be detected using non-fixed cells. The primary antibody was then diluted to the appropriate dilution with PBS and incubated on the cell monolayer for 2 hours at room temperature. To detect PRV g50 (gpD) expression from S-SPV-008, swine anti-PRV serum (Shope strain; lot370, PDV8201, NVSL, Ames, IA) was used (diluted 1:100). To detect NDV HN expression from S-SPV-009, a rabbit antiserum specific for the HN protein (rabbit anti-NDV#2) was used (diluted 1:1000). Unbound antibody was then removed by washing the cells three times with PBS at room temperature. The secondary antibody, either a goat anti-swine (PRV g50 (gpD); S-SPV-008) or goat anti-rabbit (NDV HN; S-SPV-009), horseradish peroxidase conjugate was diluted 1:250 with PBS and incubated with the cells for 2 hours at room temperature. Unbound secondary antibody was then removed by washing the cells three times with PBS at room temperature. The cells were then incubated 15–30 minutes at room temperature with freshly prepared substrate solution (100 $\mu$g/ml 4-chloro-1-naphthol, 0.003% $H_2O_2$ in PBS). Plaques expressing the correct antigen stain black.

PROCEDURE FOR PURIFICATION OF VIRAL GLYCOPROTEINS FOR USE AS DIAGNOSTICS. Viral glycoproteins are purified using antibody affinity columns. To produce monoclonal antibodies, 8 to 10 week old BALB/c female mice are vaccinated intraperitoneally seven times at two to four week intervals with $10^7$ PFU of S-SPV-009, -014, -016, -017, -018, or -019. Three weeks after the last vaccination, mice are injected intraperitoneally with 40 mg of the corresponding viral glycoprotein. Spleens are removed from the mice three days after the last antigen dose.

Splenocytes are fused with mouse NS1/Ag4 plasmacytoma cells by the procedure modified from Oi and Herzenberg, (41). Splenocytes and plasmacytoma cells are pelleted together by centrifugation at 300×g for 10 minutes. One ml of a 50% solution of polyethylene glycol (m.w. 1300–1600) is added to the cell pellet with stirring over one minute. Dulbecco's modified Eagles's medium (5 ml) is added to the cells over three minutes. Cells are pelleted by centrifugation at 300×g for 10 minutes and resuspended in medium with 10% fetal bovine serum and containing 100 mM hypoxanthine, 0.4 mM aminopterin and 16 mM thymidine (HAT). Cells (100 ml) are added to the wells of eight to ten 96-well tissue culture plates containing 100 ml of normal spleen feeder layer cells and incubated at 37° C. Cells are fed with fresh HAT medium every three to four days.

Hybridoma culture supernatants are tested by the ELISA ASSAY in 96-well microtiter plates coated with 100 ng of viral glycoprotein. Supernatants from reactive hybridomas are further analyzed by black-plaque assay and by Western Blot. Selected hybridomas are cloned twice by limiting dilution. Ascetic fluid is produced by intraperitoneal injection of $5\times10^6$ hybridoma cells into pristane-treated BALB/c mice.

Figure 4A:
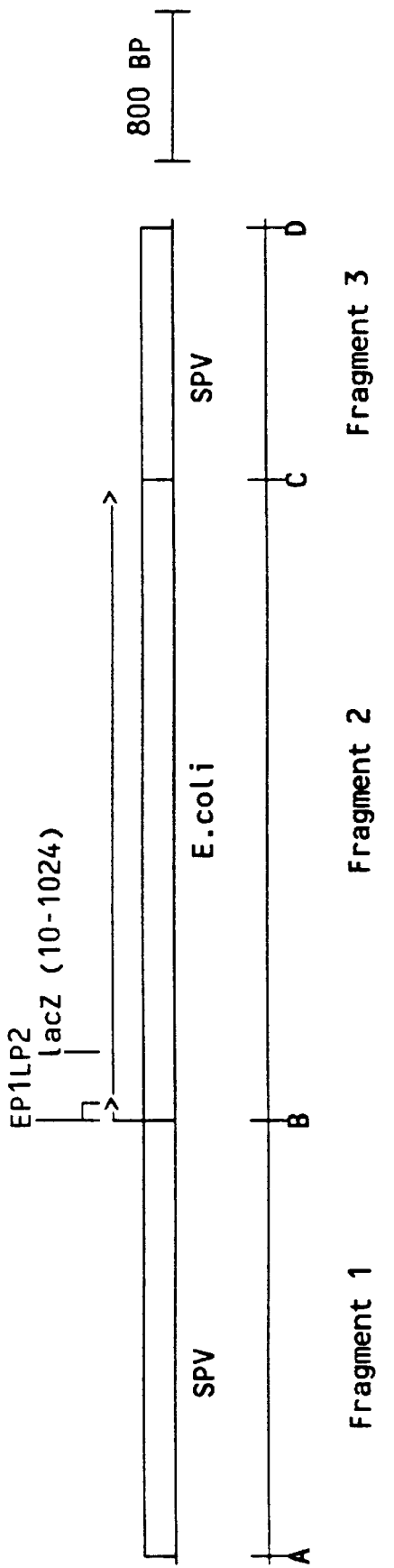
FIGS. 4A–4C Detailed description of the DNA insertion in Homology Vector 520-17.5. Diagram showing the orientation of DNA fragments assembled in plasmid 520-17.5. The origin of each fragment is indicated in the table. The sequences located at each of the junctions between fragments is also shown (SEQ ID NO's: 9, 10, 13, and 16). The restriction sites used to generate each fragment as well as the synthetic linker sequences which were used to join the fragments are described for each junction. The synthetic linker sequences are underlined by a heavy bar. The location of several gene coding regions and regulatory elements are also given. The following two conventions are used: numbers in parenthesis ( ) refer to amino acids, and restriction sites in brackets [ ] indicate the remnants of sites which were destroyed during construction. The following abbreviations are used, swinepox virus (SPV), early promoter 1 (EP1), late promoter 2 (LP2), lactose operon Z gene (lacZ), and *Escherichia coli* (*E. coli*).
Figure 4B:
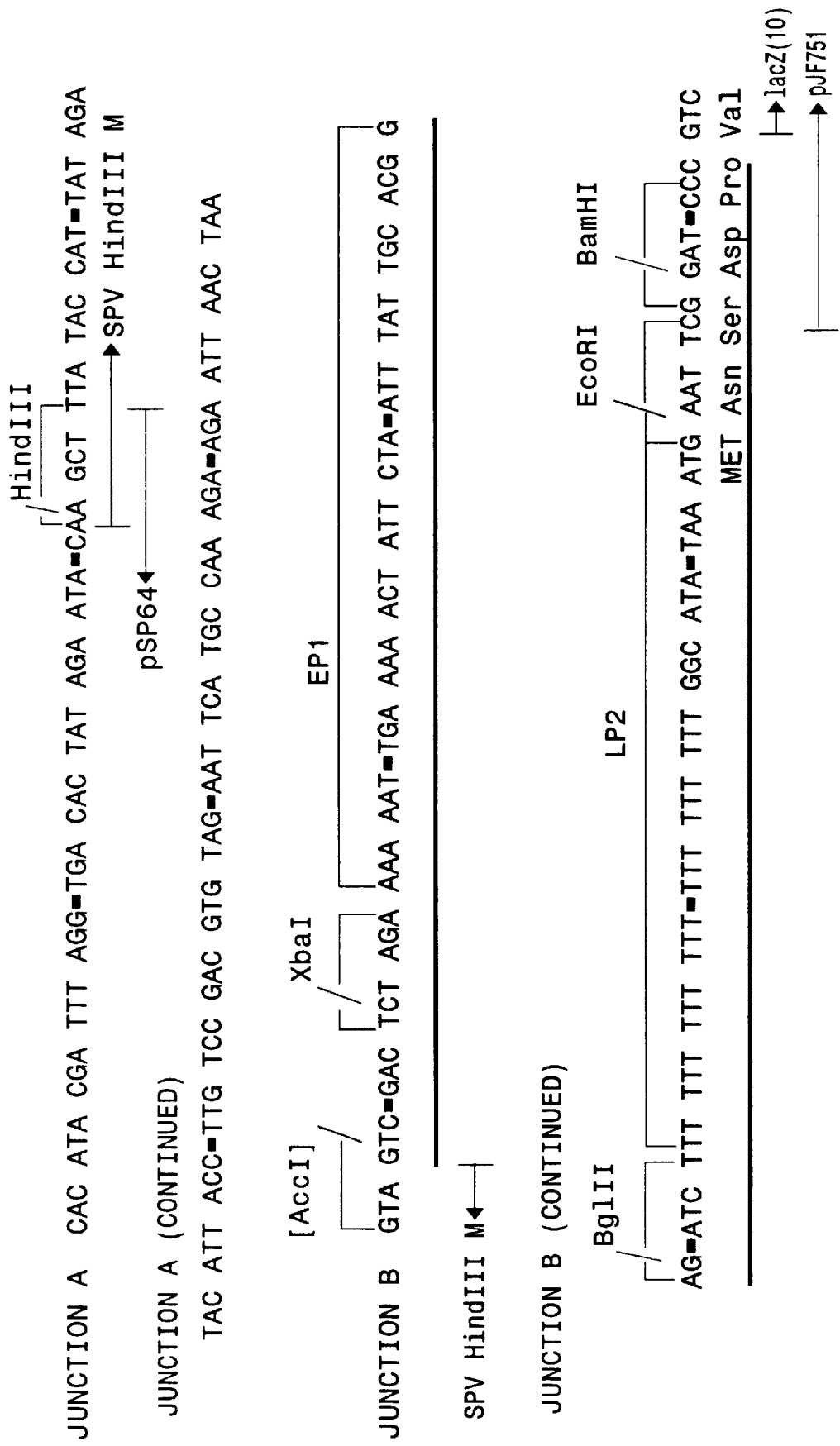
Figure 4C:
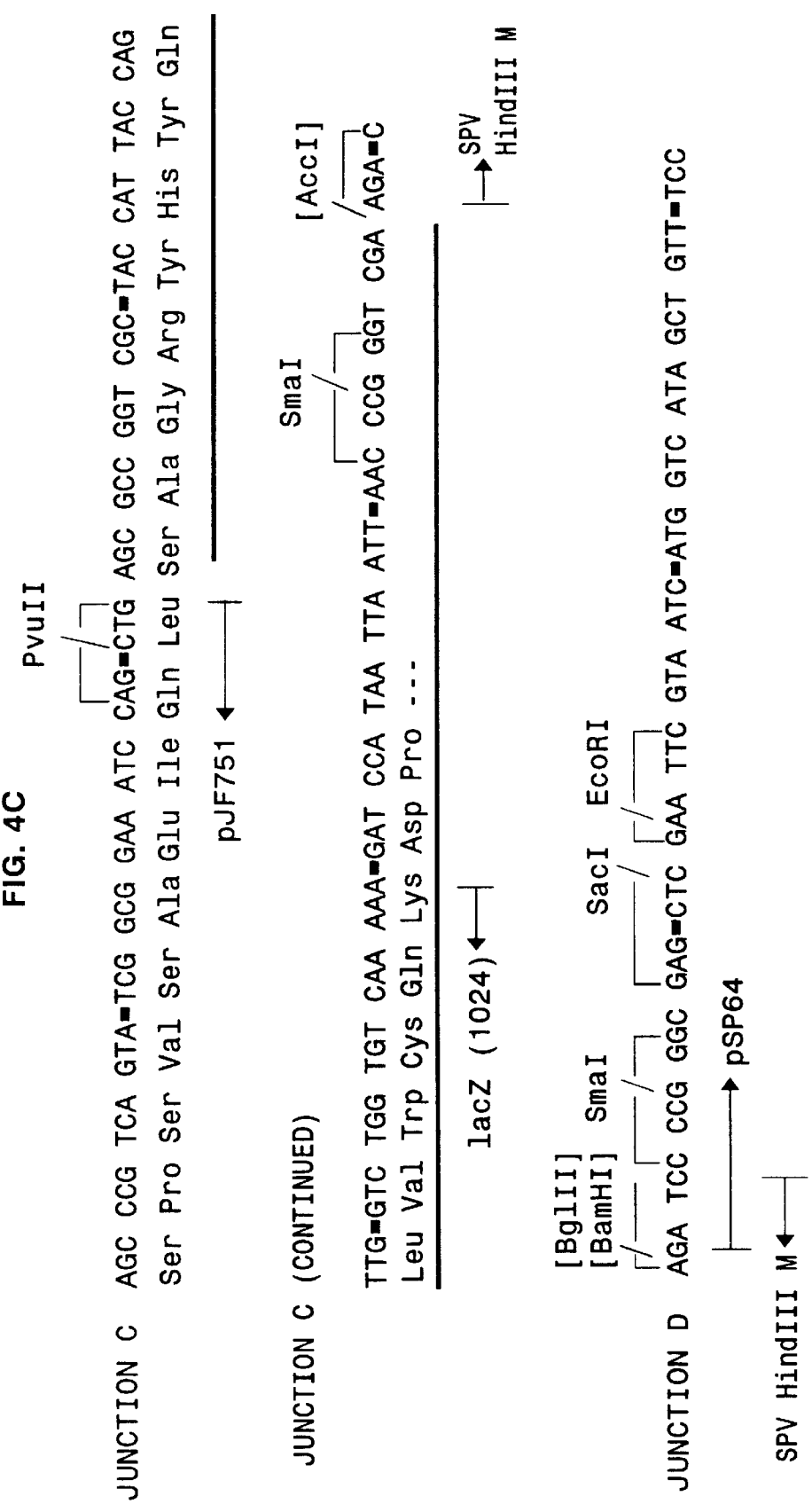
Figure 5A:
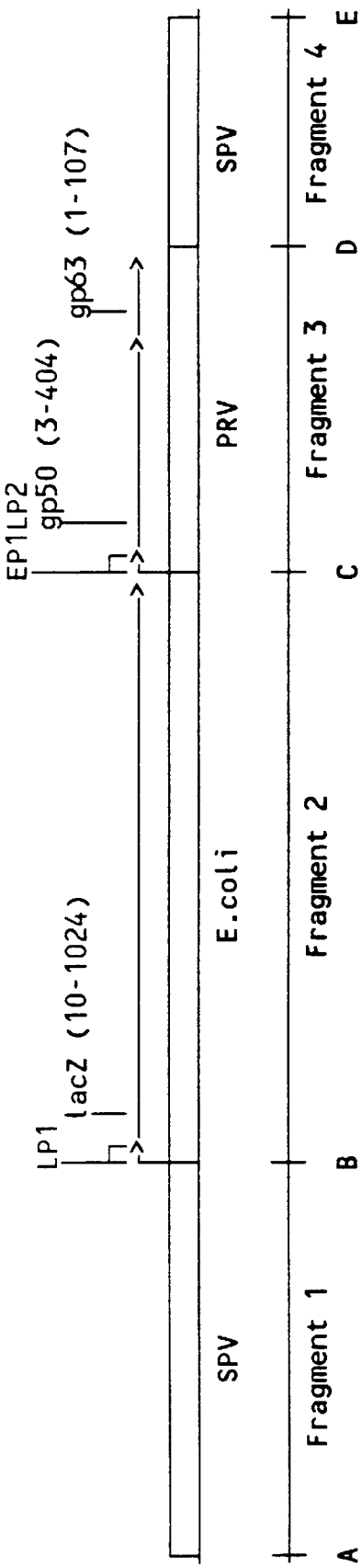
FIGS. 5A–5D Detailed description of the DNA insertion in Homology Vector 538-46.16. Diagram showing the orientation of DNA fragments assembled in plasmid 538-46.16. The origin of each fragment is indicated in the table. The sequences located at each of the junctions between fragments are also shown (SEQ ID NO's: 17, 18, 21, 26, and 28). The restriction sites used to generate each fragment as well as the synthetic linker sequences which were used to join the fragments are described for each junction. The synthetic linker sequences are underlined by a heavy bar. The location of several gene coding regions and regulatory elements is also given. The following two conventions are used: numbers in parenthesis ( ) refer to amino acids, and restriction sites in brackets [ ] indicate the remnants of sites which were destroyed during construction. The following abbreviations are used, swinepox virus (SPV), pseudorabies virus (PRV), g50 (gpD), glycoprotein 63 (gp63), early promoter 1 (EP1), late promoter 1 (LP1) (SEQ ID NO: 46), late promoter 2 (LP2), lactose operon Z gene (lacZ), and *Escherichia coli* (*E. coli*).
Figure 5B:
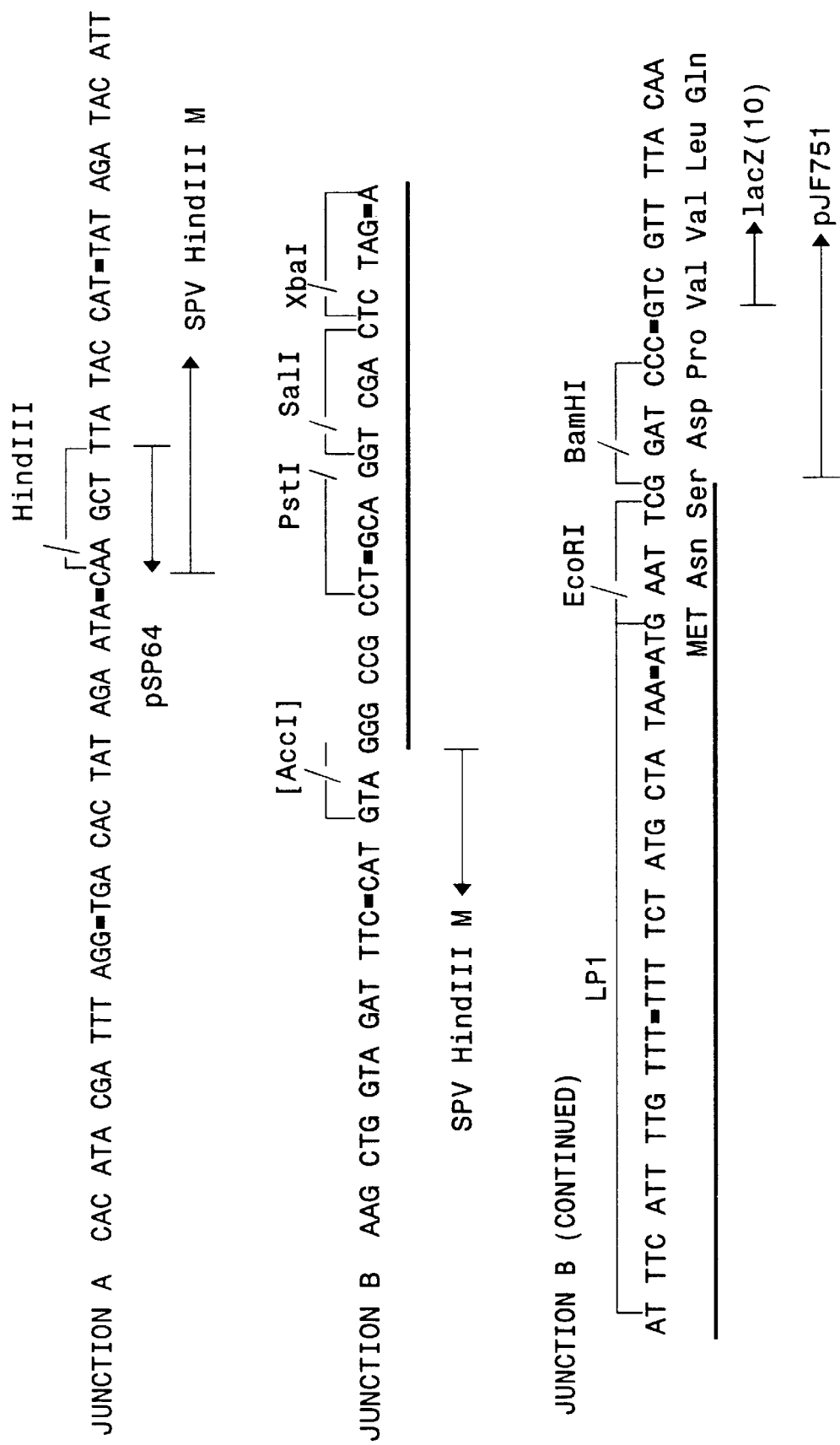
Figure 5C:
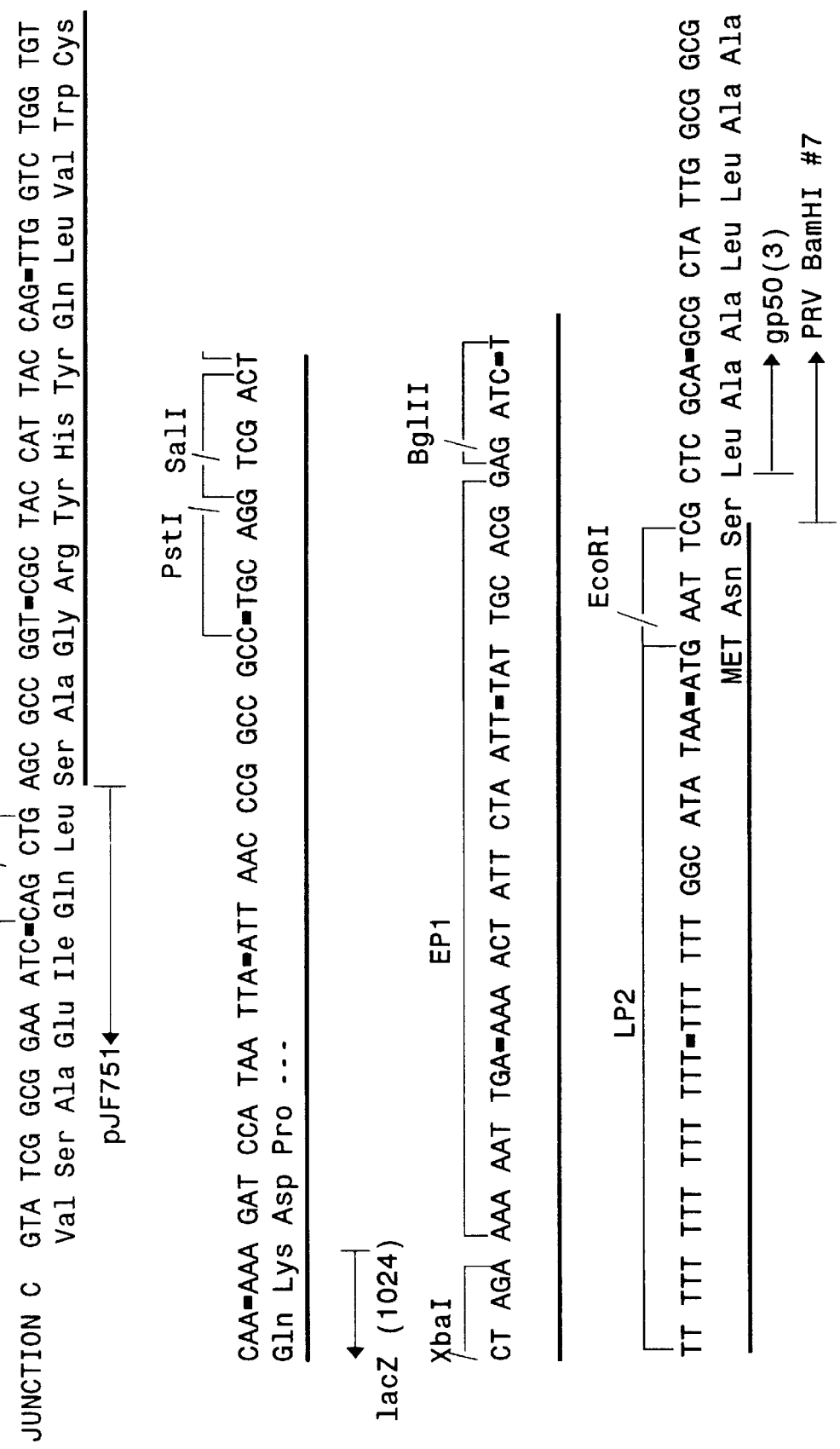
Figure 5D:
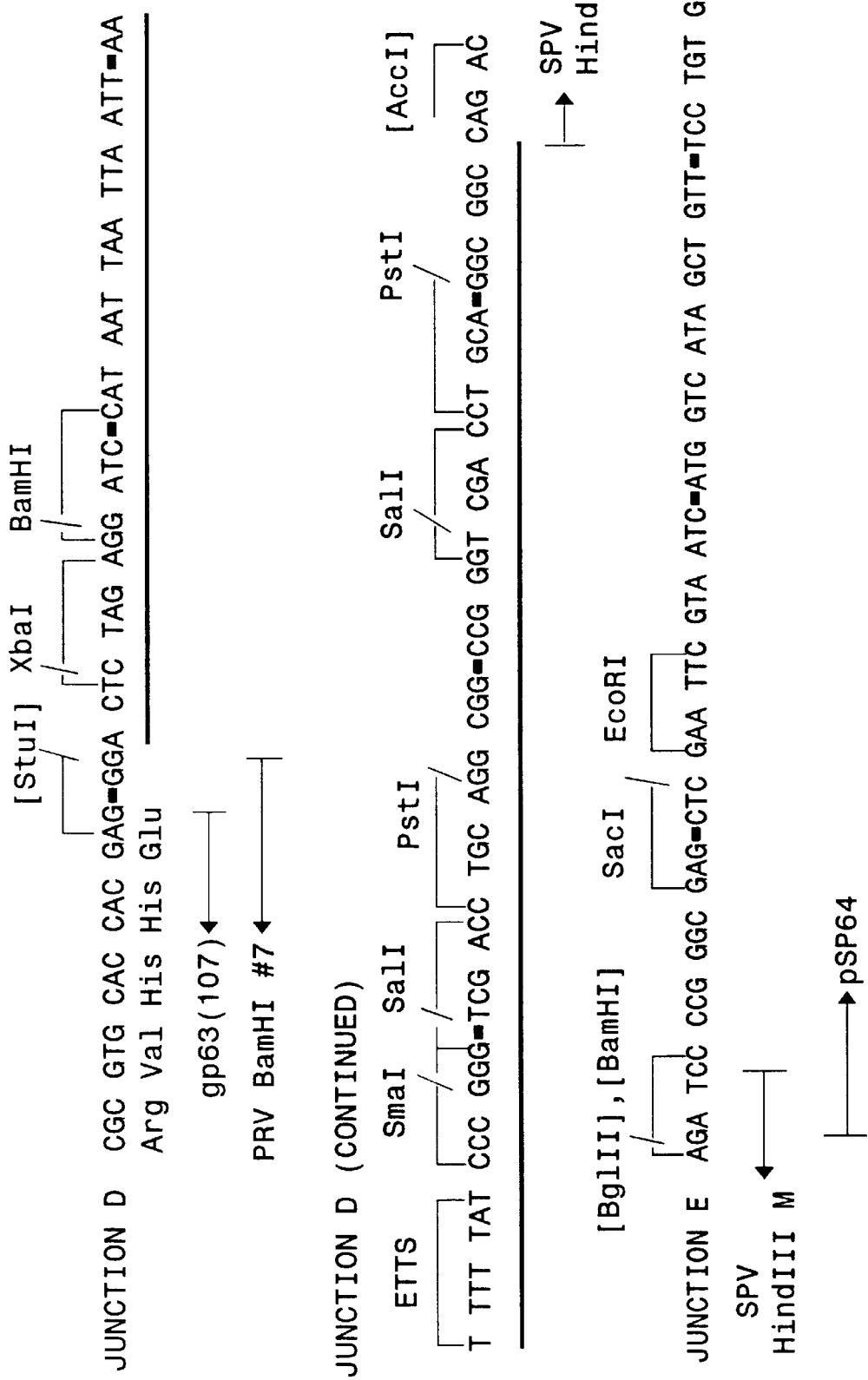

Cell lysates from S-SPV-009, -014, -016, -017, -018, or -019 are obtained as described in PREPARATION OF INFECTED CELL LYSATES. The glycoprotein-containing cell lysates (100 mls) are passed through a 2-ml agarose affinity resin to which 20 mg of glycoprotein monoclonal antibody has been immobilized according to manufacturer's instructions (AFC Medium, New Brunswick Scientific, Edison, N.J.). The column is washed with 100 ml of 0.1% Nonidet P-40 in phosphate-buffered saline (PBS) to remove nonspecifically bound material. Bound glycoprotein is eluted with 100 mM carbonate buffer, pH 10.6 (40). Pre- and posteluted fractions are monitored for purity by reactivity to the SPV monoclonal antibodies in an ELISA system.

ELISA ASSAY. A standard enzyme-linked immunosorbent assay (ELISA) protocol is used to determine the immune status of cattle following vaccination and challenge.

A glycoprotein antigen solution (100 ml at ng/ml in PBS) is allowed to absorb to the wells of microtiter dishes for 18 hours at 4° C. The coated wells are rinsed one time with PBS. Wells are blocked by adding 250 ml of PBS containing 1% BSA (Sigma) and incubating 1 hour at 37° C. The blocked wells are rinsed one time with PBS containing 0.02% Tween 20. 50 ml of test serum (previously diluted 1:2 in PBS containing 1% BSA) are added to the wells and incubated 1 hour at 37° C. The antiserum is removed and the wells are washed 3 times with PBS containing 0.02% Tween 20. 50 ml of a solution containing anti-bovine IgG coupled to horseradish peroxidase (diluted 1:500 in PBS containing 1% BSA, Kirkegaard and Perry Laboratories, Inc.) is added to visualize the wells containing antibody against the specific antigen. The solution is incubated 1 hour at 37° C., then removed and the wells are washed 3 times with PBS containing 0.02% Tween 20. 100 ml of substrate solution (ATBS, Kirkegaard and Perry Laboratories, Inc.) are added to each well and color is allowed to develop for 15 minutes. The reaction is terminated by addition of 0.1M oxalic acid. The color is read at absorbance 410 nm on an automatic plate reader.

STRATEGY FOR THE CONSTRUCTION OF SYNTHETIC POX VIRAL PROMOTERS. For recombinant swinepox vectors synthetic pox promoters offer several advantages including the ability to control the strength and timing of foreign gene expression. We chose to design three promoter cassettes LP1, EP1 and LP2 based on promoters that have been defined in the vaccinia virus (1, 7 and 8). Each cassette was designed to contain the DNA sequences defined in vaccinia flanked by restriction sites which could be used to combine the cassettes in any order or combination. Initiator methionines were also designed into each cassette such that inframe fusions could be made at either EcoRI or BamHI sites. A set of translational stop codons in all three reading frames and an early transcriptional termination signal (9) were also engineered downstream of the inframe fusion site. DNA encoding each cassette was synthesized according to standard techniques and cloned into the appropriate homology vectors (see FIGS. 4A–4C, 5A–5D, and 8A–8C).

VACCINATION STUDIES IN SWINE USING RECOMBINANT SWINEPOX VIRUS CONTAINING PSEUDORABIES VIRUS GLYCOPROTEIN GENES: Young weaned pigs from pseudorabies-free herd are used to test the efficacy of the recombinant swinepox virus containing one or more of the pseudorabies virus glycoprotein genes (SPV/PRV). The piglets are inoculated intradermally or orally about $10^3$ to $10^7$ plaque forming units (PFU) of the recombinant SPV/PRV viruses.

Immunity is determined by measuring PRV serum antibody levels and by challenging the vaccinated pigs with virulent strain of pseudorabies virus. Three to four weeks post-vaccination, both vaccinated and non-vaccinated groups of pigs are challenged with virulent strain of pseudorabies virus (VDL4892). Post challenge, the pigs are observed daily for 14 days for clinical signs of pseudorabies.

Serum samples are obtained at the time of vaccination, challenge, and at weekly intervals for two to three weeks post-vaccination and assayed for serum neutralizing antibody.

HOMOLOGY VECTOR 515-85.1. The plasmid 515-85.1 was constructed for the purpose of inserting foreign DNA into SPV. It contains a unique AccI restriction enzyme site into which foreign DNA may be inserted. When a plasmid, containing a foreign DNA insert at the AccI site, is used according to the HOMOLOGOUS RECOMBINATION PROCEDURE FOR GENERATING RECOMBINANT SPV a virus containing the foreign DNA will result. A restriction map of the DNA insert in homology vector 515-85.1 is given in FIGS. 4A–4C. It may be constructed utilizing standard recombinant DNA techniques (22 and 29), by joining two restriction fragments from the following sources. The first fragment is an approximately 2972 base pair HindIII to BamHI restriction fragment of pSP64 (Promega). The second fragment is an approximately 3302 base pair HindIII to BglII restriction sub-fragment of the SPV HindIII restriction fragment M (23).

HOMOLOGY VECTOR 520-17.5. The plasmid 520-17.5 was constructed for the purpose of inserting foreign DNA into SPV. It incorporates an *E. coli* β-galactosidase (lacZ) marker gene flanked by SPV DNA. Upstream of the marker gene is an approximately 2156 base pair fragment of SPV DNA. Downstream of the marker gene is an approximately 1146 base pair fragment of SPV DNA. When this plasmid is used according to the HOMOLOGOUS RECOMBINATION PROCEDURE FOR GENERATING RECOMBINANT SPV a virus containing DNA coding for the marker gene will result. Note that the β-galactosidase (lacZ) marker gene is under the control of a synthetic early/late pox promoter. A detailed description of the plasmid is given in FIGS. 4A–4C. It may be constructed utilizing standard recombinant DNA techniques (22 and 30), by joining restriction fragments from the following sources with the synthetic DNA sequences indicated in FIG. 4. The plasmid vector is derived from an approximately 2972 base pair HindIII to BamHI restriction fragment of pSP64 (Promega). Fragment 1 is an approximately 2156 base pair HindIII to AccI restriction sub-fragment of the SPV HindIII restriction fragment M (23). Fragment 2 is an approximately 3006 base pair BamHI to PvuII restriction fragment of plasmid pJF751 (11). Fragment 3 is an approximately 1146 base pair AccI to BglII restriction sub-fragment of the SPV HindIII fragment M (23).

HOMOLOGY VECTOR 538-46.16. The plasmid 538-46.16 was constructed for the purpose of inserting foreign DNA into SPV. It incorporates an *E. coli* β-galactosidase (lacZ) marker gene and the PRV g50 (gpD) gene flanked by SPV DNA. Upstream of the foreign genes is an approximately 2156 base pair fragment of SPV DNA. Downstream of the foreign genes is an approximately 1146 base pair fragment of SPV DNA. When this plasmid is used according to the HOMOLOGOUS RECOMBINATION PROCEDURE FOR GENERATING RECOMBINANT SPV a virus containing DNA coding for the foreign genes will result. Note that the β-galactosidase (lacZ) marker gene is under the control of a synthetic late pox promoter (LP1) and the g50 (gpD) gene is under the control of a synthetic early/late pox promoter (EP1LP2). A detailed description of the plasmid is given in FIGS. 5A–5D. It may be constructed utilizing standard recombinant DNA techniques (22 and 30), by joining restriction fragments from the following sources with the synthetic DNA sequences indicated in FIGS. 5A–5D. The plasmid vector is derived from an approximately 2972 base pair HindIII to BamHI restriction fragment of pSP64 (Promega). Fragment 1 is an approximately 2156 base pair HindIII to AccI restriction sub-fragment of the SPV HindIII restriction fragment M (23). Fragment 2 is an approximately 3006 base pair BamHI to PvuII restriction fragment of plasmid pJF751 (11). Fragment 3 is an approximately 1571 base pair EcoRI to StuI restriction sub-fragment of the PRV BamHI fragment 7 (21). Note that the EcoRI site was introduced in to this fragment by PCR cloning. In this procedure the primers described below were used along with a template consisting of a PRV BamHI #7 fragment subcloned into pSP64. The first primer 87.03 (5'-CGCGAATTCGCTCG CAGCGCTATTGGC-3') (SEQ ID NO:41) sits down on the PRV g50 (gpD) sequence (26) at approximately amino acid 3 priming toward the 3' end of the gene. The second primer 87.06 (5'-GTAGGAGTGGCTGCTGAAG-3') (SEQ ID NO:42) sits down on the opposite strand at approximately amino acid 174 priming toward the 5' end of the gene. The PCR product may be digested with EcoRI and SalII to produce an approximately 509 base pair fragment. The approximately 1049 base pair SalI to StuI sub-fragment of PRV BamHI #7 may then be ligated to the approximately 509 base pair EcoRI to SalI fragment to generate the approximately 1558 base pair EcoRI to StuI fragment 3. Fragment 4 is an approximately 1146 base pair AccI to BglII restriction sub-fragment of the SPV HindIII fragment M (23).

HOMOLOGY VECTOR 570-91.21. The plasmid 570-91.21 was constructed for the purpose of inserting foreign DNA into SPV. It incorporates an *E. coli* B-galactosidase (lacZ) marker gene and the PRV gIII (gpC) gene flanked by SPV DNA. Upstream of the foreign DNA genes is an approximately 1146 base pair fragment of SPV DNA. Downstream of the foreign genes is an approximately 2156 base pair fragment of SPV DNA. When this plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the gIII (gpC) gene is under the control of a synthetic early pox promoter (EP2). A detailed description of the plasmid is given in FIGS. 10A–10D. It may be constructed utilizing standard recombinant DNA techniques (22 and 30), by joining restriction fragments from the following sources with the synthetic DNA sequences indicated in FIGS. 10A–10D. The plasmid vector is derived from an approximately 2972 base pair HindIII to BamHI restriction fragment of pSP64 (Promega). Fragment 1 is an approximately 1146 base pair BglII to AccI restriction sub-fragment of the SPV HindIII restriction fragment M (23). Fragment 2 is an approximately 3002 base pair BamHI to PvuII restriction fragment of plasmid pJF751 (11). Fragment 3 is an approximately 2378 base pair NcoI to NcoI fragment of plasmid 251-41.A, a subfragment of PRV BamHI #2 and #9. EcoRI linkers have replaced the NcoI and NcoI sites at the ends of this fragment. Fragment 4 is an approximately 2156 base pair AccI to HindIII restriction sub-fragment of the SPV HindIII fragment M (23). The AccI sites in fragments 1 and 4 have been converted to PstI sites using synthetic DNA linkers.

HOMOLOGY VECTOR 570-91.41. The plasmid 570-91.41 was constructed for the purpose of inserting foreign DNA into SPV. It incorporates an *E. coli* B-galactosidase (lacZ) marker gene and the PRV gIII (gpC) gene flanked by SPV DNA. Upstream of the foreign DNA genes is an approximately 2156 base pair fragment of SPV DNA. Downstream of the foreign genes is an approximately 1146 base pair fragment of SPV DNA. When this plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the gIII (gpC) gene is under the control of a synthetic early late pox promoter (EP1LP2). A detailed description of the plasmid is given in FIGS. 11A–11D. It may be constructed utilizing standard recombinant DNA techniques (22 and 30), by joining restriction fragments from the following sources with the synthetic DNA sequences indicated in FIGS. 11A–11D. The plasmid vector is derived from an approximately 2972 base pair HindIII to BamHI restriction fragment of pSP64 (Promega). Fragment 1 is an approximately 1146 base pair BglII to AccI restriction sub-fragment of the SPV HindIII restriction fragment M (23). Fragment 2 is an approximately 3002 base pair BamHI to PvuII restriction fragment of plasmid pJF751 (11). Fragment 3 is an approximately 2378 base pair NcoI to NcoI fragment of plasmid 251-41.A, a subfragment of PRV BamHI #2 and #9. EcoRI linkers have replaced the NcoI and NcoI sites at the ends of this fragment. Fragment 4 is an approximately 2156 base pair AccI to HindIII restriction sub-fragment of the SPV HindIII fragment M (23). The AccI sites in fragments 1 and 4 have been converted to PstI sites using synthetic DNA linkers.

HOMOLOGY VECTOR 570-91.64. The plasmid 570-91.64 was constructed for the purpose of inserting foreign DNA into SPV. It incorporates an *E. coli* B-galactosidase (lacZ) marker gene and the PRV gIII (gpC) gene flanked by SPV DNA. Upstream of the foreign DNA genes is an approximately 1146 base pair fragment of SPV DNA. Downstream of the foreign genes is an approximately 2156 base pair fragment of SPV DNA. When this plasmid is used according to the HOMOLOGOUS RECOMBINATION PROCEDURE FOR GENERATING RECOMBINANT SPV, a virus containing DNA coding for the foreign genes will result. Note that the β-galactosidase (lacZ) marker gene is under the control of a synthetic late pox promoter (LP1), and the gIII (gpC) gene is under the control of a synthetic late early pox promoter (LP2EP2). A detailed description of the plasmid is given in FIGS. 12A–12D. It may be constructed utilizing standard recombinant DNA techniques (22 and 30), by joining restriction fragments from the following sources with the synthetic DNA sequences indicated in FIGS. 12A–12D. The plasmid vector is derived from an approximately 2972 base pair HindIII to BamHI restriction fragment of pSP64 (Promega). Fragment 1 is an approximately 1146 base pair BglII to AccI restriction sub-fragment of the SPV HindIII restriction fragment M (23). Fragment 2 is an approximately 3002 base pair BamHI to PvuII restriction fragment of plasmid pJF751 (11). Fragment 3 is an approximately 2378 base pair NcoI to NcoI fragment of plasmid 25-41.A, a subfragment of PRV BamHI #2 and #9. EcoRI linkers have replaced the NcoI and NcoI sites at the ends of this fragment. Fragment 4 is an approximately 2156 base pair AccI to HindIII restriction sub-fragment of the SPV HindIII fragment M (23). The AccI sites in fragments 1 and 4 have been converted to PstI sites using synthetic DNA linkers.

Figure 8A:
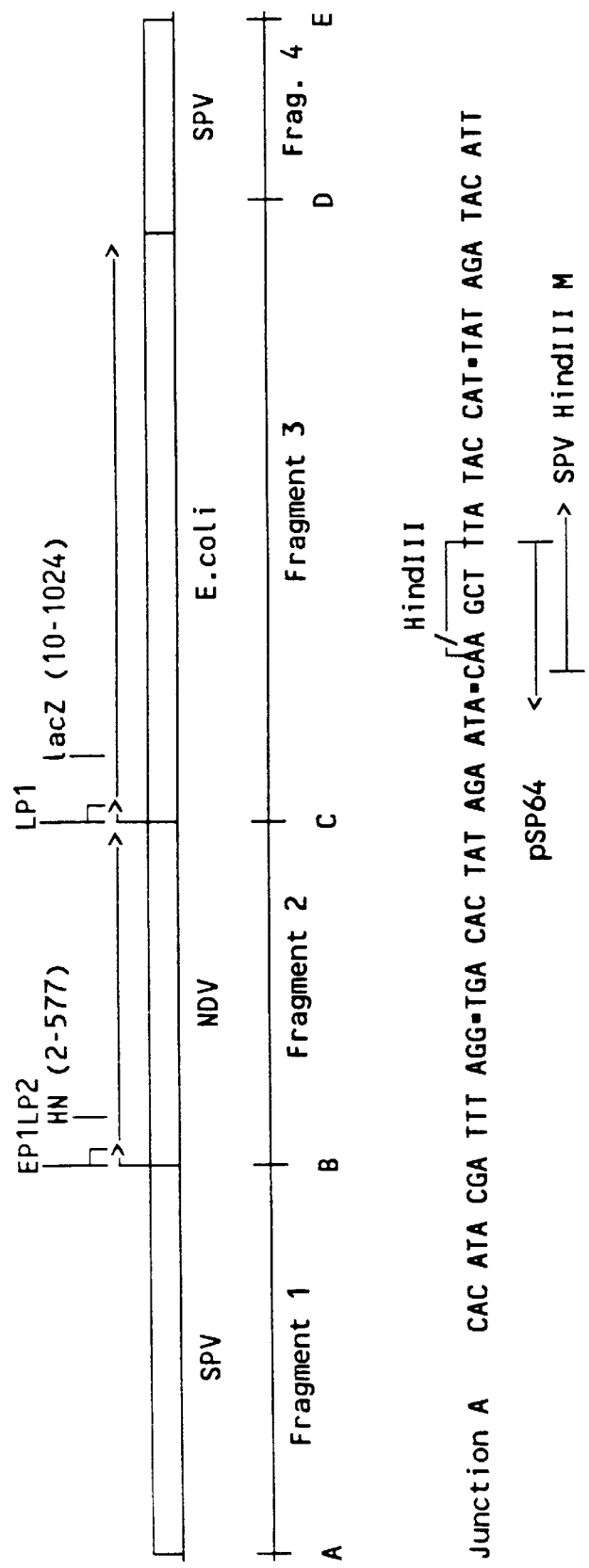
Figure 8B:
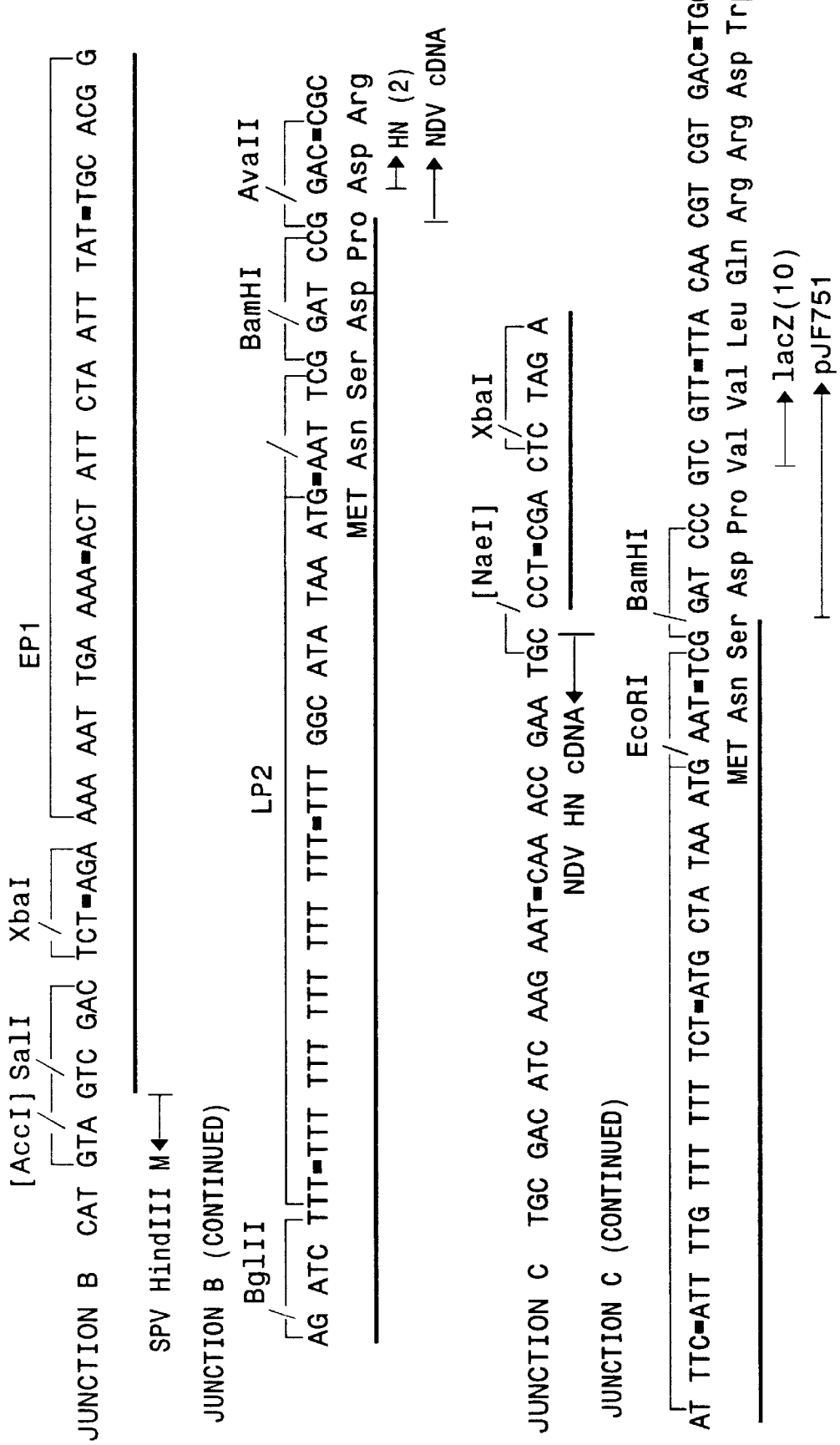
Figure 8C:
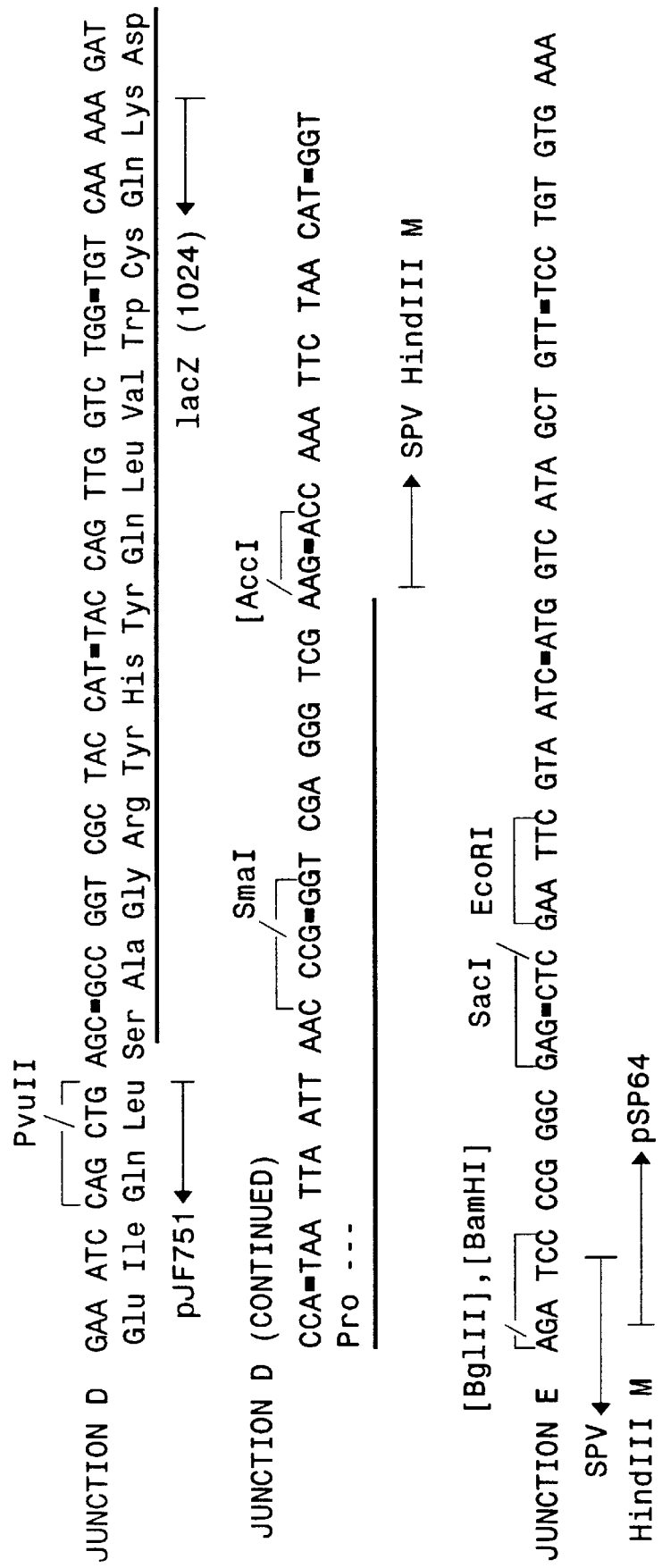
Figure 9A:
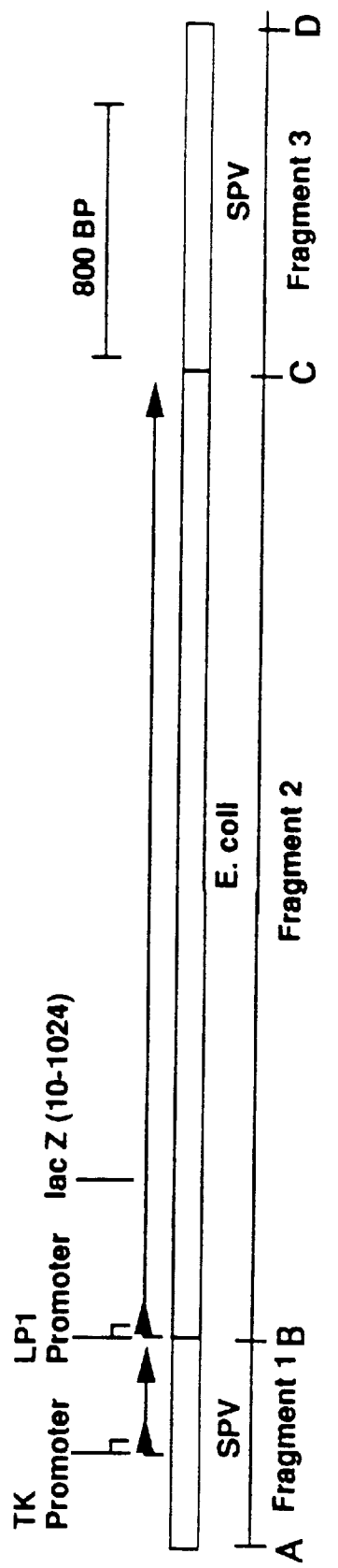
Figure 9B:
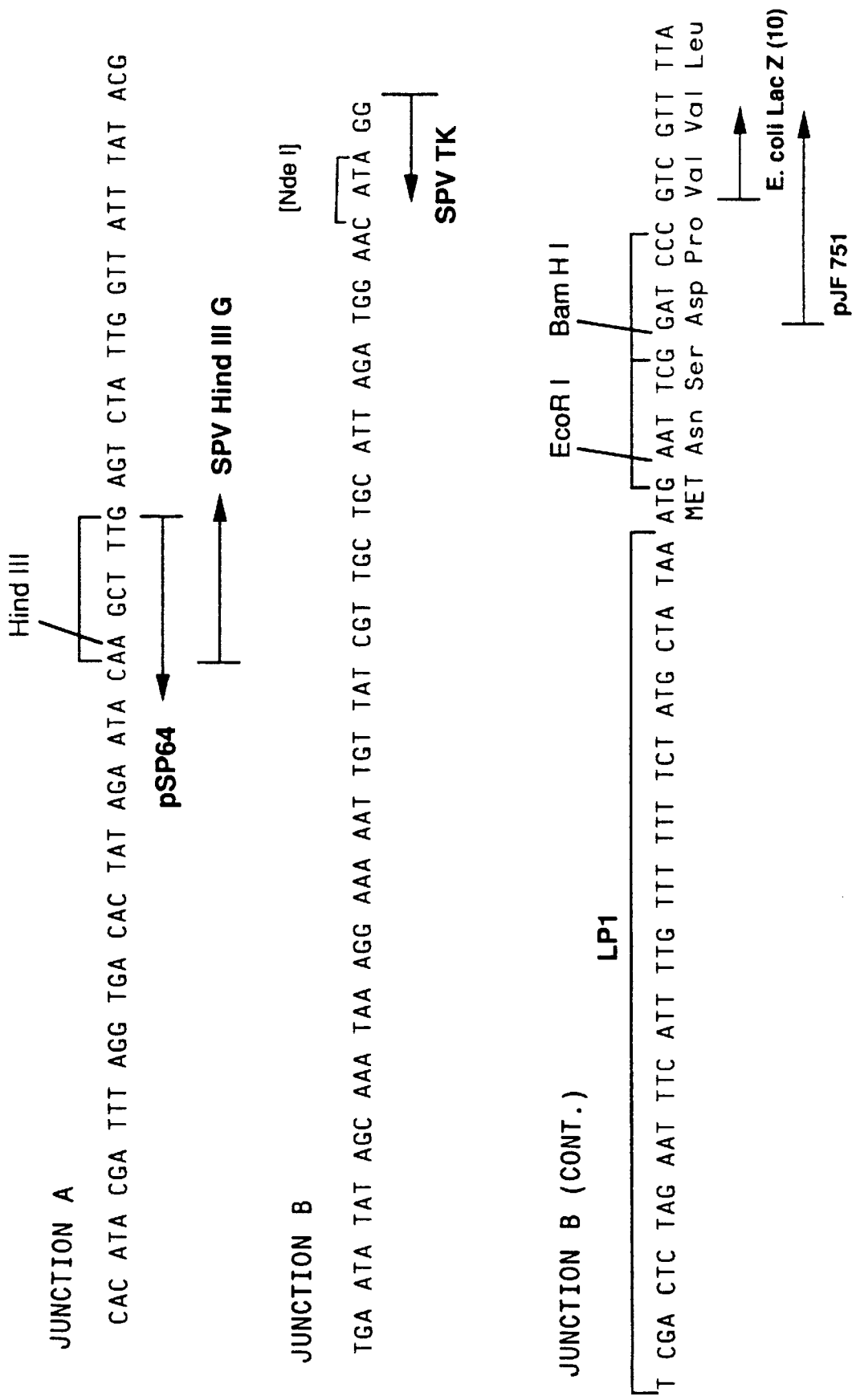
Figure 10A:
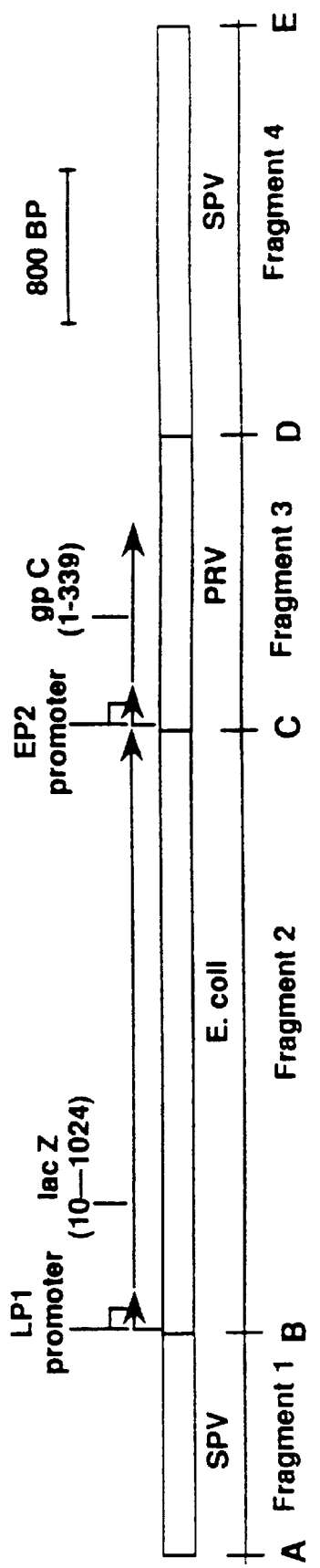
Figure 10B:
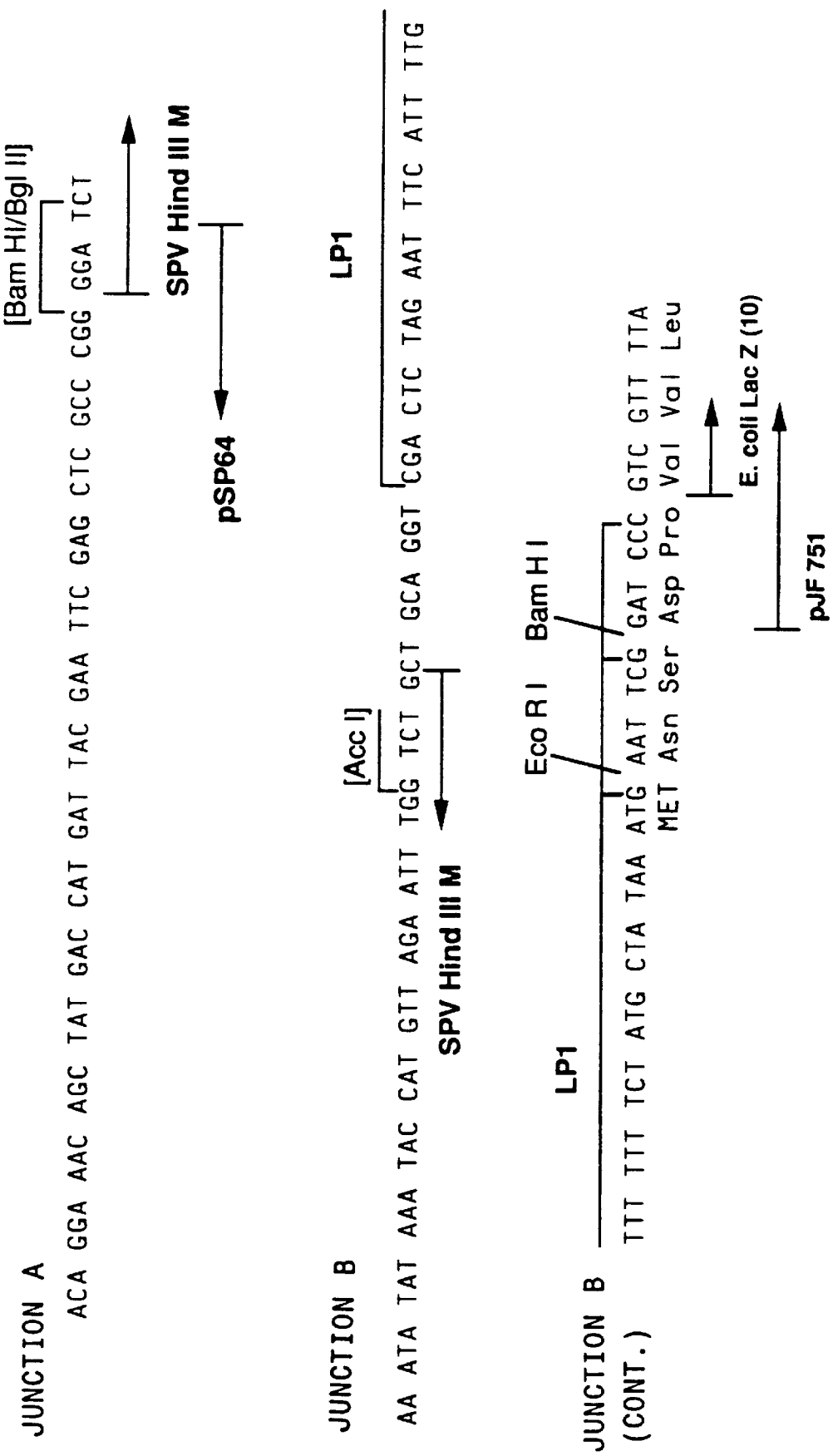
Figure 10C:
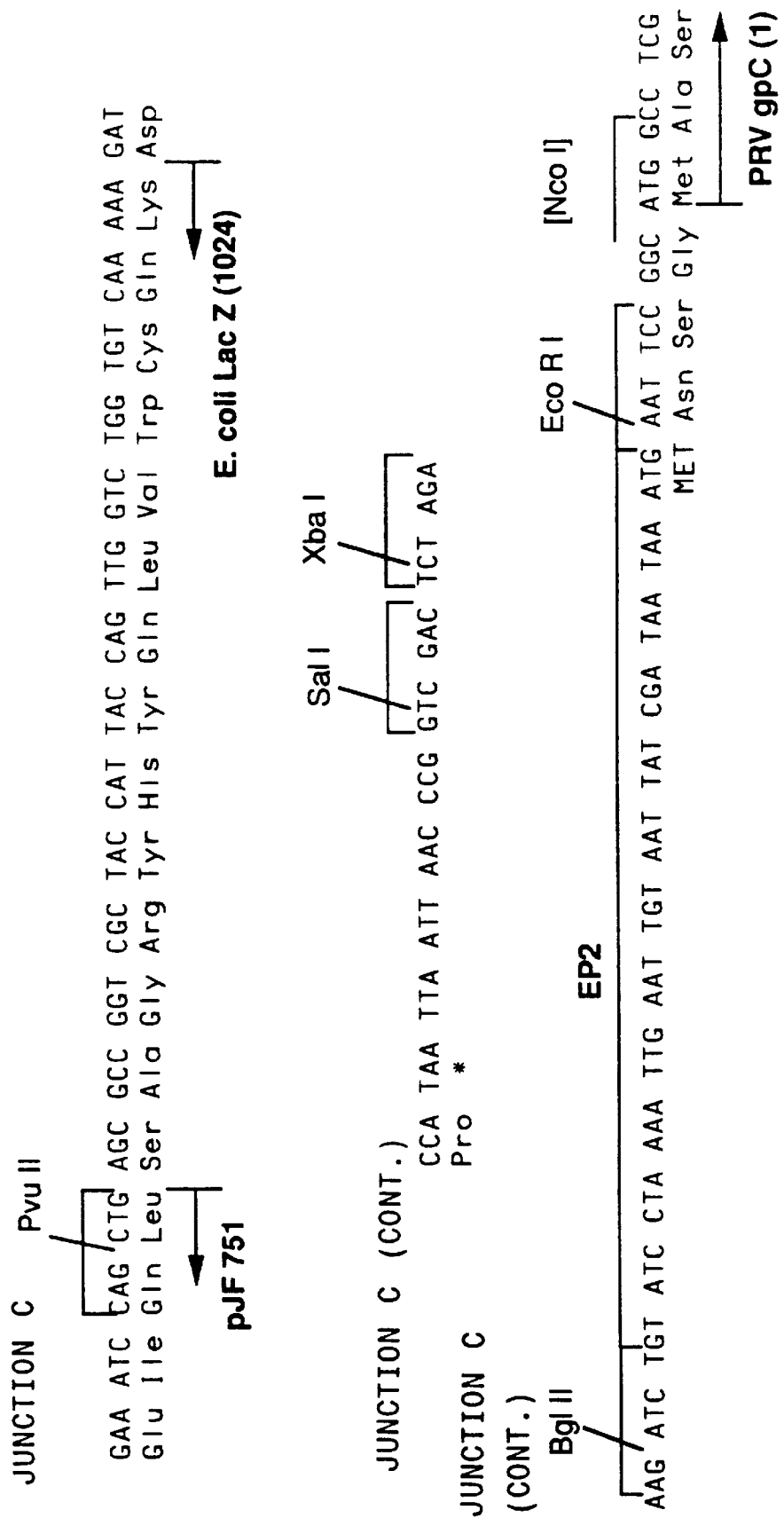
Figure 11A:
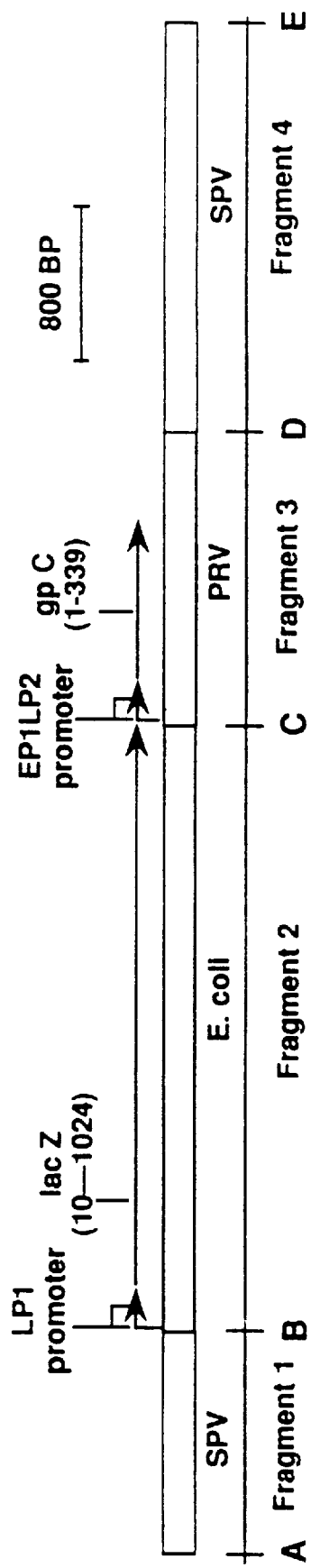
Figure 11C:
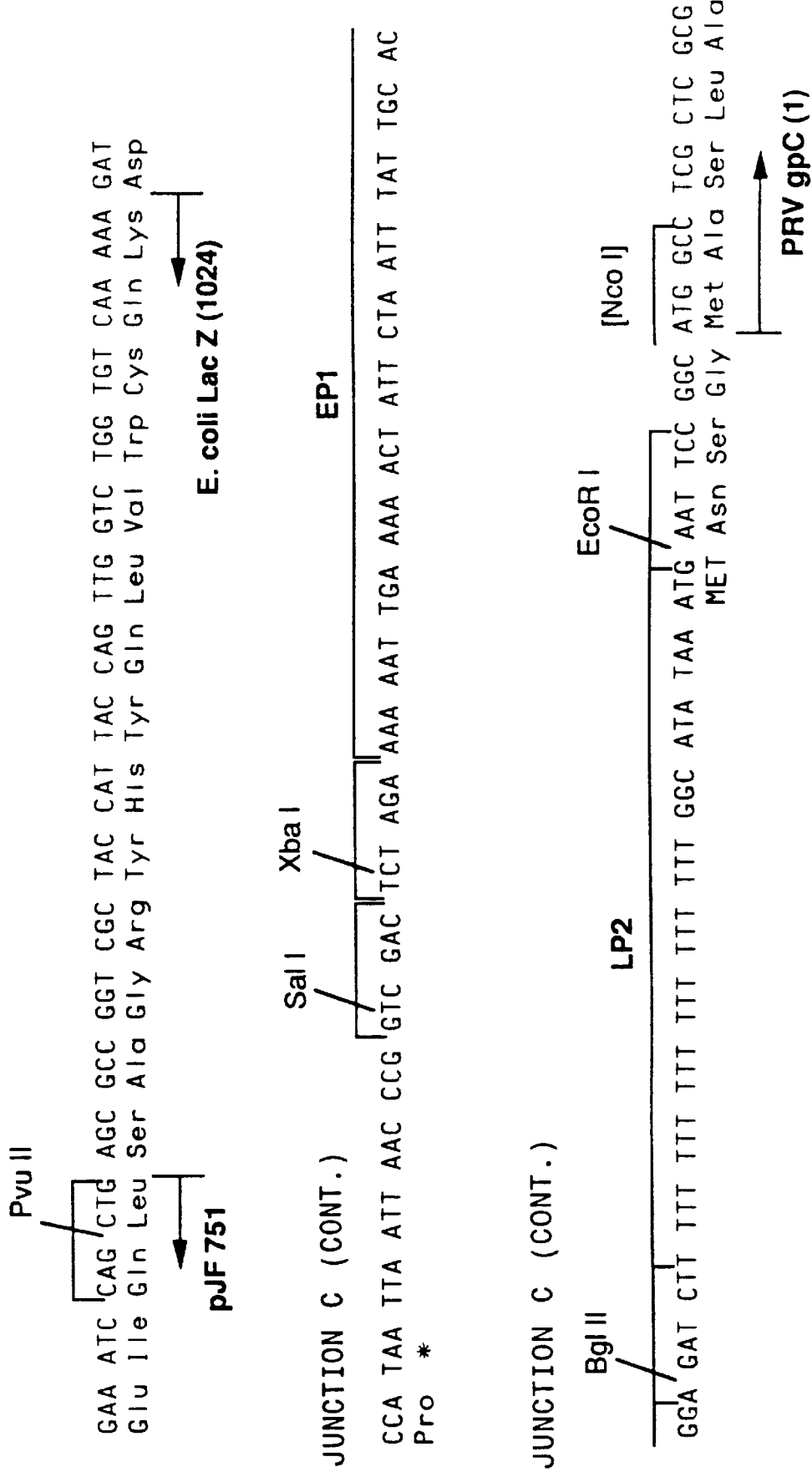
Figure 12A:
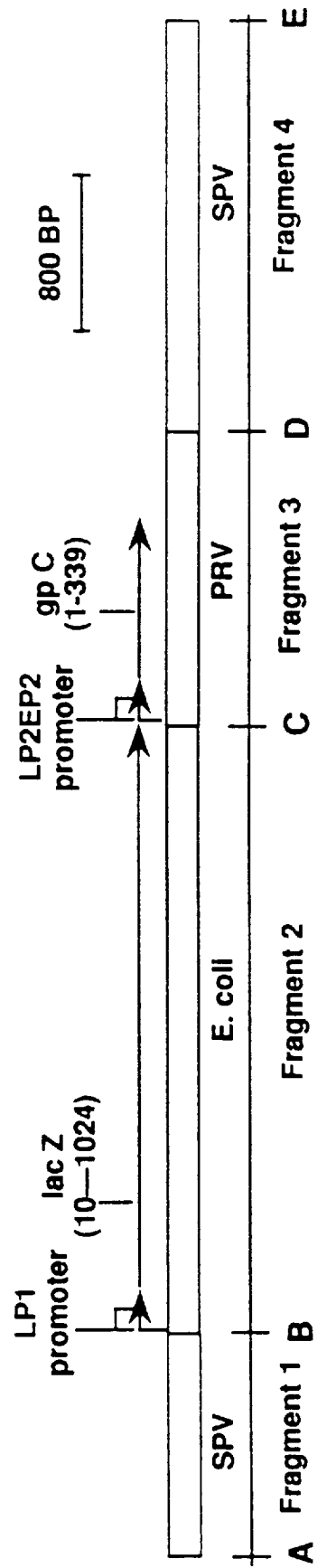
Figure 12B:
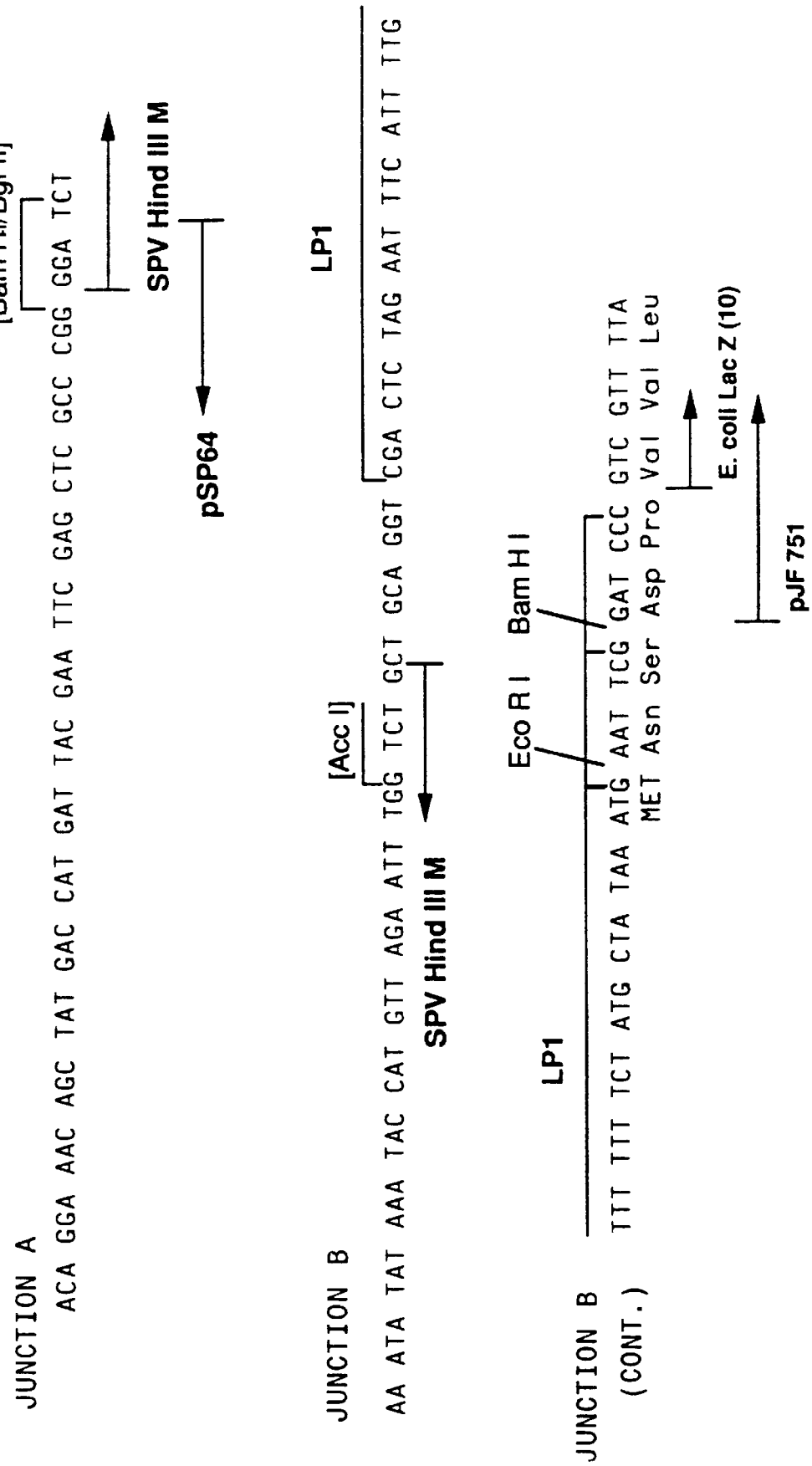
Figure 12C:

HOMOLOGY VECTOR 538-46.26. The plasmid 538-46.26 was constructed for the purpose of inserting foreign DNA into SPV. It incorporates an *E.coli* β-galactosidase (lacZ) marker gene and the Newcastle Disease Virus (NDV) hemagglutinin-Neuraminidase (HN) gene flanked by SPV DNA. Upstream of the foreign genes is an approximately 2156 base pair fragment of SPV DNA. Downstream of the foreign genes is an approximately 1146 base pair fragment of SPV DNA. When this plasmid is used according to the HOMOLOGOUS RECOMBINATION PROCEDURE FOR GENERATING RECOMBINANT SPV a virus containing DNA coding for the foreign genes will result. Note that the β-galactosidase (lacZ) marker gene is under the control of a synthetic late pox promoter (LP1) and the HN gene is under the control of a synthetic early/late pox promoter (EP1LP2). A detailed description of the plasmid is given in FIGS. 8A–8C. It may be constructed utilizing standard recombinant DNA techniques (22 and 30), by joining restriction fragments from the following sources with the synthetic DNA sequences indicated in FIGS. 8A–8C. The plasmid vector is derived from an approximately 2972 base pair HindIII to BamHI restriction fragment of pSP64 (Promega). Fragment 1 is an approximately 2156 base pair HindIII to AccI restriction sub-fragment of the SPV HindIII restriction fragment M (23). Fragment 2 is an approximately 1810 base pair AvaII to NaeI restriction fragment of a NDV HN cDNA clone. The sequence of the HN cDNA clone is given in FIG. 7. The cDNA clone was generated from the B1 strain of NDV using standard cDNA cloning techniques (14). Fragment 3 is an approximately 3006 base pair BamHI to PvuII restriction fragment of plasmid pJF751 (11). Fragment 4 is an approximately 1146 base pair AccI to BglII restriction sub-fragment of the SPV HindIII fragment M (23).

Figure 13A:
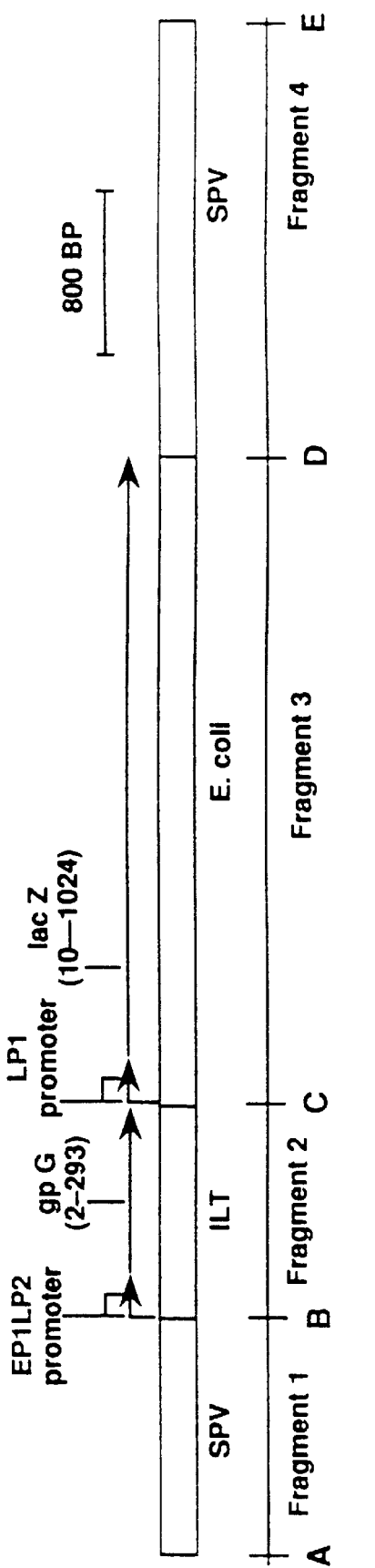
Figure 13B:
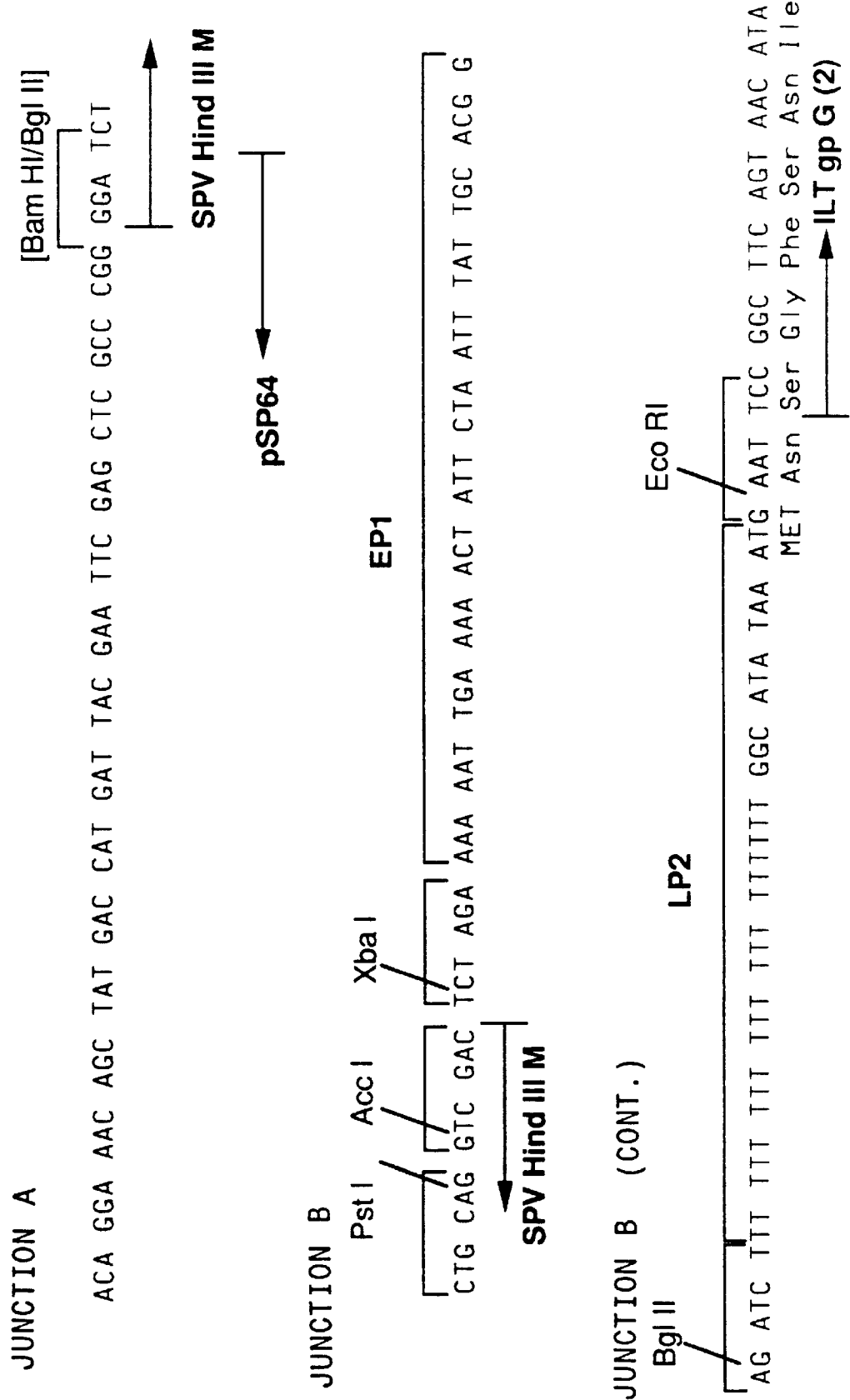
Figure 13C:
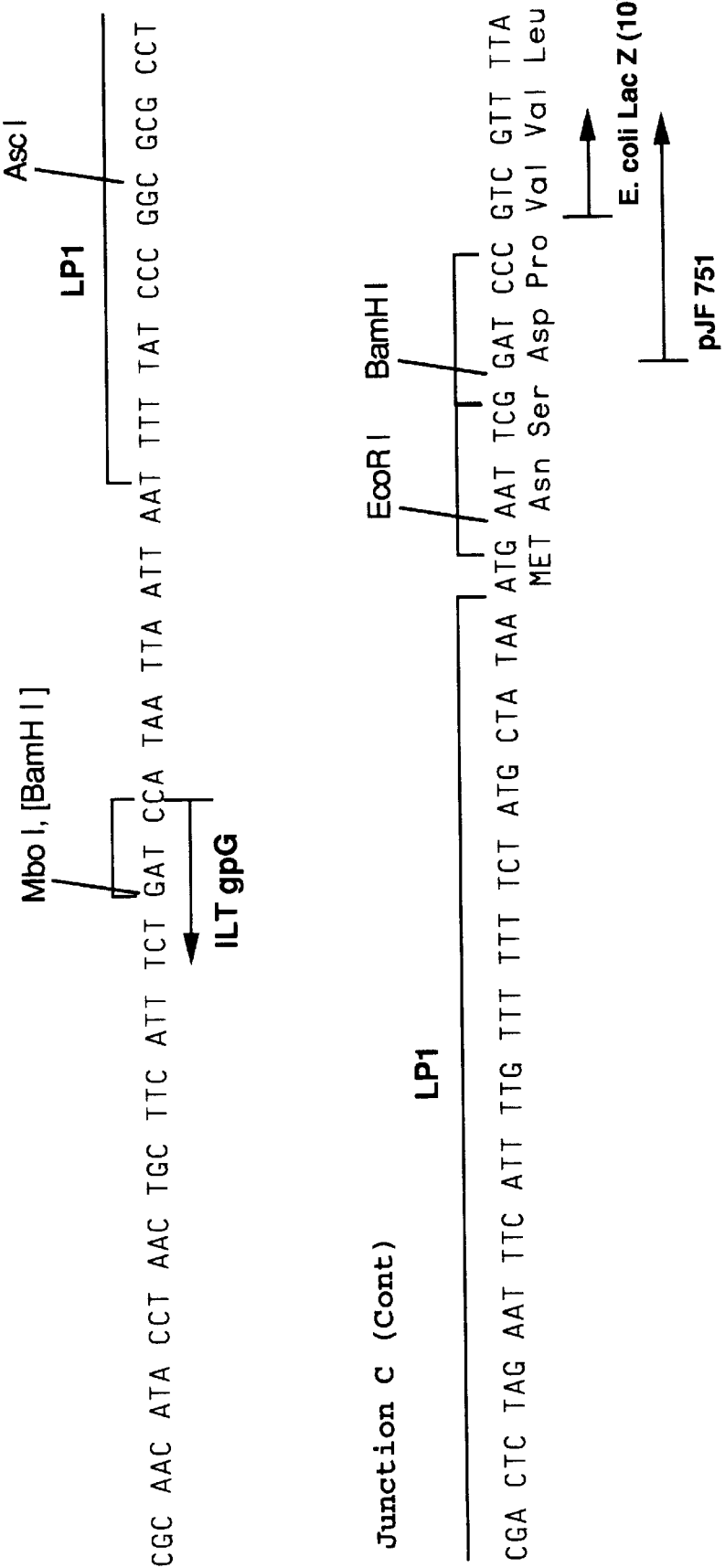
Figure 14B:
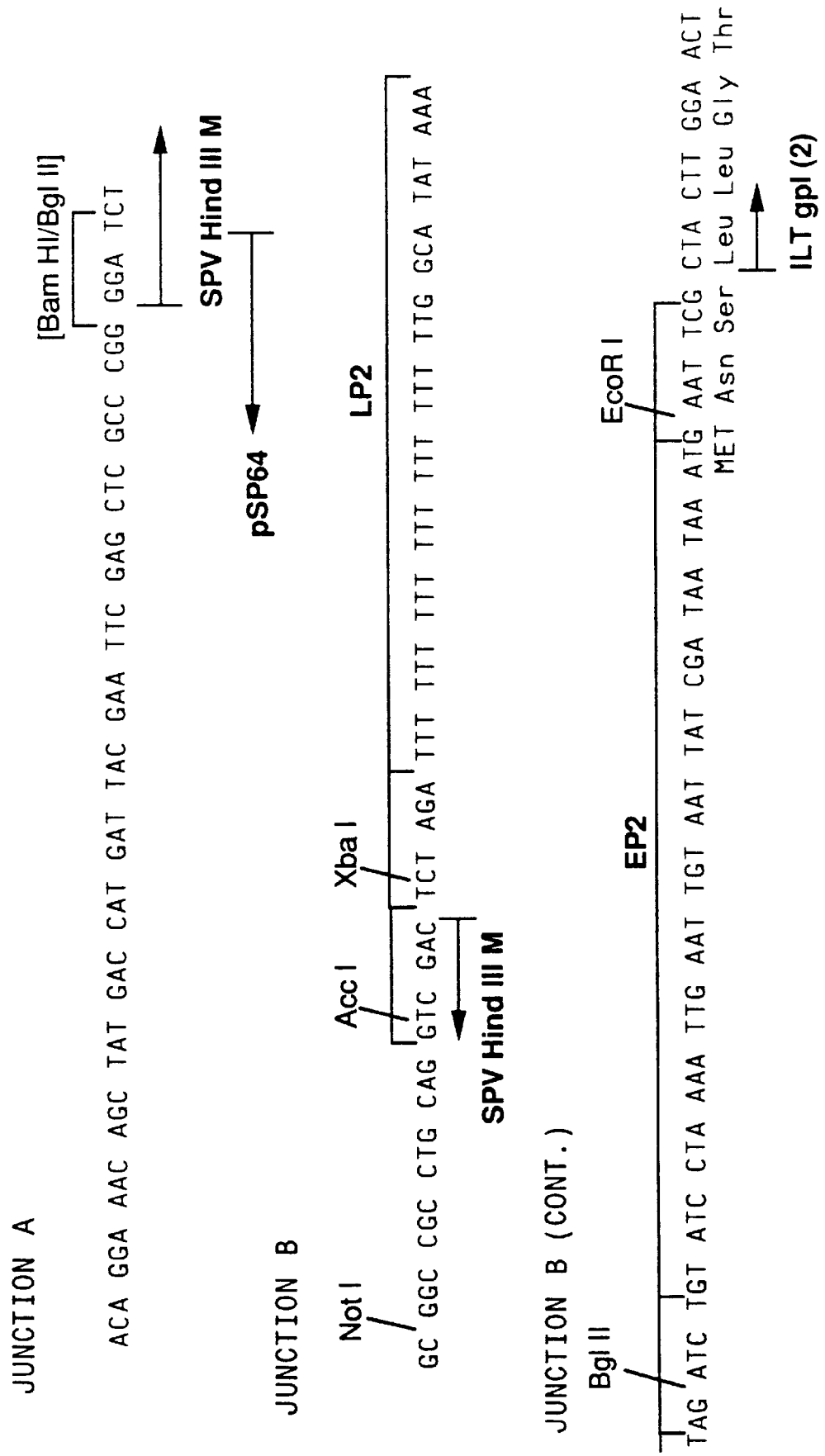
Figure 14C:
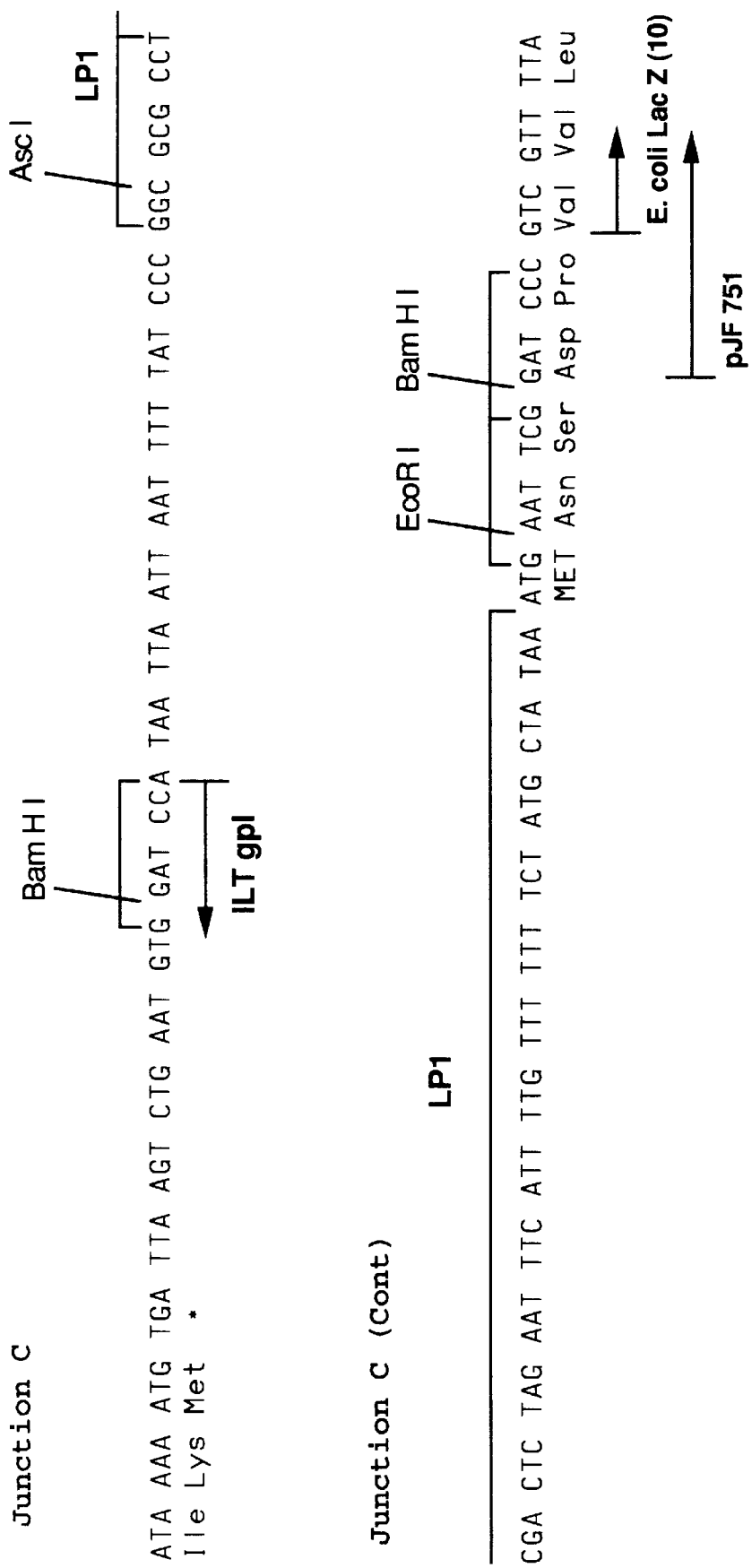
Figure 15A:
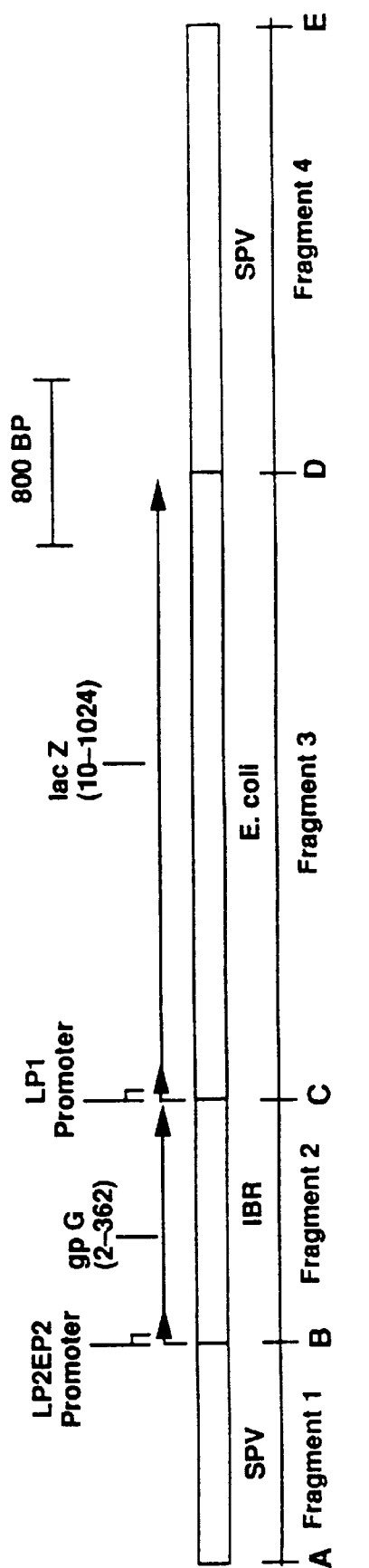
FIGS. 15A–15D Detailed description of Swinepox Virus S-SPV-017 and the DNA insertion in Homology Vector 614-83.18. Diagram showing the orientation of DNA fragments assembled in plasmid 614-83.18. The origin of each fragment is indicated in the table. The sequences located at each of the junctions between fragments is also shown, (SEQ ID NO: 94, 95, 96, 97, 98, 99, 100, 101, 102). The restriction sites used to generate each fragment as well as synthetic linker sequences which are used to join the fragments are described for each junction. The location of several gene coding regions and regulatory elements is also given. The following two conventions are used: numbers in parentheses, ( ), refer to amino acids, and restriction sites in brackets, [ ], indicate the remnants of sites which are destroyed during construction. The following abbreviations are used: swinepox virus (SPV), infectious bovine rhinotracheitis virus (IBR), *Escherichia coli* (*E. coli*), pox synthetic late promoter 1 (LP1), pox synthetic late promoter 2 early promoter 2 (LP2 EP2), glycoprotein G (gpG), polymerase chain reaction (PCR), base pairs (BP).
Figure 15B:
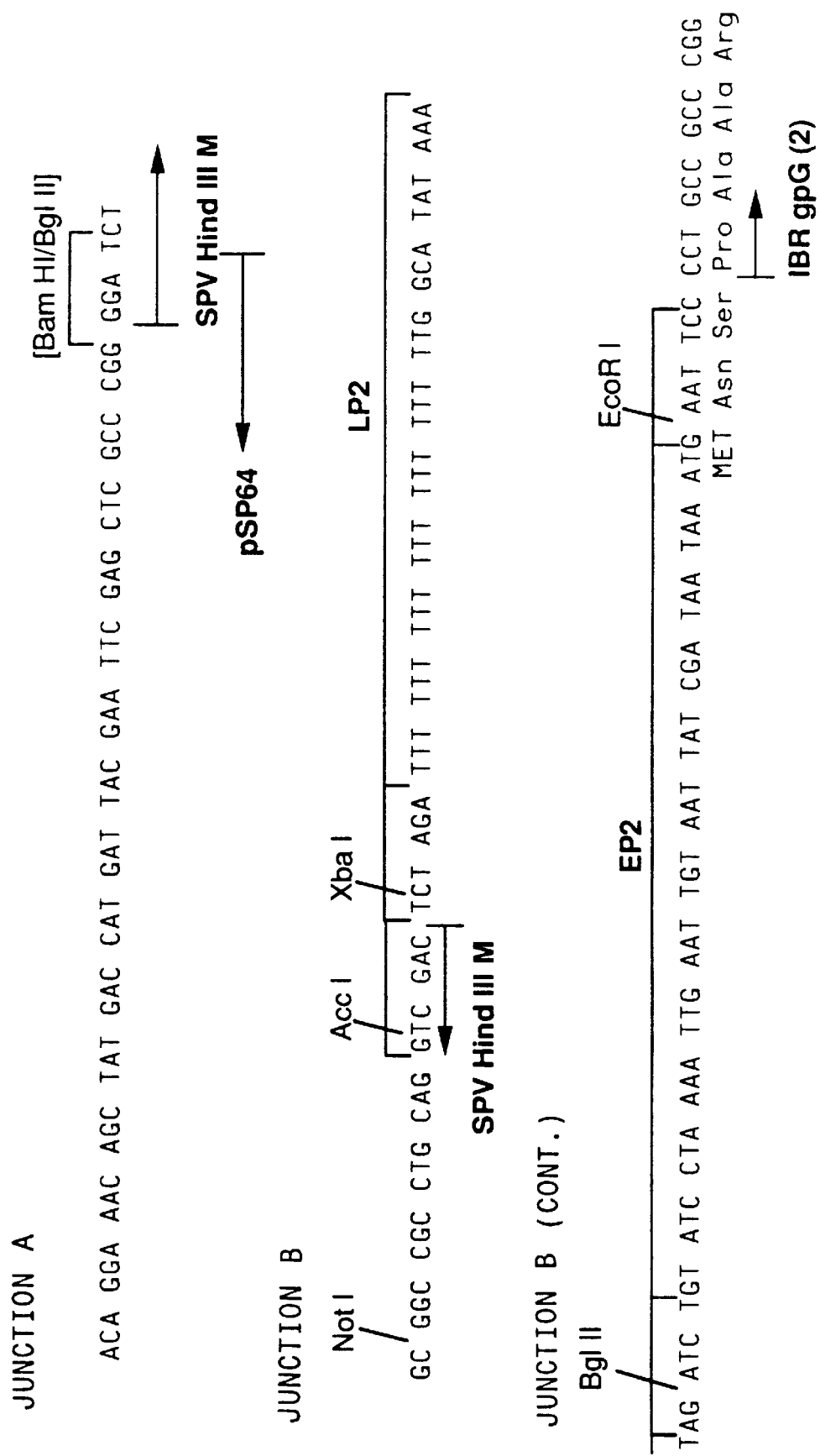
Figure 15C:
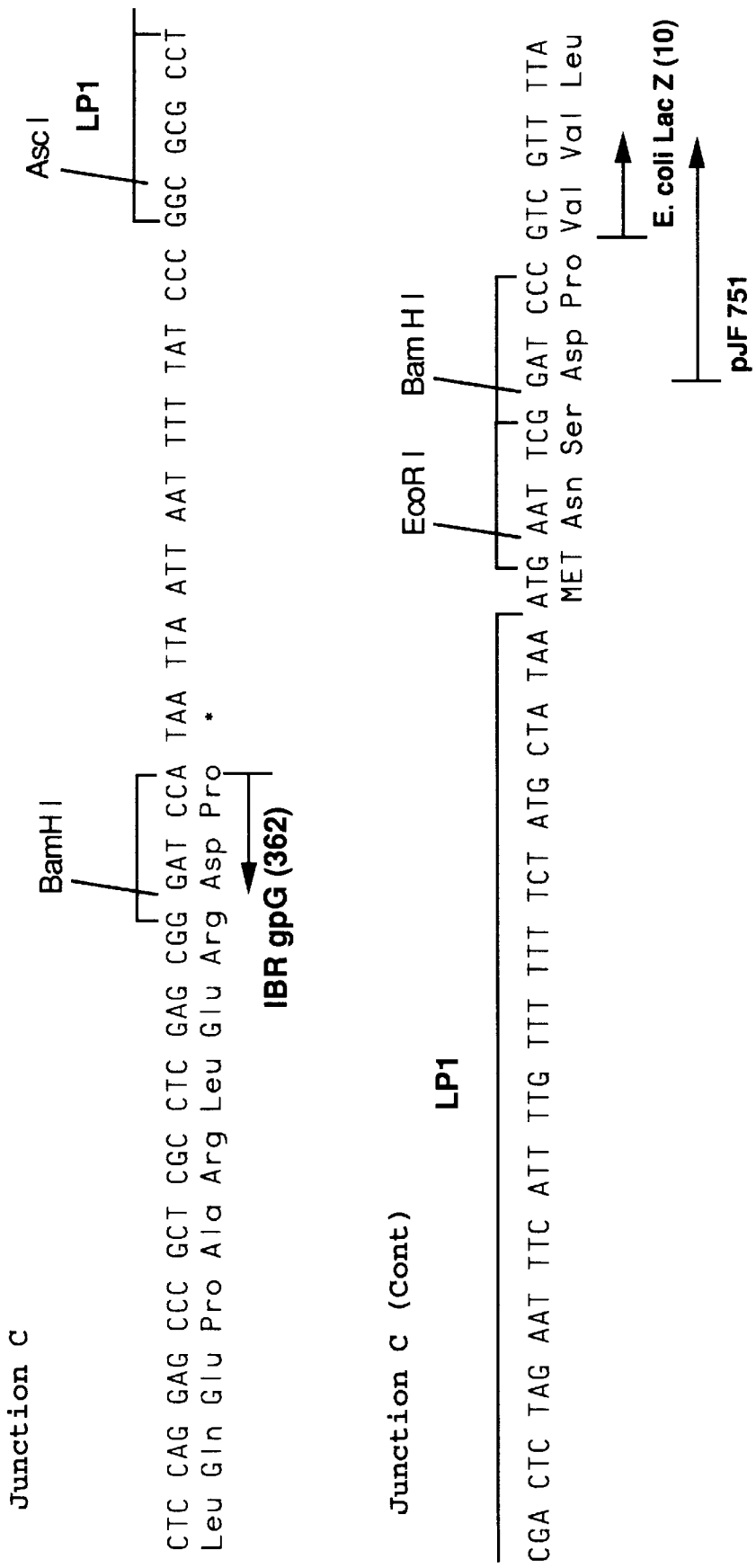
Figure 15D:
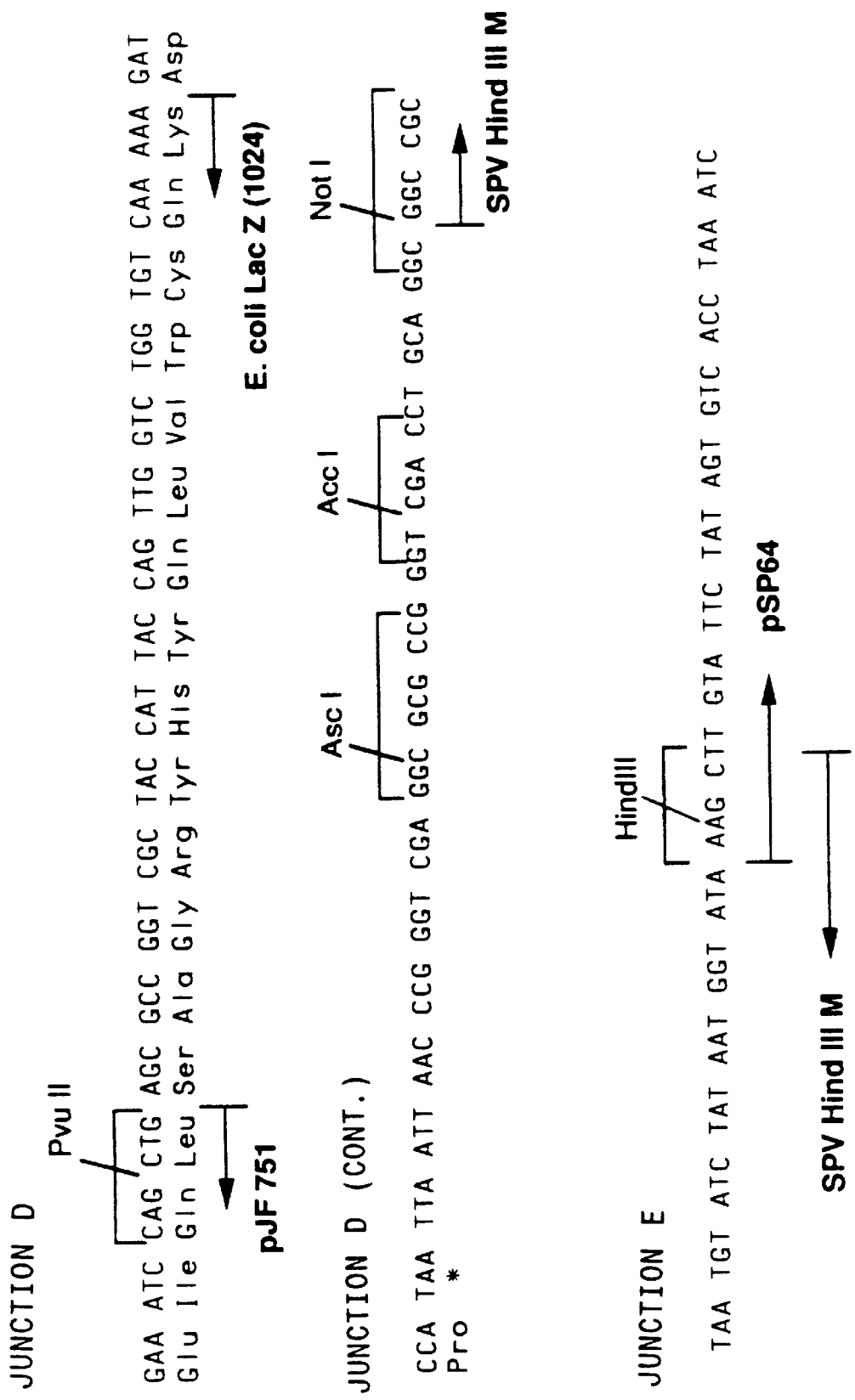

HOMOLOGY VECTOR 599-65.25. The plasmid 599-65.25 was constructed for the purpose of inserting foreign DNA into SPV. It incorporates an *E. coli* B-galactosidase (lacZ) marker gene and the ILT gpG gene flanked by SPV DNA. Upstream of the foreign genes is an approximately 1146 base pair fragment of SPV DNA. Downstream of the foreign genes is an approximately 2156 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the B-galactosidase (lacZ) marker gene is under the control of a synthetic late pox promoter (LP1), and the ILT gpG gene is under the control of a synthetic early/late pox promoter (EP1LP2). A detailed description of the plasmid is given in FIG. 13. It may be constructed utilizing standard recombinant DNA techniques (22, 30), by joining restriction fragments from the following sources with the synthetic DNA sequences indicated in FIG. 13. The plasmid vector is derived from an approximately 2972 base pair HindIII to BamHI restriction fragment of pSP64 (Promega). Fragment 1 is an approximately 1146 base pair BglII to AccI restriction sub-fragment of the SPV HindIII restriction fragment M (23). Fragment 2 is an approximately 1073 base pair EcoRI to MboI fragment. Note that the EcoRI site was introduced by PCR cloning. In this procedure, the primers described below were used with a template consisting of a 2.6 kb Sst I to Asp718I subfragment of a 5.1 kbAsp718I fragment of ILT virus genome. The first primer 91.13 (5'-CCGAATTCCGGCTTCAGTAACATAGGATCG -3') (SEQ ID NO: 103) sits down on the ILT gpG sequence at amino acid 2. It adds an additional asparagine residue between amino acids 1 and 2 and also introduces an EcoRI restriction site. The second primer 91.14 (5'-GTACCCATACTGGTCGTGGC-3') (SEQ ID NO: 104) sits down on the opposite strand at approximately amino acid 196 priming toward the 5' end of the gene. The PCR product is digested with EcoRI and BamHI to produce an approximately 454 base pair fragment. The approximately 485 base pair MboI sub-fragment of ILT Asp718I (5.1 kb) fragment is ligated to the approximately 454 base pair EcoRI to BamHI fragment to generate fragment 2 from EcoRI to MboI which is approximately 939 base pairs (293 amino acids) in length. Fragment 3 is an approximately 3002 base pair BamHI to PvuII restriction fragment of plasmid pJF751 (11). Fragment 4 is an approximately 2156 base pair AccI to HindIII subfragment of the SPV HindIII fragment M. The AccI sites of fragments 1 and 4 have been converted to PstI sites using synthetic DNA linkers.

HOMOLOGY VECTOR 624-20.1C. The plasmid 624-20.1C was constructed for the purpose of inserting foreign DNA into SPV. It incorporates an *E. coli* B-galactosidase (lacZ) marker gene and the ILT gpI gene flanked by SPV DNA. Upstream of the foreign genes is an approximately 1146 base pair fragment of SPV DNA. Downstream of the foreign genes is an approximately 2156 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the B-galactosidase (lacZ) marker gene is under the control of a synthetic late pox promoter (LP1), and the ILT gpI gene is under the control of a synthetic late/early pox promoter (LP2EP2). A detailed description of the plasmid is given in FIGS. 14A–14D. It may be constructed utilizing standard recombinant DNA techniques (22, 30), by joining restriction fragments from the following sources with the synthetic DNA sequences indicated in FIGS. 14A–14D. The plasmid vector is derived from an approximately 2972 base pair HindIII to BamHI restriction fragment of pSP64 (Promega). Fragment 1 is an approximately 1146 base pair Bgl II to AccI restriction sub-fragment of the SPV HindIII restriction fragment M (23). Fragment 2 is an approximately 1090 base pair fragment with EcoRI and BamHI restriction sites at the ends synthesized by PCR cloning and containing the entire amino acid coding sequence of the ILT gpI gene. The ILT gpI gene was synthesized in two separate PCR reactions. In this procedure, the primers described below were used with a template consisting the 8.0 kb ILT Asp 718I fragment. The first primer 103.6 (5'-CCGGAATTCGCTACTT GGAACTCTGG-3') (SEQ ID NO 105) sits down on the ILT gpI sequence at amino acid number 2 and introduces an EcoRI site at the 5' end of the ILT gpI gene. The second primer 103.3 (5'-CATTGTCCCGAGACGGACAG-3') (SEQ ID NO. 106) sits down on the ILT gpI sequence at approximately amino acid 269 on the opposite strand to primer 103.6 and primes toward the 5' end of the gene. The PCR product was digested with EcoRI and BglI (BglI is located approximately at amino acid 209 which is 179 base pairs 5' to primer 2) to yield a fragment 625 base pairs in length corresponding to the 5' end of the ILT gpI gene. The third primer 103.4 (5'-CGCGATCCAACTATCGGTG-3') (SEQ ID NO. 107) sits down on the ILT gpI gene at approximately amino acid 153 priming toward the 3' end of the gene. The fourth primer 103.5 (5' GCGGATCCACAT-TCAG ACTTAATCAC-3') (SEQ ID NO. 108) sits down at the 3' end of the ILT gpI gene 14 base pairs beyond the UGA stop codon, introducing a BamHI restriction site and priming toward the 5' end of the gene. The PCR product is digested with Bgl I (at amino acid 209) and BamHI to yield a fragment 476 base pairs in length corresponding to the 3' end of the ILT gpI gene. Fragment 2 consists of the products of the two PCR reactions ligated together to yield an ILT gpI gene which is a EcoRI to BamHI fragment approximately 1101 base pairs (361 amino acids) in length. Fragment 3 is an approximately 3002 base pair BamHI to PvuII restriction fragment of plasmid pJF751 (11). Fragment 4 is an approximately 2156 base pair AccI to HindIII subfragment of the SPV HindIII fragment M. The AccI sites in fragments 1 and 4 were converted to unique NotI sites using NotI linkers.

HOMOLOGY VECTOR 614-83.18. The plasmid 614-83.18 was constructed for the purpose of inserting foreign DNA into SPV. It incorporates an *E. coli* B-galactosidase (lacZ) marker gene and the IBR gpG gene flanked by SPV DNA. Upstream of the foreign genes is an approximately 1146 base pair fragment of SPV DNA. Downstream of the foreign genes is an approximately 2156 base pair fragment of SPV DNA. When the plasmid is used according to the HOMOLOGOUS RECOMBINATION PROCEDURE FOR GENERATING RECOMBINANT SPV, a virus containing DNA coding for the foreign genes will result. Note that the B-galactosidase (lacZ) marker gene is under the control of a synthetic late pox promoter (LP1), and the IBR gG gene is under the control of a synthetic late/early pox promoter (LP2EP2). A detailed description of the plasmid is given in FIGS. 15A–15D. It may be constructed utilizing standard recombinant DNA techniques (22, 30), by joining restriction fragments from the following sources with the synthetic DNA sequences indicated in FIGS. 15A–15D. The plasmid vector is derived from an approximately 2972 base pair HindIII to BamHI restriction fragment of pSP64 (Promega). Fragment 1 is an approximately 1146 base pair BglII to AccI restriction sub-fragment of the SPV HindIII restriction fragment M (23). Fragment 2 is an approximately 1085 base pair fragment synthesized by PCR cloning with EcoRI and BamHI restriction sites at the ends and containing the amino acid coding sequence from amino acids 2 to 362 of the IBR gpG gene. In the PCR cloning procedure, the primers described below were used with a template consisting of the IBR-000 virus (Cooper strain). The first primer 106.9 (5'-ATGAATTCCCCTGCCGCCCGGACCGGCACC-3') (SEQ ID NO. 109) sits down on the IBR gpG sequence at amino acid number 1 and introduces an EcoRI site at the 5' end of the IBR gpG gene and two additional amino acids between amino acids 1 and 2. The second primer 106.8 (5'-CATGGATCCCGCTCGAGGCGAGCGGGCTCC-3') (SEQ ID NO. 110) sits down on the IBR gpG sequence at approximately amino acid 362 on the opposite strand to primer 1 and primes synthesis toward the 5' end of the IBR gpG gene. Fragment 2 was generated by digesting the PCR product with EcoRI and BamHI to yield a fragment 1085 base pairs in length corresponding to the amino terminal 362 amino acids (approximately 80%) of the IBR gpG gene. Fragment 3 is an approximately 3002 base pair BamHI to PvuII restriction fragment of plasmid pJF751 (11). Fragment 4 is an approximately 2156 base pair AccI to HindIII subfragment of the SPV HindIII fragment M. The AccI sites in fragments 1 and 4 were converted to unique NotI sites using NotI linkers.

HOMOLOGY VECTOR FOR CONSTRUCTING S-SPV-019 (LacZ/IBR gpE HOMOLOGY VECTOR):

This lacZ/IBR gpE homology vector is used to insert foreign DNA into SPV. It incorporates an *E. coli* B-galactosidase (lacZ) marker gene and the IBR gpE gene flanked by SPV DNA. When this plasmid is used according to the HOMOLOGOUS RECOMBINATION PROCEDURE FOR GENERATING RECOMBINANT SPV a virus containing DNA coding for the foreign genes will result. Note that the B-galactosidase (lacZ) marker gene is under the control of a synthetic late pox promoter and the gpE gene is under the control of a synthetic late/early pox promoter. The homology vector may be constructed utilizing standard recombinant DNA techniques (22 and 30), by joining restriction fragments from the following sources with the appropriate synthetic DNA sequences. The plasmid vector is derived from an approximately 2972 base pair HindIII to BamHI restriction fragment of pSP64 (Promega). The upstream SPV homology is an approximately 1146 base pair BglIII to AccI restriction sub-fragment of the SPV HindIII fragment M (23). The IBR gE gene is an approximately 1888 base pair fragment synthesized by PCR cloning with EcoRI and BamHI ends. In the PCR cloning procedure, the primers described below were used with a template consisting of the IBR-000 VIRUS (Cooper strain). The first primer 4/93.17DR (5'-CTGGTTCGGCCCAGAATTCTATGGGT CTCGCGCGGCTCGTGG-3' (SEQ ID NO. 111) sits down on the IBR gpE gene at amino acid number 1 and introduces an EcoRI site at the 5' end of the IBR gpE gene and adds two additional amino acids at the amino terminus of the protein. The second primer 4/93.18DR (5'-CTCGCTCG CCCAGGATCCCTAGCGGAGGATGGACTTGAGTCG-3') (SEQ ID NO. 112) sits down on the IBR gpE sequence at approximately amino acid 648 on the opposite strand to primer 1 and primes synthesis toward the 5' end of the IBR gpE gene. The lacZ promoter and marker gene is identical to the one used in plasmid 520-17.5. The downstream SPV homology is an approximately 2156 base pair AccI to HindIII restriction sub-fragment of the SPV HindIII restriction fragment M (23). The AccI site in the SPV homology vector is converted to a unique XbaI site.

HOMOLOGY VECTOR FOR CONSTRUCTING S-SPV-018 (LacZ/PRV gpE HOMOLOGY VECTOR):

This homology vector is constructed for the purpose of inserting foreign DNA into SPV. It incorporates an *E. coli* B-galactosidase (lacZ) marker gene and the PRV gpE gene flanked by SPV DNA. Upstream of the foreign genes is an approximately 1146 base pair fragment of SPV DNA. Downstream of the foreign genes is an approximately 2156 base pair fragment of SPV DNA. When the plasmid is used according to the HOMOLOGOUS RECOMBINATION PROCEDURE FOR GENERATING RECOMBINANT SPV, a virus containing the DNA coding for the foreign genes results. Note that the B-galactosidase (lacZ) marker gene is under the control of a synthetic late pox promoter (LP1), and the PRV gpE gene is under the control of a synthetic early/late pox promoter (EP1LP2). The homology vector is constructed utilizing standard recombinant DNA techniques (22,30), by joining restriction fragments from the following sources with synthetic DNA sequences. The plasmid vector is derived from an approximately 2972 base pair HindIII to BamHI restriction fragment pSP64 (Promega). Fragment 1 is an approximately 1146 base pair BglII to AccI restriction sub-fragment of the SPV HindIII restriction fragment M (23). Fragment 2 is the lacZ promoter and marker gene which is identical to the one used in plasmid 520-17.5. Fragment 3 is an approximately 2484 base pair DraI to MluI sub-fragment of PRV derived from the PRV BamHI #7 DNA fragment. The DraI site is converted to an EcoRI site through the use of a synthetic DNA linker. The DraI site sits 45 base pairs upstream of the natural gpE start codon and extends the open reading frame at the amino terminus of the protein for 15 amino acids. The synthetic pox promoter/EcoRI DNA linker contributes another 4 amino acids. Therefore, the engineered gpE gene contains 19 additional amino acids fused to the amino terminus of gpE. The nineteen amino acids are Met-Asn-Ser-Gly-Asn-Leu-Gly-Thr-Pro-Ala-Ser-Leu-Ala-His-Thr-Gly-Val-Glu-Thr. Fragment 4 is an approximately 2156 base pair AccI to HindIII subfragment of the SPV HindIII fragment M (23). The AccI sites of fragments 1 and 4 are converted to PstI sites using synthetic DNA linkers.

HOMOLOGY VECTOR 520-90.15. The plasmid 520-90.15 was constructed for the purpose of inserting foreign DNA into SPV. It contains a unique NdeI restriction enzyme site into which foreign DNA may be inserted. When a plasmid, containing a foreign DNA insert at the NdeI site, is used according to the HOMOLOGOUS RECOMBINATION PROCEDURE FOR GENERATING RECOMBINANT SPV a virus containing the foreign DNA will result. Plasmid 520-90.15 was constructed utilizing standard recombinant DNA techniques (22 and 30), by joining two restriction fragments from the following sources. The first fragment is an approximately 2972 base pair HindIII to BamHI restriction fragment of pSP64 (Promega). The second fragment is an approximately 1700 base pair HindIII to BamHI restriction subfragment of the SPV HindIII restriction fragment G (23).

EXAMPLES

Example 1

Homology Vector 515-85.1. The homology vector 515-85.1 is a plasmid useful for the insertion of foreign DNA into SPV. Plasmid 515-85.1 contains a unique AccI restriction site into which foreign DNA may be cloned. A plasmid containing such a foreign DNA insert may be used according to the HOMOLOGOUS RECOMBINATION PROCEDURE FOR GENERATING RECOMBINANT SPV to generate a SPV containing the foreign DNA. For this procedure to be successful it is important that the insertion site (AccI) be in a region non-essential to the replication of the SPV and that the site be flanked with swinepox virus DNA appropriate for mediating homologous recombination between virus and plasmid DNAs. We have demonstrated that the AccI site in homology vector 515-85.1 may be used to insert foreign DNA into at least three recombinant SPV (see examples 2–4).

In order to define an appropriate insertion site, a library of SPV HindIII restriction fragments was generated. Several of these restriction fragments (HindIII fragments G, J, and M see FIG. 1) were subjected to restriction mapping analysis. Two restriction sites were identified in each fragment as potential insertion sites. These sites included HpaI and NruI in fragment G, BalI and XbaI in fragment J, and AccI and PstI in fragment M. A β-galactosidase (lacZ) marker gene was inserted in each of the potential sites. The resulting plasmids were utilized in the HOMOLOGOUS RECOMBINATION PROCEDURE FOR GENERATING RECOMBINANT SPV. The generation of recombinant virus was determined by the SCREEN FOR RECOMBINANT SPV EXPRESSING β-GALACTOSIDASE ASSAYS. Four of the six sites were found to generate recombinant virus, however the ability of each of these viruses to be purified away from the parental SPV varied greatly. In one case virus could not be purified above the level of 1%, in another case virus could not be purified above the level of 50%, and in a third case virus could not be purified above the level of 90%. The inability to purify these viruses indicates instability at the insertion site. This makes the corresponding sites inappropriate for insertion of foreign DNA. However the insertion at one site, the AccI site of Homology vector 515-85.1, resulted in a virus which was easily purified to 100% (see example 2), clearly defining an appropriate site for the insertion of foreign DNA.

Figure 3A:
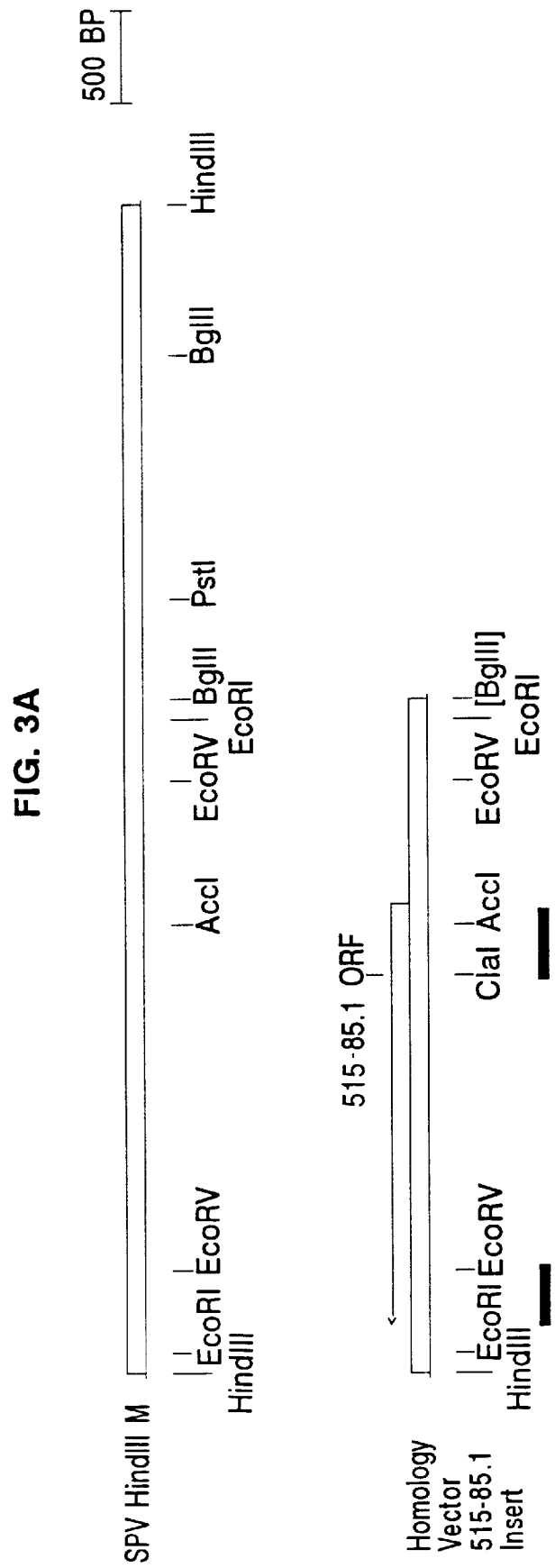

The homology vector 515-85.1 was further characterized by DNA sequence analysis. Two regions of the homology vector were sequenced. The first region covers a 599 base pair sequence which flanks the unique AccI site (see FIGS. 2A–2B). The second region covers the 899 base pairs upstream of the unique HindIII site (see FIGS. 2A–2B). The sequence of the first region codes for an open reading frame (ORF) which shows homology to amino acids 1 to 115 of the vaccinia virus (VV) 01L open reading frame identified by Goebel et al, 1990 (see FIGS. 3A–3B). The sequence of the second region codes for an open reading frame which shows homology to amino acids 568 to 666 of the same vaccinia virus 01L open reading frame (see FIGS. 3A–3B). These data suggest that the AccI site interrupts the presumptive VV 01L-like ORF at approximately amino acid 41, suggesting that this ORF codes for a gene non-essential for SPV replication. Goebel et al. suggest that the VV 01L ORF contains a leucine zipper motif characteristic of certain eukaryotic transcriptional regulatory proteins, however they indicate that it is not known whether this gene is essential for virus replication.

The DNA sequence located upstream of the VV 01L-like ORF (see FIG. 2A) would be expected to contain a swinepox viral promoter. This swinepox viral promoter will be useful as the control element of foreign DNA introduced into the swinepox genome.

Example 2

S-SPV-003

S-SPV-003 is a swinepox virus that expresses a foreign gene. The gene for E.coli β-galactosidase (lacZ gene) was inserted into the SPV 515-85.1 ORF. The foreign gene (lacZ) is under the control of a synthetic early/late promoter (EP1LP2).

S-SPV-003 was derived from S-SPV-001 (Kasza strain). This was accomplished utilizing the homology vector 520-17.5 (see *Materials and Methods*) and virus S-SPV-001 in the HOMOLOGOUS RECOMBINATION PROCEDURE FOR GENERATING RECOMBINANT SPV. The transfection stock was screened by the SCREEN FOR RECOMBI- NANT SPV EXPRESSING β-GALACTOSIDASE (BLUOGAL AND CPRG ASSAYS). The final result of red plaque purification was the recombinant virus designated S-SPV-003. This virus was assayed for β-galactosidase expression, purity, and insert stability by multiple passages monitored by the blue plaque assay as described in *Materials and Methods*. After the initial three rounds of purification, all plaques observed were blue indicating that the virus was pure, stable and expressing the foreign gene. The assays described here were carried out in VERO cells as well as EMSK cells, indicating that VERO cells would be a suitable substrate for the production of SPV recombinant vaccines. S-SPV-003 has been deposited with the ATCC under Accession No. VR 2335.

Example 3

S-SPV-008

S-SPV-008 is a swinepox virus that expresses at least two foreign genes. The gene for *E. coli* β-galactosidase (lacZ gene) and the gene for pseudorabies virus (PRV) g50 (gpD) (26) were inserted into the SPV 515-85.1 ORF. The lacZ gene is under the control of a synthetic late promoter (LP1) and the g50 (gp)D gene is under the control of a synthetic early/late promoter (EP1LP2).

S-SPV-008 was derived from S-SPV-001 (Kasza strain). This was accomplished utilizing the homology vector 538-46.16 (see *Materials and Methods*) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-GALACTOSIDASE (BLUOGAL AND CPRG ASSAYS). The final result of red plaque purification was the recombinant virus designated S-SPV-008. This virus was assayed for β-galactosidase expression, purity, and insert stability by multiple passages monitored by the blue plaque assay as described in *Materials and Methods*. After the initial three rounds of purification, all plaques observed were blue indicating that the virus was pure, stable and expressing the marker gene.

S-SPV-008 was assayed for expression of PRV specific antigens using the BLACK PLAQUE SCREEN FOR FOREIGN GENE EXPRESSION IN RECOMBINANT SPV. Swine anti-PRV serum was shown to react specifically with S-SPV-008 plaques and not with S-SPV-009 negative control plaques. All S-SPV-008 observed plaques reacted with the swine antiserum indicating that the virus was stably expressing the PRV foreign gene. The black plaque assay was also performed on unfixed monolayers. The SPV plaques on the unfixed monolayers also exhibited specific reactivity with swine anti-PRV serum indicating that the PRV antigen is expressed on the infected cell surface.

To confirm the expression of the PRV g50 (gpD) gene product, cells were infected with SPV and samples of infected cell lysates were subjected to SDS-polyacrylamide gel electrophoresis. The gel was blotted and analyzed using the WESTERN BLOTTING PROCEDURE. The swine anti-PRV serum was used to detect expression of PRV specific proteins. As shown in FIG. 6, the lysate from S-SPV-008 infected cells exhibits a specific band of approximately 48 kd, the reported size of PRV g50 (gpD) (35).

PRV g50 (gpD) is the g50 (gpD) homologue of HSV-1 (26). Several investigators have shown that VV expressing HSV-1 g50 (gpD) will protect mice against challenge with HSV-1 (6 and 34). Therefore the S-SPV-008 should be valuable as a vaccine to protect swine against PRV disease.

It is anticipated that several other PRV glycoproteins will be useful in the creation of recombinant swinepox vaccines to protect against PRV disease. These PRV glycoproteins include gpII (28), gpIII (27), and gpH (19). The PRV gpIII coding region has been engineered behind several synthetic pox promoters. The techniques utilized for the creation of S-SPV-008 will be used to create recombinant swinepox viruses expressing all four of these PRV glycoprotein genes. Such recombinant swinepox viruses will be useful as vaccines against PRV disease. Since the PRV vaccines described here do not express PRV gpX or gpI, they would be compatible with current PRV diagnostic tests (gX HerdChek®, gI HerdChek® and ClinEase®) which are utilized to distinguish vaccinated animals from infected animals. S-SPV-008 has been deposited with the ATCC under Accession No. VR 2339.

Example 4

S-SPV-011

S-SPV-011 is a swinepox virus that expresses at least two foreign genes. The gene for *E. coli* B-galactosidase (lacZ) and the gene for pseudorabies virus gIII (gpC) were inserted into the unique PstI restriction site (PstI linkers inserted into a unique AccI site) of the homology vector 570-33.32. The lac Z gene is under the control of the synthetic late promoter (LP1) and the PRV gIII (gpC) gene is under the control of the synthetic early promoter (EP2).

S-SPV-011 was derived from S-SPV-001 (Kasza Strain). This was accomplished utilizing the homology vector 570-91.21 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING B-GALACTOSIDASE (BLUOGAL AND CPRG ASSAYS). The final result of red plaque purification was the recombinant virus designated S-SPV-011. This virus was assayed for B-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-011 was assayed for expression of PRV specific antigens using the BLACK PLAQUE SCREEN FOR FOREIGN GENE EXPRESSION IN RECOMBINANT SPV. Polyclonal goat anti-PRV gIII (gpC) antibody was shown to react specifically with S-SPV-011 plaques and not with S-SPV-001 negative control plaques. All S-SPV-011 observed plaques reacted with the swine anti-PRV serum indicating that the virus was stably expressing the PRV foreign gene. The assays described here were carried out in EMSK cells, indicating that EMSK cells would be a suitable substrate for the production of SPV recombinant vaccines.

To confirm the expression of the PRV gIII (gpC) gene product, cells were infected with SPV and samples of infected cell lysates were subjected to SDS-polyacrylamide gel electrophoresis. The gel was blotted and analyzed using the WESTERN BLOTTING PROCEDURE. Polyclonal goat anti-PRV gIII (gpC) antibody was used to detect expression of PRV specific proteins. As shown in FIG. 16, the lysate from S-SPV-011 infected cells exhibits a specific band of approximately 92 kd, the reported size of PRV gIII (gpC) (37).

Recombinant-expressed PRV gIII (gpC) has been shown to elicit a significant immune response in mice and swine (37, 38). Furthermore, when gIII (gpC) is coexpressed with gII (gpB) or g50 (gpD), significant protection from challenge with virulent PRV is obtained (39). Therefore S-SPV011 should be valuable as a vaccine to protect swine against PRV disease. Since the PRV vaccines described here do not express PRV gpX or gpI, they would be compatible

Example 5

S-SPV-012

S-SPV-012 is a swinepox virus that expresses at least two foreign genes. The gene for *E. coli* B-galactosidase (lacZ) and the gene for pseudorabies virus gIII (gpC) were inserted into the unique PstI restriction site (PstI linkers inserted into a unique AccI site) of the homology vector 570-33.32. The lacZ gene is under the control of the synthetic late promoter (LP1) and the PRV gIII (gpC) gene is under the control of the synthetic early late promoter (EP1LP2).

S-SPV-012 was derived from S-SPV-001 (Kasza Strain). This was accomplished utilizing the homology vector 570-91.41 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING B-GALACTOSIDASE (BLUOGAL AND CPRG ASSAYS). The final result of red plaque purification was the recombinant virus designated S-SPV-012. This virus was assayed for B-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-012 was assayed for expression of PRV specific antigens using the BLACK PLAQUE SCREEN FOR FOREIGN GENE EXPRESSION IN RECOMBINANT SPV. Polyclonal goat anti-PRV gIII (gpC) antibody was shown to react specifically with S-SPV-012 plaques and not with S-SPV-001 negative control plaques. All S-SPV-012 observed plaques reacted with the swine anti-PRV serum, indicating that the virus was stably expressing the PRV foreign gene. The assays described here were carried out in EMSK and VERO cells, indicating that EMSK cells would be a suitable substrate for the production of SPV recombinant vaccines.

To confirm the expression of the PRV gIII (gpC) gene product, cells were infected with S-SPV-012 and samples of infected cell lysates were subjected to SDS-polyacrylamide gel electrophoresis. The gel was blotted and analyzed using the WESTERN BLOTTING PROCEDURE. Polyclonal goat anti-PRV gIII (gpC) antibody was used to detect expression of PRV specific proteins. As shown in FIG. 16, the lysate from S-SPV-012 infected cells exhibits two specific bands which are the reported size of PRV gIII (gpC) (37)—a 92 kd mature form and a 74 kd pre-golgi form.

Recombinant-expressed PRV gIII (gpC) has been shown to elicit a significant immune response in mice and swine (37, 38). Furthermore, when gIII (gpC) is coexpressed with gII (gpB) or g50 (gpD), significant protection from challenge with virulent PRV is obtained (39). Therefore S-SPV-012 should be valuable as a vaccine to protect swine against PRV disease. Since the PRV vaccines described here do not express PRV gpX or gpI, they would be compatible with current PRV diagnostic tests (gX HerdChek®, gI HerdChek® and ClinEase®) which are utilized to distinguish vaccinated animals from infected animals.

Example 6

S-SPV-013

S-SPV-013 is a swinepox virus that expresses at least two foreign genes. The gene for *E. coli* B-galactosidase (lacZ) and the gene for pseudorabies virus gIII (gpC) were inserted into the unique PstI restriction site (PstI linkers inserted into a unique AccI site) of the homology vector 570-33.32. The lacZ gene is under the control of the synthetic late promoter (LP1) and the PRV gIII (gpC) gene is under the control of the synthetic late early promoter (LP2EP2).

S-SPV-013 was derived from S-SPV-001 (Kasza Strain). This was accomplished utilizing the homology vector 570-91.64 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING B-GALACTOSIDASE (BLUOGAL AND CPRG ASSAYS). The final result of red plaque purification was the recombinant virus designated S-SPV-013. This virus was assayed for B-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-013 was assayed for expression of PRV specific antigens using the BLACK PLAQUE SCREEN FOR FOREIGN GENE EXPRESSION IN RECOMBINANT SPV. Polyclonal goat anti-PRV gIII (gpC) antibody was shown to react specifically with S-SPV-013 plaques and not with S-SPV-001 negative control plaques. All S-SPV-013 observed plaques reacted with the swine anti-PRV serum indicating that the virus was stably expressing the PRV foreign gene. The assays described here were carried out in EMSK and VERO cells, indicating that EMSK cells would be a suitable substrate for the production of SPV recombinant vaccines.

To confirm the expression of the PRV gIII (gpC) gene product, cells were infected with SPV and samples of infected cell lysates were subjected to SDS-polyacrylamide gel electrophoresis. The gel was blotted and analyzed using the WESTERN BLOTTING PROCEDURE. Polyclonal goat anti-PRV gIII (gpC) antibody was used to detect expression of PRV specific proteins. As shown in FIG. 16, the lysate from S-SPV-013 infected cells exhibits two specific bands which are the reported size of PRV gIII (gpC) (37)—a 92 kd mature form and a 74 kd pre-Golgi form.

Recombinant-expressed PRV gIII (gpC) has been shown to elicit a significant immune response in mice and swine (39, 38). Furthermore, when gIII (gpC) is coexpressed with gII (gpB) or g50 (gpD), significant protection from challenge with virulent PRV is obtained. (39) Therefore S-SPV-013 should be valuable as a vaccine to protect swine against PRV disease. Since the PRV vaccines described here do not express PRV gpX or gpI, they would be compatible with current PRV diagnostic tests (gX HerdChek®, gI HerdChek® and ClinEase®) which are utilized to distinguish vaccinated animals from infected animals. S-SPV-013 has been deposited with the ATCC under Accession No. VR 2418.

Example 7

S-SPV-015

S-SPV-015 is a swinepox virus that expresses at least two foreign genes. The gene for *E. coli* B-galactosidase (lacZ gene) and the gene for pseudorabies virus (PRV) gII (gpB) are inserted into the SPV 515-85.1 ORF. The lacZ gene is under the control of a synthetic late promoter (LP1) and the gII (gpB) gene is under the control of a synthetic late/early promoter (LP2EP2).

S-SPV-015 can be derived from S-SPV-001 (Kasza strain). This is accomplished utilizing the lacZ/PRV gII (gpB) homology vector (see Materials and Methods) and virus S-SPV-001 in the HOMOLOGOUS RECOMBINATION PROCEDURE FOR GENERATING RECOMBINANT SPV. The transfection stock is screened by the SCREEN FOR RECOMBINANT SPV EXPRESSING B-GALACTOSIDASE (BLUOGAL AND CPRG ASSAYS).

Example 8

Recombinant swinepox virus expressing more than one pseudorabies virus (PRV) glycoproteins, which can elicit production of neutralizing antibodies against pseudorabies virus, is constructed in order to obtain a recombinant swinepox virus with enhanced ability to protect against PRV infection than that which can be obtained by using a recombinant swinepox virus expressing only one of those PRV glycoproteins.

There are several examples of such recombinant swinepox virus expressing more than one PRV glycoproteins: a recombinant swinepox virus expressing PRV g50 (gpD) and gIII (gpC), a recombinant swinepox virus expressing PRV g50 (gpD) and gII (gpB); a recombinant swinepox virus expressing PRV gII (gpB) and gIII (gpC); and a recombinant swinepox virus expressing PRV g50 (gpD), gIII (gpC) and gII (gpB). Each of the viruses cited above is also engineered to contain and express E. coli B-galactosidase (lac Z) gene, which will facilitate the cloning of the recombinant swinepox virus.

Listed below are three examples of a recombinant swinepox virus expressing PRV g50 (gpD), PRV gIII (gpC), PRV gII (gpB) and E. coli B-galactosidase (lacZ):

a) Recombinant swinepox virus containing and expressing PRV g50 (gpD) gene, PRV gIII (gpC) gene, PRV gII (gpB) gene and lacZ gene. All four genes are inserted into the unique AccI restriction endonuclease site within the HindIII M fragment of the swinepox virus genome. PRV g50 (gpD) gene is under the control of a synthetic early/late promoter (EP1LP2), PRV gIII (gpC) gene is under the control of a synthetic early promoter (EP2), PRV gII (gpB) gene is under the control of a synthetic late/early promoter (LP2EP2) and lacZ gene is under the control of a synthetic late promoter (LP1).

b) Recombinant swinepox virus containing and expressing PRV g50 (gpD) gene, PRV gIII (gpC) gene, PRV gII (gpB) gene and lacZ gene. All four genes are inserted into the unique AccI restriction endonuclease site within the HindIII M fragment of the swinepox virus genome. PRV g50 (gpD) gene is under the control of a synthetic early/late promoter (EP1LP2), PRV gIII (gpC) gene is under the control of a synthetic early/late promoter (EP1LP2), PRV gII (gpB) gene is under the control of a synthetic late/early promoter (LP2EP2) and lacZ gene is under the control of a synthetic late promoter (LP1).

c) Recombinant swinepox virus containing and expressing PRV g50 (gpD) gene, PRV gIII (gpC) gene, PRV gII (gpB) gene and lacZ gene. All four genes are inserted into the unique AccI restriction endonuclease site within the HindIII M fragment of the swinepox virus genome. PRV g50 (gpD) gene is under the control of a synthetic early/late promoter (EP1LP2), PRV gIII (gpC) gene is under the control of a synthetic late/early promoter (LP2EP2), PRV gII (gpB) gene is under the control of a synthetic late/early promoter (LP2EP2) and lacZ gene is under the control of a synthetic late promoter (LP1).

Example 9

S-SPV-009

S-SPV-009 is a swinepox virus that expresses at least two foreign genes. The gene for E. coli β-galactosidase (lacZ gene) and the gene for Newcastle's Disease virus hemagglutinin (HN) gene were inserted into the SPV 515-85.1 ORF. The lacZ gene is under the control of a synthetic late promoter (LP1) and the HN gene is under the control of an synthetic early/late promoter (EP1LP2).

S-SPV-009 was derived from S-SPV-001 (Kasza strain). This was accomplished utilizing the homology vector 538-46.26 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING β-GALACTOSIDASE (BLUOGAL AND CPRG ASSAYS). The final result of red plaque purification was the recombinant virus designated S-SPV-009. This virus was assayed for β-galactosidase expression, purity, and insert stability by multiple passages monitored by the blue plaque assay as described in Materials and Methods. After the initial three rounds of purification, all plaques observed were blue indicating that the virus was pure, stable and expressing the marker gene.

S-SPV-009 was assayed for expression of PRV specific antigens using the BLACK PLAQUE SCREEN FOR FOREIGN GENE EXPRESSION IN RECOMBINANT SPV. Rabbit anti-NDV HN serum was shown to react specifically with S-SPV-009 plaques and not with S-SPV-008 negative control plaques. All S-SPV-009 observed plaques reacted with the swine antiserum indicating that the virus was stably expressing the NDV foreign gene. S-SPV-009 has been deposited with the ATCC under Acession No. VR 2344).

To confirm the expression of the NDV HN gene product, cells were infected with SPV and samples of infected cell lysates were subjected to SDS-polyacrylamide gel electrophoresis. The gel was blotted and analyzed using the WESTERN BLOTTING PROCEDURE. The rabbit anti-NDV HN serum was used to detect expression of the HN protein. The lysate from S-SPV-009 infected cells exhibited a specific band of approximately 74 kd, the reported size of NDV HN (29).

Example 10

S-SPV-014

S-SPV-014 is a swinepox virus that expresses at least two foreign genes. The gene for E. coli B-galactosidase (lacZ) and the gene for infectious laryngotracheitis virus glycoprotein G (ILT gpG) were inserted into the SPV 570-33.32 ORF (a unique PstI site has replaced the unique AccI site). The lacZ gene is under the control of the synthetic late promoter (LP1), and the ILT gpG gene is under the control of the synthetic early/late promoter (EP1LP2).

S-SPV-014 was derived from S-SPV-001 (Kasza Strain). This was accomplished utilizing the homology vector 599-65.25 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING B-GALACTOSIDASE (BLUOGAL AND CPRG ASSAYS). The final result of red plaque purification was the recombinant virus designated S-SPV-014. This virus was assayed for B-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene. The assays described here were carried out in ESK-4 cells, indicating that ESK-4 cells would be a suitable substrate for the production of SPV recombinant vaccines.

To confirm the expression of the ILT gpG gene product, cells were infected with SPV-014 and samples of infected cell lysates were subjected to SDS-polyacrylamide gel electrophoresis. The gel was blotted and analyzed using the WESTERN BLOTTING PROCEDURE. Peptide antisera to ILT gG was used to detect expression of ILT specific proteins. The lysate from S-SPV-014 infected cells exhibited a band at 43 kd which is the expected size of the ILT gpG protein and additional bands of higher molecular weight which represent glycosylated forms of the protein which are absent in deletion mutants for ILT gpG.

This virus is used as an expression vector for expressing ILT glycoprotein G (gpG). Such ILT gpG is used as an antigen to identify antibodies directed against the wild-type ILT virus as opposed to antibodies directed against gpG deleted ILT viruses. This virus is also used as an antigen for the production of ILT gpG specific monoclonal antibodies. Such antibodies are useful in the development of diagnostic tests specific for the ILT gpG protein. Monoclonal antibodies are generated in mice utilizing this virus according to the PROCEDURE FOR PURIFICATION OF VIRAL GLYCOPROTEINS FOR USE AS DIAGNOSTICS (*Materials & Methods*).

Example 11

S-SPV-016

S-SPV-016 is a swinepox virus that expresses at least two foreign genes. The gene for *E. coli* B-galactosidase (lacZ) and the gene for infectious laryngotracheitis virus glycoproteini (ILT gpI) were inserted into the SPV 617-48.1 ORF (a unique NotI restriction site has replaced a unique AccI restriction site). The lacZ gene is under the control of the synthetic late promoter (LP1), and the ILT gpI gene is under the control of the synthetic late/early promoter (LP2EP2).

S-SPV-016 was derived from S-SPV-001 (Kasza Strain). This was accomplished utilizing the homology vector 624-20.1C (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING B-GALACTOSIDASE (BLUOGAL AND CPRG ASSAYS). The final result of red plaque purification was the recombinant virus designated S-SPV-016. This virus was assayed for B-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-016 was assayed for expression of ILT gpI- and B-galactosidase-specific antigens using the BLACK PLAQUE SCREEN FOR FOREIGN GENE EXPRESSION IN RECOMBINANT SPV. Polyclonal chicken anti-ILT antibody was shown to react specifically with S-SPV-016 plaques and not with S-SPV-017 negative control plaques. All S-SPV-016 observed plaques reacted with the chicken antiserum indicating that the virus was stably expressing the ILT foreign gene. The assays described here were carried out in ESK-4 cells, indicating that ESK-4 cells would be a suitable substrate for the production of SPV recombinant vaccines.

To confirm the expression of the ILT gpI gene product, cells were infected with SPV-016 and samples of infected cell lysates were subjected to SDS-polyacrylamide gel electrophoresis. The gel was blotted and analyzed using the WESTERN BLOTTING PROCEDURE. Polyclonal chicken anti-ILT antibody was used to detect expression of ILT specific proteins. The lysate from S-SPV-016 infected cells exhibits a range of bands reactive to the anti-ILT antibody from 40 to 200 kd indicating that the ILT gpI may be heavily modified.

This virus is used as an expression vector for expressing ILT glycoprotein I (gpI). Such ILT gpI is used as an antigen to identify antibodies directed against the wild-type ILT virus as opposed to antibodies directed against gpI deleted ILT viruses. This virus is also used as an antigen for the production of ILT gpI specific monoclonal antibodies. Such antibodies are useful in the development of diagnostic tests specific for the ILT gpI protein. Monoclonal antibodies are generated in mice utilizing this virus according to the PROCEDURE FOR PURIFICATION OF VIRAL GLYCOPROTEINS FOR USE AS DIAGNOSTICS (*Materials & Methods*).

Example 12

S-SPV-017

S-SPV-017 is a swinepox virus that expresses at least two foreign genes. The gene for *E. coli* B-galactosidase (lacZ) and the gene for infectious bovine rhinotracheitis virus glycoprotein G (IBR gpG) were inserted into the SPV 617-48.1 ORF (a unique NotI restriction site has replaced a unique AccI restriction site). The lacZ gene is under the control of the synthetic late promoter (LP1), and the IBR gpG gene is under the control of the synthetic late/early promoter (LP2EP2).

S-SPV-017 was derived from S-SPV-001 (Kasza Strain). This was accomplished utilizing the homology vector 614-83.18 (see Materials and Methods) and virus S-SPV-001 in the HOMOLOGOUS RECOMBINATION PROCEDURE FOR GENERATING RECOMBINANT SPV. The transfection stock was screened by the SCREEN FOR RECOMBINANT SPV EXPRESSING B-GALACTOSIDASE (BLUOGAL AND CPRG ASSAYS). The final result of red plaque purification was the recombinant virus designated S-SPV-017.

This virus was assayed for B-galactosidase expression, purity, and insert stability by multiple passages monitored by the blue plaque assay as described in Materials and Methods. After the initial three rounds of purification, all plaques observed were blue indicating that the virus was pure, stable, and expressing the foreign gene.

S-SPV-017 was assayed for expression of IBR-specific antigens using the BLACK PLAQUE SCREEN FOR FOREIGN GENE EXPRESSION IN RECOMBINANT SPV. Monoclonal antibodies and peptide antisera to IBR gpG were shown to react specifically with S-SPV-017 plaques and not with S-SPV-016 negative control plaques. All S-SPV-017 observed plaques reacted with the antiserum indicating that the virus was stably expressing the IBR foreign gene. The assays described here were carried out in ESK-4 cells, indicating that ESK-4 cells would be a suitable substrate for the production of SPV recombinant vaccines.

To confirm the expression of the IBR gpG gene product, cells were infected with SPV-017 and samples of infected cell lysates were subjected to SDS-polyacrylamide gel electrophoresis. The gel was blotted and analyzed using the WESTERN BLOTTING PROCEDURE. Antisera to IBR gpG was used to detect expression of IBR specific proteins. The lysate from S-SPV-017 infected cells exhibited a band at 43 kd which is the expected size of the IBR gpG protein and additional bands of higher molecular weight which represent glycosylated forms of the protein which are absent in deletion mutants for IBR gpG.

This virus is used as an expression vector for expressing IBR glycoprotein G (gpG). Such IBR gpG is used as an antigen to identify antibodies directed against the wild-type IBR virus as opposed to antibodies directed against gpG deleted IBR viruses. This virus is also used as an antigen for the production of IBR gpG specific monoclonal antibodies. Such antibodies are useful in the development of diagnostic tests specific for the IBR gpG protein. Monoclonal antibodies are generated in mice utilizing this virus according to the PROCEDURE FOR PURIFICATION OF VIRAL GLYCOPROTEINS FOR USE AS DIAGNOSTICS (*Materials & Methods*).

Example 13
S-SPV-019

S-SPV-019 is a swinepox virus that expresses at least two foreign genes. The gene for *E. coli* B-galactosidase (lacZ gene) and the gene for infectious bovine rhinotracheitits virus (IBR) glycoproteinE (gpE) are inserted into the SPV 515-85.1 ORF. The lacZ gene is under the control of a synthetic late promoter (LP1) and the gpE gene is under the control of a synthetic early/late promoter (LP2EP2).

S-SPV-019 is derived from S-SPV-001 (Kasza strain). This is accomplished utilizing the lacZ/IBR gpE homology vector (see Materials and Methods) and virus S-SPV-001 in the HOMOLOGOUS RECOMBINATION PROCEDURE FOR GENERATING RECOMBINANT SPV. The transfection stock is screened by the SCREEN FOR RECOMBINANT SPV EXPRESSING B-GALACTOSIDASE (BLUOGAL AND CPRG ASSAYS).

This virus is used as an expression vector for expressing IBR glycoprotein E (gpE). Such IBR gpE is used as an antigen to identify antibodies directed against the wild-type IBR virus as opposed to antibodies directed against gpE deleted IBR viruses. This virus is also used as an antigen for the production of IBR gpE specific monoclonal antibodies. Such antibodies are useful in the development of diagnostic tests specific for the IBR gpE protein. Monoclonal antibodies are generated in mice utilizing this virus according to the PROCEDURE FOR PURIFICATION OF VIRAL GLYCOPROTEINS FOR USE AS DIAGNOSTICS (*Materials & Methods*).

Example 14

S-SPV-018

S-SPV-018 is a swinepox virus that expresses at least two foreign genes. The gene for *E. coli* B-galactosidase (lacZ) and the gene for pseudorabies virus glycoprotein E (PRV gpE) are inserted into the SPV 570-33.32 ORF (a unique PstI site has replaced the unique AccI site). The lacZ gene is under the control of the synthetic late promoter (LP1), and the PRV gpE gene is under the control of the synthetic early/late promoter (EP1LP2).

S-SPV-018 is derived from the S-SPV-001 (Kasza Strain). This is accomplished utilizing the final homology vector and virus S-SPV-001 in the HOMOLOGOUS RECOMBINATION PROCEDURE FOR GENERATING RECOMBINANT SPV. The transfection stock is screened by the SCREEN FOR RECOMBINANT SPV EXPRESSING B-GALACTOSIDASE (BLUOGAL AND CPRG ASSAYS). Red plaque purification of the recombinant virus is designated S-SPV-018. This virus is assayed for B-galactosidase expression, purity, and insert stability by multiple passages monitored by the blue plaque assay described in Materials and Methods. After the initial three rounds of purification, all plaques observed are blue indicating that the virus is pure, stable, and expressing the foreign gene.

This virus is used as an expression vector for expressing PRV glycoprotein E (gpE). Such PRV gpE is used as an antigen to identify antibodies directed against the wild-type PRV virus as opposed to antibodies directed against gpE deleted PRV viruses. This virus is also used as an antigen for the production of PRV gpE specific monoclonal antibodies. Such antibodies are useful in the development of diagnostic tests specific for the PRV gpE protein. Monoclonal antibodies are generated in mice utilizing this virus according to the PROCEDURE FOR PURIFICATION OF VIRAL GLYCOPROTEINS FOR USE AS DIAGNOSTICS (*Materials & Methods*).

Example 15

Homology Vector 520-90.15

The homology vector 520-90.15 is a plasmid useful for the insertion of foreign DNA into SPV. Plasmid 520-90.15 contains a unique NdeI restriction site into which foreign DNA may be cloned. A plasmid containing such a foreign DNA insert has been used according to the HOMOLOGOUS RECOMBINATION PROCEDURE FOR GENERATING RECOMBINANT SPV to generate a SPV containing the foreign DNA. For this procedure to be successful, it is important that the insertion site be in a region nonessential to the replication of the SPV and that the site be flanked with swinepox virus DNA appropriate for mediating homologous recombination between virus and plasmid DNAs. The unique NdeI restriction site in plasmid 520-90.15 is located within the coding region of the SPV thymidine kinase gene (32). Therefore, we have shown that the thymidine kinase gene of swinepox virus is non-essential for DNA replication and is an appropriate insertion site.

Example 16

S-PRV-010

S-SPV-010 is a swinepox virus that expresses a foreign gene. The *E. coli* B-galactosidase (lacZ) gene is inserted into a unique NdeI restriction site within the thymidine kinase gene. The foreign gene (lacZ) is under the control of the synthetic late promoter, LP1. We have shown that the swinepox virus thymidine kinase gene is non-essential for replication of the virus and is an appropriate insertion site.

A 1739 base pair HindIII-BamHI fragment subcloned from the HindIII G fragment contains the swinepox virus thymidine kinase gene and is designated homology vector 520-90.15. The homology vector 520-90.15 was digested with Nde I, and AscI linkers were inserted at this unique site within the thymidine kinase gene. The LP1 promoter-lac Z cassette with AscI linkers was ligated into the Asc I site within the thymidine kinase gene. The recombinant homology vector 561-36.26 was cotransfected with virus S-SPV-001 by the HOMOLOGOUS RECOMBINATION PROCEDURE FOR GENERATING RECOMBINANT SPV and virus plaques expressing B-galactosidase were selected by SCREEN FOR RECOMBINANT SPV EXPRESSING B-GALACTOSIDASE (BLUOGAL AND CPRG ASSAY). The final result of blue and red plaque purification was the recombinant virus designated S-SPV-010. This virus was assayed for B-galactosidase expression, purity, and insert stability by multiple passages monitored by the blue plaque assay as described in Materials and Methods. After the initial three rounds of purification, all plaques observed were blue indicating that the virus was pure, stable and expressing the foreign gene. The assays described here were carried out in ESK-4 cells, indicating that ESK-4 cells would be a suitable substrate for the production of SPV recombinant vaccines.

Example 17

The development of vaccines utilizing the swinepox virus to express antigens from various disease causing microorganisms can be engineered.

TRANSMISSIBLE GASTROENTERITIS VIRUS

The major neutralizing antigen of the transmissible gastroenteritis virus (TGE), glycoprotein 195, for use in the swinepox virus vector has been cloned. The clone of the neutralizing antigen is disclosed in U.S. Ser. No. 078,519, filed Jul. 27, 1987. It is contemplated that the procedures that have been used to express PRV g50 (gpD) in SPV and are disclosed herein are applicable to TGE.

PORCINE PARVOVIRUS

We have cloned the major capsid protein of the porcine (swine) parvovirus (PPV) for use in the swinepox virus vector. The clone of the capsid protein is disclosed in U.S. Pat. No. 5,068,192 issued Nov. 26, 1991. It is contemplated that the procedures that have been used to express PRV g50 (gpD) in SPV and are disclosed herein are applicable to PPV.

SWINE ROTAVIRUS

We have cloned the major neutralizing antigen of the swine rotavirus, glycoprotein 38, for use in the swinepox virus vector. The clone of glycoprotein 38 is disclosed in U.S. Pat. No. 5,068,192 issued Nov. 26, 1991. It is contemplated that the procedures that have been used to express PRV g50 (gpD) in SPV and are disclosed herein are applicable to SRV.

HOG CHOLERA VIRUS

The major neutralizing antigen of the bovine viral diarrhea (BVD) virus was cloned as disclosed in U.S. Ser. No. 225,032, filed Jul. 27, 1988. Since the BVD and hog cholera viruses are cross protective (31), the BVD virus antigen has been targeted for use in the swinepox virus vector. It is contemplated that the procedures that have been used to express PRV g50 (gpD) in SPV and are disclosed herein are applicable to BVD virus.

*SERPULINA HYODYSENTERIAE*

A protective antigen of *Serpulina hyodysenteriae* (3), for use in the swinepox virus vectorhas been cloned. It is contemplated that the procedures that have been used to express PRV gp50 in SPV and are disclosed herein are also applicable to *Serpulina hyodysenteriae*.

Antigens from the following microorganisms may also be utilized to develop animal vaccines: Swine influenza virus, foot and mouth disease virus, African swine fever virus, hog cholera virus and *Mycoplasma hyodysenteriae*.

REFERENCES

1. C. Bertholet, et al., *EMBO Journal* 5, 1951–1957 (1986)
2. R. A. Bhat, et al., *Nucleic Acids Research* 17, 1159–1176 (1989).
3. D. A. Boyden, et al., *Infection and Immunity* 57, 3808–3815 (1989).
4. D. B. Boyle and B. E. H. Coupar, *Virus Research* 10, 343–356 (1988).
5. R. M. Buller, et al., *Nature* 317, 813–815 (1985).
6. K. J. Cremer, et al., *Science* 228, 737–739 (1985).
7. A. J. Davidson and B. Moss, *J. Mol. Biol.* 210, 749–769 (1989).
8. A. J. Davidson and B. Moss, *J. Mol. Biol.* 210, 771–784 (1989).
9. P. L. Earl, et al., *Journal of Virology* 64, 2448–2451 (1990).
10. J. J. Esposito, et al., *Virology* 165, 313 (1988).
11. F. A. Ferrari, et al., *J. of Bacteriology* 161, 556–562 (1985).
12. C. Flexner, et al., Vaccine 8, 17–21 (1990).
13. S. J. Goebel, et al., *Virology* 179, 247–266 (1990).
14. U. Gubler and B. J. Hoffman, *Gene* 25, 263–269 (1983).
15. M. A. Innis, et al., *PCR Protocols A Guide to Methods and Applications*, 84–91, Academic Press, Inc., San Diego (1990).
16. S. Joshi, et al., Journal of Virology. 65, 5524–5530 (1991).
17. L. Kasza, et al., *Am. J. Vet. Res.* 21, 269–273 (1960).
18. L. Kasza, Diseases of Swine, 254–260, Ed. A.D. Leman, et al., The Iowa State University Press, Ames, Iowa (1981).
19. B. G. Klupp and T. C. Mettenleiter, *Virology* 182, 732–741 (1991).
20. U. K. Laemnli, *Nature* 227, 680–685 (1970).
21. B. Lominiczi, et al., *Journal of Virology* 49, 970–979 (1984).
22. T. Maniatis, et al., *Molecular Cloning: A Laboratory Manual*, Cold Spring Harbor Press, Cold Spring Harbor, N.Y. (1982).
23. R. F. Massung, and R. W. Moyer, *Virology* 180, 347–354 (1991).
24. R. F. Massung, and R. W. Moyer, *Virology* 180, 355–364 (1991).
25. B. Moss, *Science* 252, 1662–1667 (1991).
26. E. A. Petrovskis, et al., *Journal of Virology* 59, 216–223 (1986).
27. A. K. Robbins et al., *Journal of Virology* 58, 339–347 (1986).
28. A. K. Robbins et al., *Journal of Virology* 61, 2691–2701 (1987).
29. A. C. R. Samson, *Journal of Virology* 67, 1199–1203 (1986).
30. J. Sambrook, et al., *Molecular Cloning A Laboratory Manual Second Edition*, Cold Spring Harbor Press, Cold Spring Harbor, N.Y. (1989).
31. Sheffy, et al., *Proceedings 65th Annual Meeting of the United States Livestock Association* 65, 347–353 (1961).
32. W. M. Schnitzlein and D. N. Tripathy, *Virology* 181, 727–732, (1991).
33. J. Taylor, et al., *Vaccine* 9, 190–193, (1991).
34. M. Wachsman, et al., *Journal of General Virology* 70, 2513–2520 (1989).
35. M. W. Wathen, et al., *Journal of Virology* 51, 57–62 (1984).
36. M. Weerasinge, *Journal of Virology* 65, 5531–5534 (1991).
37. T. Ben-Porat, et al., *Journal of Virology*, volume 154, 325–334 (1986).
38. F. Zuckerman, et al., Vaccination and Control of Adjesky's Disease, J. T. Van Oirchot (ed.). Kluwer Academic Publishers, London, pp. 107–117 (1989).
39. Paolette, et al., *Journal of Virology*, volume 66, pp. 3424–3434 (June, 1992).
40. M. W. Mellencamp, et al., *Journal of Clinical Microbiology*, volume 27, pp. 2208–2213 (1989).
41. L. A. Herzenberg, et al., Selected Methods in Cellular Immunology, Freeman Publ. Co., San Francisco, 351–372 (1980).

What is claimed is:

1. A recombinant swinepox virus which comprises a foreign DNA inserted within a HindIII M fragment of a swinepox virus genomic DNA, wherein the foreign DNA is selected from the group consisting of: Infectious Laryngotracheitis Virus glycoprotein I, Infectious Laryngotracheitis Virus glycoprotein G, Infectious Bovine Rhinotracheitis glycoprotein G, Infectious Bovine Rhinotracheitis glycoprotein E, Newcastle Disease Virus hemagglutininneuraminidase, Pseudorabies Virus glycoprotein 50, Pseudorabies Virus glycoprotein III, Pseudorabies Virus glycoprotein E and Pseudorabies Virus glycoprotein H.

2. The recombinant swinepox virus of claim 1, further comprising a second foreign DNA inserted within the thymidine kinase gene of the swinepox virus genomic DNA.

3. The recombinant swinepox virus of claim 1, wherein the foreign DNA is under the control of a promoter.

4. The recombinant swinepox virus of claim 1, designated S-SPV-013 (ATCC Accession Number VR 2418).

* * * * *

SEQUENCE LISTING ( 1 ) GENERAL INFORMATION:

( i i i ) NUMBER OF SEQUENCES: 112

( 2 ) INFORMATION FOR SEQ ID NO:1:

( i ) SEQUENCE CHARACTERISTICS:
( A ) LENGTH: 599 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Swinepox virus
( B ) STRAIN: Kasza
( C ) INDIVIDUAL ISOLATE: S-SPV- 001

( v i i ) IMMEDIATE SOURCE:
( B ) CLONE: 515-85.1

( v i i i ) POSITION IN GENOME:
( B ) MAP POSITION: []23.2
( C ) UNITS: %G ( i x ) FEATURE:
( A ) NAME/KEY: CDS
( B ) LOCATION: 202..597
( D ) OTHER INFORMATION: /partial
/ codon_start= 202
/ function= "Potential eukaryotic transcriptional regulatory protein"
/ standard_name= "515-85.1 ORF"

( x i ) SEQUENCE DESCRIPTION: SEQ ID NO:1:

```
AATGTATCCA GAGTTGTTGA ATGCCTTATC GTACCTAATA TTAATATAGA GTTATTAACT      60

GAATAAGTAT ATATAAATGA TTGTTTTTAT AATGTTTGTT ATCGCATTTA GTTTTGCTGT     120

ATGGTTATCA TATACATTTT TAAGGCCGTA TATGATAAAT GAAAATATAT AAGCACTTAT     180

TTTTGTTAGT ATAATAACAC A ATG CCG TCG TAT ATG TAT CCG AAG AAC GCA       231
                        Met Pro Ser Tyr Met Tyr Pro Lys Asn Ala
                          1               5                  10

AGA AAA GTA ATT TCA AAG ATT ATA TCA TTA CAA CTT GAT ATT AAA AAA       279
Arg Lys Val Ile Ser Lys Ile Ile Ser Leu Gln Leu Asp Ile Lys Lys
                 15                  20                  25

CTT CCT AAA AAA TAT ATA AAT ACC ATG TTA GAA TTT GGT CTA CAT GGA       327
Leu Pro Lys Lys Tyr Ile Asn Thr Met Leu Glu Phe Gly Leu His Gly
             30                  35                  40

AAT CTA CCA GCT TGT ATG TAT AAA GAT GCC GTA TCA TAT GAT ATA AAT       375
Asn Leu Pro Ala Cys Met Tyr Lys Asp Ala Val Ser Tyr Asp Ile Asn
         45                  50                  55

AAT ATA AGA TTT TTA CCT TAT AAT TGT GTT ATG GTT AAA GAT TTA ATA       423
Asn Ile Arg Phe Leu Pro Tyr Asn Cys Val Met Val Lys Asp Leu Ile
     60                  65                  70

AAT GTT ATA AAA TCA TCA TCT GTA ATA GAT ACT AGA TTA CAT CAA TCT       471
Asn Val Ile Lys Ser Ser Ser Val Ile Asp Thr Arg Leu His Gln Ser
 75                  80                  85                  90

GTA TTA AAA CAT CGT AGA GCG TTA ATA GAT TAC GGC GAT CAA GAC ATT       519
Val Leu Lys His Arg Arg Ala Leu Ile Asp Tyr Gly Asp Gln Asp Ile
                 95                 100                 105

ATC ACT TTA ATG ATC ATT AAT AAG TTA CTA TCG ATA GAT GAT ATA TCC       567
```

-continued

Ile Thr Leu Met Ile Ile Asn Lys Leu Leu Ser Ile Asp Asp Ile Ser
110 115 120

TAT ATA TTA GAT AAA AAA ATA ATT CAT GTA AC 599
Tyr Ile Leu Asp Lys Lys Ile Ile His Val
125 130

( 2 ) INFORMATION FOR SEQ ID NO:2:

( i ) SEQUENCE CHARACTERISTICS:
( A ) LENGTH: 132 amino acids
( B ) TYPE: amino acid
( D ) TOPOLOGY: linear ( i i ) MOLECULE TYPE: protein ( x i ) SEQUENCE DESCRIPTION: SEQ ID NO:2:

Met Pro Ser Tyr Met Tyr Pro Lys Asn Ala Arg Lys Val Ile Ser Lys
1 5 10 15

Ile Ile Ser Leu Gln Leu Asp Ile Lys Lys Leu Pro Lys Lys Tyr Ile
20 25 30

Asn Thr Met Leu Glu Phe Gly Leu His Gly Asn Leu Pro Ala Cys Met
35 40 45

Tyr Lys Asp Ala Val Ser Tyr Asp Ile Asn Asn Ile Arg Phe Leu Pro
50 55 60

Tyr Asn Cys Val Met Val Lys Asp Leu Ile Asn Val Ile Lys Ser Ser
65 70 75 80

Ser Val Ile Asp Thr Arg Leu His Gln Ser Val Leu Lys His Arg Arg
85 90 95

Ala Leu Ile Asp Tyr Gly Asp Gln Asp Ile Ile Thr Leu Met Ile Ile
100 105 110

Asn Lys Leu Leu Ser Ile Asp Asp Ile Ser Tyr Ile Leu Asp Lys Lys
115 120 125

Ile Ile His Val
130

( 2 ) INFORMATION FOR SEQ ID NO:3:

( i ) SEQUENCE CHARACTERISTICS:
( A ) LENGTH: 899 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Swinepox virus
( B ) STRAIN: Kasza
( C ) INDIVIDUAL ISOLATE: S-SPV- 001

( v i i ) IMMEDIATE SOURCE:
( B ) CLONE: 515-85.1

( v i i i ) POSITION IN GENOME:
( B ) MAP POSITION: []23.2
( C ) UNITS: %G ( i x ) FEATURE:
( A ) NAME/KEY: CDS
( B ) LOCATION: 3..662
( D ) OTHER INFORMATION: /partial
/ codon_start= 3
/ function= "Potential eukaryotic transcriptional regulatory protein"

/ standard_name= "515-85.1 ORF"

( x i ) SEQUENCE DESCRIPTION: SEQ ID NO:3:

| GA | GAT | ATT | AAA | TCA | TGT | AAA | TGC | TCG | ATA | TGT | TCC | GAC | TCT | ATA | ACA | 47 |
| | Asp | Ile | Lys | Ser | Cys | Lys | Cys | Ser | Ile | Cys | Ser | Asp | Ser | Ile | Thr | |
| | 1 | | | 5 | | | | | 10 | | | | | | 15 | |

| CAT | CAT | ATA | TAT | GAA | ACA | ACA | TCA | TGT | ATA | AAT | TAT | AAA | TCT | ACC | GAT | 95 |
| His | His | Ile | Tyr | Glu | Thr | Thr | Ser | Cys | Ile | Asn | Tyr | Lys | Ser | Thr | Asp | |
| | | | | 20 | | | | | 25 | | | | | 30 | | |

| AAT | GAT | CTT | ATG | ATA | GTA | TTG | TTC | AAT | CTA | ACT | AGA | TAT | TTA | ATG | CAT | 143 |
| Asn | Asp | Leu | Met | Ile | Val | Leu | Phe | Asn | Leu | Thr | Arg | Tyr | Leu | Met | His | |
| | | | 35 | | | | | 40 | | | | | 45 | | | |

| GGG | ATG | ATA | CAT | CCT | AAT | CTT | ATA | AGC | GTA | AAA | GGA | TGG | GGT | CCC | CTT | 191 |
| Gly | Met | Ile | His | Pro | Asn | Leu | Ile | Ser | Val | Lys | Gly | Trp | Gly | Pro | Leu | |
| | | 50 | | | | | 55 | | | | | 60 | | | | |

| ATT | GGA | TTA | TTA | ACG | GGT | GAT | ATA | GGT | ATT | AAT | TTA | AAA | CTA | TAT | TCC | 239 |
| Ile | Gly | Leu | Leu | Thr | Gly | Asp | Ile | Gly | Ile | Asn | Leu | Lys | Leu | Tyr | Ser | |
| | 65 | | | | | 70 | | | | | 75 | | | | | |

| ACC | ATG | AAT | ATA | AAT | GGG | CTA | CGG | TAT | GGA | GAT | ATT | ACG | TTA | TCT | TCA | 287 |
| Thr | Met | Asn | Ile | Asn | Gly | Leu | Arg | Tyr | Gly | Asp | Ile | Thr | Leu | Ser | Ser | |
| 80 | | | | | 85 | | | | | 90 | | | | | 95 | |

| TAC | GAT | ATG | AGT | AAT | AAA | TTA | GTC | TCT | ATT | ATT | AAT | ACA | CCC | ATA | TAT | 335 |
| Tyr | Asp | Met | Ser | Asn | Lys | Leu | Val | Ser | Ile | Ile | Asn | Thr | Pro | Ile | Tyr | |
| | | | | 100 | | | | | 105 | | | | | 110 | | |

| GAG | TTA | ATA | CCG | TTT | ACT | ACA | TGT | TGT | TCA | CTC | AAT | GAA | TAT | TAT | TCA | 383 |
| Glu | Leu | Ile | Pro | Phe | Thr | Thr | Cys | Cys | Ser | Leu | Asn | Glu | Tyr | Tyr | Ser | |
| | | | 115 | | | | | 120 | | | | | 125 | | | |

| AAA | ATT | GTG | ATT | TTA | ATA | AAT | GTT | ATT | TTA | GAA | TAT | ATG | ATA | TCT | ATT | 431 |
| Lys | Ile | Val | Ile | Leu | Ile | Asn | Val | Ile | Leu | Glu | Tyr | Met | Ile | Ser | Ile | |
| | | 130 | | | | | 135 | | | | | 140 | | | | |

| ATA | TTA | TAT | AGA | ATA | TTG | ATC | GTA | AAA | AGA | TTT | AAT | AAC | ATT | AAA | GAA | 479 |
| Ile | Leu | Tyr | Arg | Ile | Leu | Ile | Val | Lys | Arg | Phe | Asn | Asn | Ile | Lys | Glu | |
| | 145 | | | | | 150 | | | | | 155 | | | | | |

| TTT | ATT | TCA | AAA | GTC | GTA | AAT | ACT | GTA | CTA | GAA | TCA | TCA | GGC | ATA | TAT | 527 |
| Phe | Ile | Ser | Lys | Val | Val | Asn | Thr | Val | Leu | Glu | Ser | Ser | Gly | Ile | Tyr | |
| 160 | | | | | 165 | | | | | 170 | | | | | 175 | |

| TTT | TGT | CAG | ATG | CGT | GTA | CAT | GAA | CAA | ATT | GAA | TTG | GAA | ATA | GAT | GAG | 575 |
| Phe | Cys | Gln | Met | Arg | Val | His | Glu | Gln | Ile | Glu | Leu | Glu | Ile | Asp | Glu | |
| | | | | 180 | | | | | 185 | | | | | 190 | | |

| CTC | ATT | ATT | AAT | GGA | TCT | ATG | CCT | GTA | CAG | CTT | ATG | CAT | TTA | CTT | CTA | 623 |
| Leu | Ile | Ile | Asn | Gly | Ser | Met | Pro | Val | Gln | Leu | Met | His | Leu | Leu | Leu | |
| | | | 195 | | | | | 200 | | | | | 205 | | | |

| AAG | GTA | GCT | ACC | ATA | ATA | TTA | GAG | GAA | ATC | AAA | GAA | ATA | TAACGTATTT | | | 672 |
| Lys | Val | Ala | Thr | Ile | Ile | Leu | Glu | Glu | Ile | Lys | Glu | Ile | | | | |
| | | 210 | | | | | 215 | | | | | 220 | | | | |

| TTTCTTTTAA | ATAAATAAAA | ATACTTTTTT | TTTTAAACAA | GGGGTGCTAC | CTTGTCTAAT | 732 |
| TGTATCTTGT | ATTTGGATC | TGATGCAAGA | TTATTAAATA | ATCGTATGAA | AAAGTAGTAG | 792 |
| ATATAGTTTA | TATCGTTACT | GGACATGATA | TTATGTTTAG | TTAATTCTTC | TTTGGCATGA | 852 |
| ATTCTACACG | TCGGANAAGG | TAATGTATCT | ATAATGGTAT | AAAGCTT | | 899 |

( 2 ) INFORMATION FOR SEQ ID NO:4:

( i ) SEQUENCE CHARACTERISTICS:
        ( A ) LENGTH: 220 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Asp  Ile  Lys  Ser  Cys  Lys  Cys  Ser  Ile  Cys  Ser  Asp  Ser  Ile  Thr  His
  1             5                  10                            15

His  Ile  Tyr  Glu  Thr  Thr  Ser  Cys  Ile  Asn  Tyr  Lys  Ser  Thr  Asp  Asn
               20                  25                       30

Asp  Leu  Met  Ile  Val  Leu  Phe  Asn  Leu  Thr  Arg  Tyr  Leu  Met  His  Gly
          35                  40                       45

Met  Ile  His  Pro  Asn  Leu  Ile  Ser  Val  Lys  Gly  Trp  Gly  Pro  Leu  Ile
     50                  55                       60

Gly  Leu  Leu  Thr  Gly  Asp  Ile  Gly  Ile  Asn  Leu  Lys  Leu  Tyr  Ser  Thr
 65                  70                       75                            80

Met  Asn  Ile  Asn  Gly  Leu  Arg  Tyr  Gly  Asp  Ile  Thr  Leu  Ser  Ser  Tyr
               85                       90                            95

Asp  Met  Ser  Asn  Lys  Leu  Val  Ser  Ile  Ile  Asn  Thr  Pro  Ile  Tyr  Glu
               100                      105                      110

Leu  Ile  Pro  Phe  Thr  Thr  Cys  Cys  Ser  Leu  Asn  Glu  Tyr  Tyr  Ser  Lys
          115                      120                      125

Ile  Val  Ile  Leu  Ile  Asn  Val  Ile  Leu  Glu  Tyr  Met  Ile  Ser  Ile  Ile
     130                      135                      140

Leu  Tyr  Arg  Ile  Leu  Ile  Val  Lys  Arg  Phe  Asn  Asn  Ile  Lys  Glu  Phe
145                      150                      155                      160

Ile  Ser  Lys  Val  Val  Asn  Thr  Val  Leu  Glu  Ser  Ser  Gly  Ile  Tyr  Phe
                    165                      170                      175

Cys  Gln  Met  Arg  Val  His  Glu  Gln  Ile  Glu  Leu  Glu  Ile  Asp  Glu  Leu
               180                      185                      190

Ile  Ile  Asn  Gly  Ser  Met  Pro  Val  Gln  Leu  Met  His  Leu  Leu  Leu  Lys
          195                      200                      205

Val  Ala  Thr  Ile  Ile  Leu  Glu  Glu  Ile  Lys  Glu  Ile
          210                 215                      220
```

( 2 ) INFORMATION FOR SEQ ID NO:5:

( i ) SEQUENCE CHARACTERISTICS:
        ( A ) LENGTH: 129 amino acids
        ( B ) TYPE: amino acid
        ( C ) STRANDEDNESS: double
        ( D ) TOPOLOGY: linear ( i i ) MOLECULE TYPE: peptide ( i i i ) HYPOTHETICAL: YES ( i v ) ANTI-SENSE: NO ( v ) FRAGMENT TYPE: N-terminal ( v i ) ORIGINAL SOURCE:
        ( A ) ORGANISM: Vaccinia virus
        ( B ) STRAIN: Copenhagen ( v i i i ) POSITION IN GENOME:
        ( B ) MAP POSITION: []23.2
        ( C ) UNITS: %G ( x i ) SEQUENCE DESCRIPTION: SEQ ID NO:5:

```
Met  Phe  Met  Tyr  Pro  Glu  Phe  Ala  Arg  Lys  Ala  Leu  Ser  Lys  Leu  Ile
  1             5                  10                            15

Ser  Lys  Lys  Leu  Asn  Ile  Glu  Lys  Val  Ser  Ser  Lys  His  Gln  Leu  Val
               20                  25                       30

Leu  Leu  Asp  Tyr  Gly  Leu  His  Gly  Leu  Leu  Pro  Lys  Ser  Leu  Tyr  Leu
          35                  40                       45

Glu  Ala  Ile  Asn  Ser  Asp  Ile  Leu  Asn  Val  Arg  Phe  Phe  Pro  Pro  Glu
     50                  55                       60
```

```
Ile  Ile  Asn  Val  Thr  Asp  Ile  Val  Lys  Ala  Leu  Gln  Asn  Ser  Cys  Arg
65             70                  75                            80

Val  Asp  Glu  Tyr  Leu  Lys  Ala  Val  Ser  Leu  Tyr  His  Lys  Asn  Ser  Leu
                85                  90                            95

Met  Val  Ser  Gly  Pro  Asn  Val  Val  Lys  Leu  Met  Ile  Glu  Tyr  Asn  Leu
               100                 105                      110

Leu  Thr  His  Ser  Asp  Leu  Glu  Trp  Leu  Ile  Asn  Glu  Asn  Val  Val  Lys
          115                 120                      125

Ala
```

(2) INFORMATION FOR SEQ ID NO:6:

(i) SEQUENCE CHARACTERISTICS:
        (A) LENGTH: 132 amino acids
        (B) TYPE: amino acid
        (C) STRANDEDNESS: double
        (D) TOPOLOGY: linear (ii) MOLECULE TYPE: peptide (iii) HYPOTHETICAL: YES (iv) ANTI-SENSE: NO (v) FRAGMENT TYPE: N-terminal (vi) ORIGINAL SOURCE:
        (A) ORGANISM: Swinepox virus
        (B) STRAIN: Kasza (viii) POSITION IN GENOME:
        (B) MAP POSITION: []23.2
        (C) UNITS: %G (xi) SEQUENCE DESCRIPTION: SEQ ID NO:6:

```
Met  Pro  Ser  Tyr  Met  Tyr  Pro  Lys  Asn  Ala  Arg  Lys  Val  Ile  Ser  Lys
1              5                   10                       15

Ile  Ile  Ser  Leu  Gln  Leu  Asp  Ile  Lys  Lys  Leu  Pro  Lys  Lys  Tyr  Ile
               20                  25                       30

Asn  Thr  Met  Leu  Glu  Phe  Gly  Leu  His  Gly  Asn  Leu  Pro  Ala  Cys  Met
          35                  40                       45

Tyr  Lys  Asp  Ala  Val  Ser  Tyr  Asp  Ile  Asn  Asn  Ile  Arg  Phe  Leu  Pro
     50                  55                       60

Tyr  Asn  Cys  Val  Met  Val  Lys  Asp  Leu  Ile  Asn  Val  Ile  Lys  Ser  Ser
65             70                  75                       80

Ser  Val  Ile  Asp  Thr  Arg  Leu  His  Gln  Ser  Val  Leu  Lys  His  Arg  Arg
               85                  90                       95

Ala  Leu  Ile  Asp  Tyr  Gly  Asp  Gln  Asp  Ile  Ile  Thr  Leu  Met  Ile  Ile
               100                 105                      110

Asn  Lys  Leu  Leu  Ser  Ile  Asp  Asp  Ile  Ser  Tyr  Ile  Leu  Asp  Lys  Lys
          115                 120                      125

Ile  Ile  His  Val
               130
```

(2) INFORMATION FOR SEQ ID NO:7:

(i) SEQUENCE CHARACTERISTICS:
        (A) LENGTH: 101 amino acids
        (B) TYPE: amino acid
        (C) STRANDEDNESS: double
        (D) TOPOLOGY: linear (ii) MOLECULE TYPE: peptide -continued (iii) HYPOTHETICAL: YES (iv) ANTI-SENSE: NO (v) FRAGMENT TYPE: C-terminal (vi) ORIGINAL SOURCE:
  (A) ORGANISM: Vaccinia virus
  (B) STRAIN: Copenhagen (viii) POSITION IN GENOME:
  (B) MAP POSITION: []23.2
  (C) UNITS: %G (xi) SEQUENCE DESCRIPTION: SEQ ID NO:7:

```
Val Leu Asn Asp Gln Tyr Ala Lys Ile Val Ile Phe Phe Asn Thr Ile
1               5                   10                  15

Ile Glu Tyr Ile Ile Ala Thr Ile Tyr Tyr Arg Leu Thr Val Leu Asn
            20                  25                  30

Asn Tyr Thr Asn Val Lys His Phe Val Ser Lys Val Leu His Thr Val
        35                  40                  45

Met Glu Ala Cys Gly Val Leu Phe Ser Tyr Ile Lys Val Asn Asp Lys
    50                  55                  60

Ile Glu His Glu Leu Glu Glu Met Val Asp Lys Gly Thr Val Pro Ser
65                  70                  75                  80

Tyr Leu Tyr His Leu Ser Ile Asn Val Ile Ser Ile Ile Leu Asp Asp
                85                  90                  95

Ile Asn Gly Thr Arg
            100
```

(2) INFORMATION FOR SEQ ID NO:8:

(i) SEQUENCE CHARACTERISTICS:
    (A) LENGTH: 100 amino acids
    (B) TYPE: amino acid
    (C) STRANDEDNESS: double
    (D) TOPOLOGY: linear (ii) MOLECULE TYPE: peptide (iii) HYPOTHETICAL: YES (iv) ANTI-SENSE: NO (v) FRAGMENT TYPE: C-terminal (vi) ORIGINAL SOURCE:
    (A) ORGANISM: Swinepox virus
    (B) STRAIN: Kasza (viii) POSITION IN GENOME:
  (B) MAP POSITION: []23.2
  (C) UNITS: %G (xi) SEQUENCE DESCRIPTION: SEQ ID NO:8:

```
Ser Leu Asn Glu Tyr Tyr Ser Lys Ile Val Ile Leu Ile Asn Val Ile
1               5                   10                  15

Leu Glu Tyr Met Ile Ser Ile Ile Leu Tyr Arg Ile Leu Ile Val Lys
            20                  25                  30

Arg Phe Asn Asn Ile Lys Glu Phe Ile Ser Lys Val Val Asn Thr Val
        35                  40                  45

Leu Glu Ser Ser Gly Ile Tyr Phe Cys Gln Met Arg Val His Glu Gln
    50                  55                  60

Ile Glu Leu Glu Ile Asp Glu Leu Ile Ile Asn Gly Ser Met Pro Val
65                  70                  75                  80

Gln Leu Met His Leu Leu Leu Lys Val Ala Thr Ile Ile Leu Glu Glu
```

|  | 85 | 90 | 95 |
|---|---|---|---|

Ile Lys Glu Ile
             100

( 2 ) INFORMATION FOR SEQ ID NO:9:

( i ) SEQUENCE CHARACTERISTICS:
        ( A ) LENGTH: 102 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 520-17.5 (Junction A)

( x ) PUBLICATION INFORMATION:
        ( A ) AUTHORS: Ferrari, Franco A
            Trach, Kathleen
            Hoch, James A
        ( B ) TITLE: Sequence Analysis of the spo0B Locus Revels a
            Polycistronic Transcription Unit
        ( C ) JOURNAL: J. Bacteriol.
        ( D ) VOLUME: 161
        ( E ) ISSUE: 2
        ( F ) PAGES: 556-562
        ( G ) DATE: Feb.-1985

( x i ) SEQUENCE DESCRIPTION: SEQ ID NO:9:

```
CACATACGAT  TTAGGTGACA  CTATAGAATA  CAAGCTTTAT  ACCATTATAG  ATACATTACC      60
TTGTCCGACG  TGTAGAATTC  ATGCCAAAGA  AGAATTAACT  AA                         102
```

( 2 ) INFORMATION FOR SEQ ID NO:10:

( i ) SEQUENCE CHARACTERISTICS:
        ( A ) LENGTH: 102 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 520-17.5 (Junction B)

( i x ) FEATURE:
        ( A ) NAME/KEY: CDS
        ( B ) LOCATION: 85..99
        ( D ) OTHER INFORMATION: /codon_start= 85
            / function= "Translational start of hybrid protein"
            / product= "N-terminal peptide"
            / number= 1
            / standard_name= "Translation of synthetic DNA
            sequence"

( i x ) FEATURE:
        ( A ) NAME/KEY: CDS
        ( B ) LOCATION: 100..102
        ( C ) IDENTIFICATION METHOD: experimental
        ( D ) OTHER INFORMATION: /partial /codon_start= 100
                /function= "marker enzyme"
                /product= "Beta-Galactosidase"
                /evidence= EXPERIMENTAL
                /gene= "lacZ"
                /number= 2
                /citation= ([1])

( x ) PUBLICATION INFORMATION:
                ( A ) AUTHORS: Ferrari, Franco A
                        Trach, Kathleen
                        Hoch, James A
                ( B ) TITLE: Seqquence Analysis of the spo0B Locus Reveals
                        a Polycistronic Transcription Unit
                ( C ) JOURNAL: J. Bacteriol.
                ( D ) VOLUME: 161
                ( E ) ISSUE: 2
                ( F ) PAGES: 556-562
                ( G ) DATE: Feb.-1985

( x i ) SEQUENCE DESCRIPTION: SEQ ID NO:10:

GTAGTCGACT CTAGAAAAAA TTGAAAAACT ATTCTAATTT ATTGCACGGA GATCTTTTTT       60

TTTTTTTTTT TTTTGGCAT ATAA ATG AAT TCG GAT CCC GTC                     102
                         Met Asn Ser Asp Pro Val
                          1           5       1

( 2 ) INFORMATION FOR SEQ ID NO:11:

( i ) SEQUENCE CHARACTERISTICS:
                ( A ) LENGTH: 5 amino acids
                ( B ) TYPE: amino acid
                ( D ) TOPOLOGY: linear ( i i ) MOLECULE TYPE: protein ( x i ) SEQUENCE DESCRIPTION: SEQ ID NO:11:

Met Asn Ser Asp Pro
 1           5

( 2 ) INFORMATION FOR SEQ ID NO:12:

( i ) SEQUENCE CHARACTERISTICS:
                ( A ) LENGTH: 1 amino acids
                ( B ) TYPE: amino acid
                ( D ) TOPOLOGY: linear ( i i ) MOLECULE TYPE: protein ( x i ) SEQUENCE DESCRIPTION: SEQ ID NO:12:

Val
 1

( 2 ) INFORMATION FOR SEQ ID NO:13:

( i ) SEQUENCE CHARACTERISTICS:
                ( A ) LENGTH: 103 base pairs
                ( B ) TYPE: nucleic acid
                ( C ) STRANDEDNESS: double
                ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Plasmid ( v i i ) IMMEDIATE SOURCE:
                ( B ) CLONE: 520-17.5 (Junction C)

( i x ) FEATURE:

(A) NAME/KEY: CDS
                (B) LOCATION: 1..72
                (C) IDENTIFICATION METHOD: experimental
                (D) OTHER INFORMATION: /partial
                        / codon_start= 1
                        / function= "marker enzyme"
                        / product= "Beta-galactosidase"
                        / evidence= EXPERIMENTAL
                        / gene= "lacZ"
                        / number= 1
                        / citation= ([1])

(ix) FEATURE:
                (A) NAME/KEY: CDS
                (B) LOCATION: 73..78
                (C) IDENTIFICATION METHOD: experimental
                (D) OTHER INFORMATION: /codon_start= 73
                        / function= "Translational finish of hybrid
                        protein"
                        / product= "C-terminal peptide"
                        / evidence= EXPERIMENTAL
                        / number= 2
                        / standard_name= "Translation of synthetic DNA
                        sequence"

(x) PUBLICATION INFORMATION:
                (A) AUTHORS: Ferrari, Franco A
                        Trach, Kathleen
                        Hoch, James A
                (B) TITLE: Seqquence Analysis of the spo0B Locus Reveals
                        a Polycistronic Transcription Unit
                (C) JOURNAL: J. Bacteriol.
                (D) VOLUME: 161
                (E) ISSUE: 2
                (F) PAGES: 556-562
                (G) DATE: Feb.-1985

(xi) SEQUENCE DESCRIPTION: SEQ ID NO:13:

```
AGC CCG TCA GTA TCG GCG GAA ATC CAG CTG AGC GCC GGT CGC TAC CAT      48
Ser Pro Ser Val Ser Ala Glu Ile Gln Leu Ser Ala Gly Arg Tyr His
 1           5                   10                  15

TAC CAG TTG GTC TGG TGT CAA AAA GAT CCA TAATTAATTA ACCCGGGTCG        98
Tyr Gln Leu Val Trp Cys Gln Lys Asp Pro
            20                       1

AAGAC                                                               103
```

(2) INFORMATION FOR SEQ ID NO:14:

(i) SEQUENCE CHARACTERISTICS:
                (A) LENGTH: 24 amino acids
                (B) TYPE: amino acid
                (D) TOPOLOGY: linear (ii) MOLECULE TYPE: protein (xi) SEQUENCE DESCRIPTION: SEQ ID NO:14:

```
Ser Pro Ser Val Ser Ala Glu Ile Gln Leu Ser Ala Gly Arg Tyr His
 1           5                   10                  15

Tyr Gln Leu Val Trp Cys Gln Lys
            20
```

(2) INFORMATION FOR SEQ ID NO:15:

(i) SEQUENCE CHARACTERISTICS:
                (A) LENGTH: 2 amino acids
                (B) TYPE: amino acid
                (D) TOPOLOGY: linear (ii) MOLECULE TYPE: protein (xi) SEQUENCE DESCRIPTION: SEQ ID NO:15:

Asp Pro (2) INFORMATION FOR SEQ ID NO:16:

(i) SEQUENCE CHARACTERISTICS:
        (A) LENGTH: 48 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmid (vii) IMMEDIATE SOURCE:
        (B) CLONE: 520-17.5 (Junction D)

(xi) SEQUENCE DESCRIPTION: SEQ ID NO:16:

```
AGATCCCCGG GCGAGCTCGA ATTCGTAATC ATGGTCATAG CTGTTTCC        48
```

(2) INFORMATION FOR SEQ ID NO:17:

(i) SEQUENCE CHARACTERISTICS:
        (A) LENGTH: 57 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmid (vii) IMMEDIATE SOURCE:
        (B) CLONE: 538-46.26 (Junction A)

(xi) SEQUENCE DESCRIPTION: SEQ ID NO:17:

```
CACATACGAT TTAGGTGACA CTATAGAATA CAAGCTTTAT ACCATTATAG ATACATT        57
```

(2) INFORMATION FOR SEQ ID NO:18:

(i) SEQUENCE CHARACTERISTICS:
        (A) LENGTH: 102 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmid (vii) IMMEDIATE SOURCE:
        (B) CLONE: 538-46.16 (Junction B)

(ix) FEATURE:
        (A) NAME/KEY: CDS
        (B) LOCATION: 91..102
        (C) IDENTIFICATION METHOD: experimental
        (D) OTHER INFORMATION: /partial
            / codon_start= 91
            / function= "marker enzyme"

-continued

```
                    / product= "Beta-Galactosidase"
                    / evidence= EXPERIMENTAL
                    / gene= "lacZ"
                    / number= 2
                    / citation= ([1])

( i x ) FEATURE:
               ( A ) NAME/KEY: CDS
               ( B ) LOCATION: 76..90
               ( D ) OTHER INFORMATION: /partial
                    / codon_start= 76
                    / function= "Translational start of hybrid protein"
                    / product= "N-terminal peptide"
                    / number= 1
                    / standard_name= "Translation of synthetic DNA
                    sequence"

( x ) PUBLICATION INFORMATION:
               ( A ) AUTHORS: Ferrari, Franco A
                              Trach, Kathleen
                              Hoch, James A
               ( B ) TITLE: Seqquence Analysis of the spo0B Locus Reveals
                            a Polycistronic Transcription Unit
               ( C ) JOURNAL: J. Bacteriol.
               ( D ) VOLUME: 161
               ( E ) ISSUE: 2
               ( F ) PAGES: 556-562
               ( G ) DATE: Feb.-1985

( x i ) SEQUENCE DESCRIPTION: SEQ ID NO:18:

AAGCTGGTAG   ATTTCCATGT   AGGGCCGCCT   GCAGGTCGAC   TCTAGAATTT   CATTTGTTT           60

TTTTCTATGC   TATAA  ATG  AAT  TCG  GAT  CCC  GTC  GTT  TTA  CAA                    102
                    Met  Asn  Ser  Asp  Pro  Val  Val  Leu  Gln
                     1                  5         1

( 2 ) INFORMATION FOR SEQ ID NO:19:

( i ) SEQUENCE CHARACTERISTICS:
               ( A ) LENGTH: 5 amino acids
               ( B ) TYPE: amino acid
               ( D ) TOPOLOGY: linear ( i i ) MOLECULE TYPE: protein ( x i ) SEQUENCE DESCRIPTION: SEQ ID NO:19:

Met  Asn  Ser  Asp  Pro
 1                   5

( 2 ) INFORMATION FOR SEQ ID NO:20:

( i ) SEQUENCE CHARACTERISTICS:
               ( A ) LENGTH: 4 amino acids
               ( B ) TYPE: amino acid
               ( D ) TOPOLOGY: linear ( i i ) MOLECULE TYPE: protein ( x i ) SEQUENCE DESCRIPTION: SEQ ID NO:20:

Val  Val  Leu  Gln
 1

( 2 ) INFORMATION FOR SEQ ID NO:21:

( i ) SEQUENCE CHARACTERISTICS:
               ( A ) LENGTH: 206 base pairs
               ( B ) TYPE: nucleic acid
               ( C ) STRANDEDNESS: double
               ( D ) TOPOLOGY: circular ( i i ) MOLECULE TYPE: DNA (genomic)

( i i i ) HYPOTHETICAL: NO
```

( i v ) ANTI-SENSE: NO ( v i ) ORIGINAL SOURCE:
    ( A ) ORGANISM: Plasmid ( v i i ) IMMEDIATE SOURCE:
    ( B ) CLONE: 538-46.16 (Junction C)

( i x ) FEATURE:
    ( A ) NAME/KEY: CDS
    ( B ) LOCATION: 1..63
    ( C ) IDENTIFICATION METHOD: experimental
    ( D ) OTHER INFORMATION: /partial
        / codon_start= 1
        / function= "marker enzyme"
        / product= "Beta-galactosidase"
        / evidence= EXPERIMENTAL
        / number= 1
        / citation= ([1])

( i x ) FEATURE:
    ( A ) NAME/KEY: CDS
    ( B ) LOCATION: 64..69
    ( C ) IDENTIFICATION METHOD: experimental
    ( D ) OTHER INFORMATION: /codon_start= 64
        / function= "Translational finish of hybrid protein"
        / product= "C-terminal peptide"
        / evidence= EXPERIMENTAL
        / standard_name= "Translation of synthetic DNA sequence"

( i x ) FEATURE:
    ( A ) NAME/KEY: CDS
    ( B ) LOCATION: 177..185
    ( C ) IDENTIFICATION METHOD: experimental
    ( D ) OTHER INFORMATION: /codon_start= 177
        / function= "Translational start of hybrid protein"
        / product= "N-terminal peptide"
        / evidence= EXPERIMENTAL
        / standard_name= "Translation of synthetic DNA sequence"

( i x ) FEATURE:
    ( A ) NAME/KEY: CDS
    ( B ) LOCATION: 186..206
    ( C ) IDENTIFICATION METHOD: experimental
    ( D ) OTHER INFORMATION: /partial
        / codon_start= 186
        / function= "glycoprotein"
        / product= "PRV gp50"
        / evidence= EXPERIMENTAL
        / gene= "gp50"
        / number= 3
        / citation= ([2])

( x ) PUBLICATION INFORMATION:
    ( A ) AUTHORS: Ferrari, Franco A
        Trach, Kathleen
        Hoch, James A
    ( B ) TITLE: Seqquence Analysis of the spo0B Locus Reveals a Polycistronic Transcription Unit
    ( C ) JOURNAL: J. Bacteriol.
    ( D ) VOLUME: 161
    ( E ) ISSUE: 2
    ( F ) PAGES: 556-562
    ( G ) DATE: Feb.-1985

( x ) PUBLICATION INFORMATION:
    ( A ) AUTHORS: Petrovskis, Erik A
        Timmins, James G
        Armentrout, Marty A
        Marchioli, Carmine C
        Jr. Yancy, Robert J
        Post, Leonard E
    ( B ) TITLE: DNA Sequence of the Gene for Pseudorabies Virus gp50, a Glycoprotein without N-Linked Glycosylation
    ( C ) JOURNAL: J. Virol.
    ( D ) VOLUME: 59

( E ) ISSUE: 2
( F ) PAGES: 216-223
( G ) DATE: Aug.-1986

( x i ) SEQUENCE DESCRIPTION: SEQ ID NO:21:

```
GTA  TCG  GCG  GAA  ATC  CAG  CTG  AGC  GCC  GGT  CGC  TAC  CAT  TAC  CAG  TTG          48
Val  Ser  Ala  Glu  Ile  Gln  Leu  Ser  Ala  Gly  Arg  Tyr  His  Tyr  Gln  Leu
 1              5                        10                       15

GTC  TGG  TGT  CAA  AAA  GAT  CCA  TAATTAATTA  ACCCGGCCGC  CTGCAGGTCG              99
Val  Trp  Cys  Gln  Lys  Asp  Pro
              20            1

ACTCTAGAAA  AAATTGAAAA  ACTATTCTAA  TTTATTGCAC  GGAGATCTTT  TTTTTTTTT              159

TTTTTTTTGG  CATATAA ATG  AAT  TCG  CTC  GCA  GCG  CTA  TTG  GCG  GCG                 206
                    Met  Asn  Ser  Leu  Ala  Ala  Leu  Leu  Ala  Ala
                     1              1                   5
```

( 2 ) INFORMATION FOR SEQ ID NO:22:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Val  Ser  Ala  Glu  Ile  Gln  Leu  Ser  Ala  Gly  Arg  Tyr  His  Tyr  Gln  Leu
 1              5                        10                       15
Val  Trp  Cys  Gln  Lys
              20
```

( 2 ) INFORMATION FOR SEQ ID NO:23:

( i ) SEQUENCE CHARACTERISTICS:
        ( A ) LENGTH: 2 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

Asp  Pro
 1

( 2 ) INFORMATION FOR SEQ ID NO:24:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

Met  Asn  Ser
 1

( 2 ) INFORMATION FOR SEQ ID NO:25:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

Leu Ala Ala Leu Leu Ala Ala
 1               5

(2) INFORMATION FOR SEQ ID NO:26:

(i) SEQUENCE CHARACTERISTICS:
        (A) LENGTH: 101 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmid (vii) IMMEDIATE SOURCE:
        (B) CLONE: 538-46.16 (Junction D)

(ix) FEATURE:
        (A) NAME/KEY: CDS
        (B) LOCATION: 1..15
        (D) OTHER INFORMATION: /partial
            / codon_start= 1
            / function= "glycoprotein"
            / product= "PRV gp63"
            / gene= "gp63"
            / number= 1
            / citation= ([1])

(x) PUBLICATION INFORMATION:
        (A) AUTHORS: Petrovskis, Erik A
                    Timmins, James G
                    Post, Lenoard E
        (B) TITLE: Use of Lambda-gt11 To Isolate Genes for two
             Pseudorabies Virus Glycoproteins with homology to
             Herpes Simplex Virus and Varicella-Zoster Virus
             Glycoproteins
        (C) JOURNAL: J. Virol.
        (D) VOLUME: 60
        (E) ISSUE: 1
        (F) PAGES: 185-193
        (G) DATE: Oct.-1986

(xi) SEQUENCE DESCRIPTION: SEQ ID NO:26:

```
CGC GTG CAC CAC GAG GGACTCTAGA GGATCCATAA TTAATTAATT AATTTTTATC         55
Arg Val His His Glu
 1               5
CCGGGTCGAC CTGCAGGCGG CCGGGTCGAC CTGCAGGCGG CCAGAC                     101
```

(2) INFORMATION FOR SEQ ID NO:27:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:27:

Arg Val His His Glu
 1               5

(2) INFORMATION FOR SEQ ID NO:28:

(i) SEQUENCE CHARACTERISTICS:
        (A) LENGTH: 57 base pairs
        (B) TYPE: nucleic acid
        (C) STRANDEDNESS: double
        (D) TOPOLOGY: circular (i i) MOLECULE TYPE: DNA (genomic)

(i i i) HYPOTHETICAL: NO (i v) ANTI-SENSE: NO (v i) ORIGINAL SOURCE:
 (A) ORGANISM: Plasmid (v i i) IMMEDIATE SOURCE:
 (B) CLONE: 538-46.16 (Junction E)

(x i) SEQUENCE DESCRIPTION: SEQ ID NO:28:

| AGATCCCCGG | GCGAGCTCGA | ATTCGTAATC | ATGGTCATAG | CTGTTTCCTG | TGTGAAA | 57 |

(2) INFORMATION FOR SEQ ID NO:29:

(i) SEQUENCE CHARACTERISTICS:
 (A) LENGTH: 1907 base pairs
 (B) TYPE: nucleic acid
 (C) STRANDEDNESS: double
 (D) TOPOLOGY: linear (i i) MOLECULE TYPE: cDNA to mRNA (i i i) HYPOTHETICAL: NO (i v) ANTI-SENSE: NO (v i) ORIGINAL SOURCE:
 (A) ORGANISM: Newcastle disease virus
 (B) STRAIN: B1

(v i i) IMMEDIATE SOURCE:
 (B) CLONE: 137-23.803 (PSY1142)

(v i i i) POSITION IN GENOME:
 (B) MAP POSITION: []50%
( C ) UNITS: %G ( i x ) FEATURE:
( A ) NAME/KEY: CDS
( B ) LOCATION: 92..1822
( D ) OTHER INFORMATION: /codon_start= 92
/ product= "NDV heamagglutinin-Neuraminidase"
/ gene= "HN"
/ number= 1

( x i ) SEQUENCE DESCRIPTION: SEQ ID NO:29:

```
ACGGGTAGAA CGGTAAGAGA GGCCGCCCCT CAATTGCGAG CCAGACTTCA CAACCTCCGT         60

TCTACCGCTT CACCGACAAC AGTCCTCAAT C ATG GAC CGC GCC GTT AGC CAA           112
                                   Met Asp Arg Ala Val Ser Gln
                                     1               5

GTT GCG TTA GAG AAT GAT GAA AGA GAG GCA AAA AAT ACA TGG CGC TTG          160
Val Ala Leu Glu Asn Asp Glu Arg Glu Ala Lys Asn Thr Trp Arg Leu
        10                  15                  20

ATA TTC CGG ATT GCA ATC TTA TTC TTA ACA GTA GTG ACC TTG GCT ATA          208
Ile Phe Arg Ile Ala Ile Leu Phe Leu Thr Val Val Thr Leu Ala Ile
    25                  30                  35

TCT GTA GCC TCC CTT TTA TAT AGC ATG GGG GCT AGC ACA CCT AGC GAT          256
Ser Val Ala Ser Leu Leu Tyr Ser Met Gly Ala Ser Thr Pro Ser Asp
 40                  45                  50                  55

CTT GTA GGC ATA CCG ACT AGG ATT TCC AGG GCA GAA GAA AAG ATT ACA          304
Leu Val Gly Ile Pro Thr Arg Ile Ser Arg Ala Glu Glu Lys Ile Thr
                 60                  65                  70

TCT ACA CTT GGT TCC AAT CAA GAT GTA GTA GAT AGG ATA TAT AAG CAA          352
Ser Thr Leu Gly Ser Asn Gln Asp Val Val Asp Arg Ile Tyr Lys Gln
            75                  80                  85

GTG GCC CTT GAG TCT CCA TTG GCA TTG TTA AAT ACT GAG ACC ACA ATT          400
```

-continued

```
                Val  Ala  Leu  Glu  Ser  Pro  Leu  Ala  Leu  Leu  Asn  Thr  Glu  Thr  Thr  Ile
                           90                       95                      100

ATG  AAC  GCA  ATA  ACA  TCT  CTC  TCT  TAT  CAG  ATT  AAT  GGA  GCT  GCA  AAC                          448
Met  Asn  Ala  Ile  Thr  Ser  Leu  Ser  Tyr  Gln  Ile  Asn  Gly  Ala  Ala  Asn
          105                      110                      115

AAC  AGC  GGG  TGG  GGG  GCA  CCT  ATT  CAT  GAC  CCA  GAT  TAT  ATA  GGG  GGG                          496
Asn  Ser  Gly  Trp  Gly  Ala  Pro  Ile  His  Asp  Pro  Asp  Tyr  Ile  Gly  Gly
120                      125                      130                      135

ATA  GGC  AAA  GAA  CTC  ATT  GTA  GAT  GAT  GCT  AGT  GAT  GTC  ACA  TCA  TTC                          544
Ile  Gly  Lys  Glu  Leu  Ile  Val  Asp  Asp  Ala  Ser  Asp  Val  Thr  Ser  Phe
                    140                      145                      150

TAT  CCC  TCT  GCA  TTT  CAA  GAA  CAT  CTG  AAT  TTT  ATC  CCG  GCG  CCT  ACT                          592
Tyr  Pro  Ser  Ala  Phe  Gln  Glu  His  Leu  Asn  Phe  Ile  Pro  Ala  Pro  Thr
               155                      160                      165

ACA  GGA  TCA  GGT  TGC  ACT  CGA  ATA  CCC  TCA  TTT  GAC  ATG  AGT  GCT  ACC                          640
Thr  Gly  Ser  Gly  Cys  Thr  Arg  Ile  Pro  Ser  Phe  Asp  Met  Ser  Ala  Thr
               170                      175                      180

CAT  TAC  TGC  TAC  ACC  CAT  AAT  GTA  ATA  TTG  TCT  GGA  TGC  AGA  GAT  CAC                          688
His  Tyr  Cys  Tyr  Thr  His  Asn  Val  Ile  Leu  Ser  Gly  Cys  Arg  Asp  His
          185                      190                      195

TCA  CAC  TCA  CAT  CAG  TAT  TTA  GCA  CTT  GGT  GTG  CTC  CGG  ACA  TCT  GCA                          736
Ser  His  Ser  His  Gln  Tyr  Leu  Ala  Leu  Gly  Val  Leu  Arg  Thr  Ser  Ala
200                      205                      210                      215

ACA  GGG  AGG  GTA  TTC  TTT  TCT  ACT  CTG  CGT  TCC  ATC  AAC  CTG  GAC  GAC                          784
Thr  Gly  Arg  Val  Phe  Phe  Ser  Thr  Leu  Arg  Ser  Ile  Asn  Leu  Asp  Asp
                    220                      225                      230

ACC  CAA  AAT  CGG  AAG  TCT  TGC  AGT  GTG  AGT  GCA  ACT  CCC  CTG  GGT  TGT                          832
Thr  Gln  Asn  Arg  Lys  Ser  Cys  Ser  Val  Ser  Ala  Thr  Pro  Leu  Gly  Cys
               235                      240                      245

GAT  ATG  CTG  TGC  TCG  AAA  GCC  ACG  GAG  ACA  GAG  GAA  GAA  GAT  TAT  AAC                          880
Asp  Met  Leu  Cys  Ser  Lys  Ala  Thr  Glu  Thr  Glu  Glu  Glu  Asp  Tyr  Asn
          250                      255                      260

TCA  GCT  GTC  CCT  ACG  CGG  ATG  GTA  CAT  GGG  AGG  TTA  GGG  TTC  GAC  GGC                          928
Ser  Ala  Val  Pro  Thr  Arg  Met  Val  His  Gly  Arg  Leu  Gly  Phe  Asp  Gly
          265                      270                      275

CAA  TAT  CAC  GAA  AAG  GAC  CTA  GAT  GTC  ACA  ACA  TTA  TTC  GGG  GAC  TGG                          976
Gln  Tyr  His  Glu  Lys  Asp  Leu  Asp  Val  Thr  Thr  Leu  Phe  Gly  Asp  Trp
280                      285                      290                      295

GTG  GCC  AAC  TAC  CCA  GGA  GTA  GGG  GGT  GGA  TCT  TTT  ATT  GAC  AGC  CGC                         1024
Val  Ala  Asn  Tyr  Pro  Gly  Val  Gly  Gly  Gly  Ser  Phe  Ile  Asp  Ser  Arg
                    300                      305                      310

GTG  TGG  TTC  TCA  GTC  TAC  GGA  GGG  TTA  AAA  CCC  AAT  ACA  CCC  AGT  GAC                         1072
Val  Trp  Phe  Ser  Val  Tyr  Gly  Gly  Leu  Lys  Pro  Asn  Thr  Pro  Ser  Asp
               315                      320                      325

ACT  GTA  CAG  GAA  GGG  AAA  TAT  GTG  ATA  TAC  AAG  CGA  TAC  AAT  GAC  ACA                         1120
Thr  Val  Gln  Glu  Gly  Lys  Tyr  Val  Ile  Tyr  Lys  Arg  Tyr  Asn  Asp  Thr
          330                      335                      340

TGC  CCA  GAT  GAG  CAA  GAC  TAC  CAG  ATT  CGA  ATG  GCC  AAG  TCT  TCG  TAT                         1168
Cys  Pro  Asp  Glu  Gln  Asp  Tyr  Gln  Ile  Arg  Met  Ala  Lys  Ser  Ser  Tyr
345                      350                      355

AAG  CCT  GGA  CGG  TTT  GGT  GGG  AAA  CGC  ATA  CAG  CAG  GCT  ATC  TTA  TCT                         1216
Lys  Pro  Gly  Arg  Phe  Gly  Gly  Lys  Arg  Ile  Gln  Gln  Ala  Ile  Leu  Ser
          360                      365                      370                      375

ATC  AAA  GTG  TCA  ACA  TCC  TTA  GGC  GAA  GAC  CCG  GTA  CTG  ACT  GTA  CCG                         1264
Ile  Lys  Val  Ser  Thr  Ser  Leu  Gly  Glu  Asp  Pro  Val  Leu  Thr  Val  Pro
                    380                      385                      390

CCC  AAC  ACA  GTC  ACA  CTC  ATG  GGG  GCC  GAA  GGC  AGA  ATT  CTC  ACA  GTA                         1312
Pro  Asn  Thr  Val  Thr  Leu  Met  Gly  Ala  Glu  Gly  Arg  Ile  Leu  Thr  Val
               395                      400                      405

GGG  ACA  TCC  CAT  TTC  TTG  TAT  CAG  CGA  GGG  TCA  TCA  TAC  TTC  TCT  CCC                         1360
```

|     |     |     |     |     |     |     |     |     |     |     |     |     |     |     |      |
| --- | --- | --- | --- | --- | --- | --- | --- | --- | --- | --- | --- | --- | --- | --- | ---- |
| Gly | Thr | Ser | His | Phe | Leu | Tyr | Gln | Arg | Gly | Ser | Ser | Tyr | Phe | Ser | Pro  |
|     |     | 410 |     |     |     |     | 415 |     |     |     |     | 420 |     |     |      |
| GCG | TTA | TTA | TAT | CCT | ATG | ACA | GTC | AGC | AAC | AAA | ACA | GCC | ACT | CTT | CAT  | 1408 |
| Ala | Leu | Leu | Tyr | Pro | Met | Thr | Val | Ser | Asn | Lys | Thr | Ala | Thr | Leu | His  |
|     | 425 |     |     |     |     | 430 |     |     |     |     | 435 |     |     |     |      |
| AGT | CCT | TAT | ACA | TTC | AAT | GCC | TTC | ACT | CGG | CCA | GGT | AGT | ATC | CCT | TGC  | 1456 |
| Ser | Pro | Tyr | Thr | Phe | Asn | Ala | Phe | Thr | Arg | Pro | Gly | Ser | Ile | Pro | Cys  |
| 440 |     |     |     |     | 445 |     |     |     |     | 450 |     |     |     |     | 455  |
| CAG | GCT | TCA | GCA | AGA | TGC | CCC | AAC | TCA | TGT | GTT | ACT | GGA | GTC | TAT | ACA  | 1504 |
| Gln | Ala | Ser | Ala | Arg | Cys | Pro | Asn | Ser | Cys | Val | Thr | Gly | Val | Tyr | Thr  |
|     |     |     |     | 460 |     |     |     |     | 465 |     |     |     |     | 470 |      |
| GAT | CCA | TAT | CCC | CTA | ATC | TTC | TAT | AGA | AAC | CAC | ACC | TTG | CGA | GGG | GTA  | 1552 |
| Asp | Pro | Tyr | Pro | Leu | Ile | Phe | Tyr | Arg | Asn | His | Thr | Leu | Arg | Gly | Val  |
|     |     |     | 475 |     |     |     |     | 480 |     |     |     |     | 485 |     |      |
| TTC | GGG | ACA | ATG | CTT | GAT | GGT | GAA | CAA | GCA | AGA | CTT | AAC | CCT | GCG | TCT  | 1600 |
| Phe | Gly | Thr | Met | Leu | Asp | Gly | Glu | Gln | Ala | Arg | Leu | Asn | Pro | Ala | Ser  |
|     |     | 490 |     |     |     |     | 495 |     |     |     |     | 500 |     |     |      |
| GCA | GTA | TTC | GAT | AGC | ACA | TCC | CGC | AGT | CGC | ATA | ACT | CGA | GTG | AGT | TCA  | 1648 |
| Ala | Val | Phe | Asp | Ser | Thr | Ser | Arg | Ser | Arg | Ile | Thr | Arg | Val | Ser | Ser  |
|     | 505 |     |     |     |     | 510 |     |     |     |     | 515 |     |     |     |      |
| AGC | AGC | ATC | AAA | GCA | GCA | TAC | ACA | ACA | TCA | ACT | TGT | TTT | AAA | GTG | GTC  | 1696 |
| Ser | Ser | Ile | Lys | Ala | Ala | Tyr | Thr | Thr | Ser | Thr | Cys | Phe | Lys | Val | Val  |
| 520 |     |     |     |     | 525 |     |     |     |     | 530 |     |     |     |     | 535  |
| AAG | ACC | AAT | AAG | ACC | TAT | TGT | CTC | AGC | ATT | GCT | GAA | ATA | TCT | AAT | ACT  | 1744 |
| Lys | Thr | Asn | Lys | Thr | Tyr | Cys | Leu | Ser | Ile | Ala | Glu | Ile | Ser | Asn | Thr  |
|     |     |     |     | 540 |     |     |     |     | 545 |     |     |     |     | 550 |      |
| CTC | TTC | GGA | GAA | TTC | AGA | ATC | GTC | CCG | TTA | CTA | GTT | GAG | ATC | CTC | AAA  | 1792 |
| Leu | Phe | Gly | Glu | Phe | Arg | Ile | Val | Pro | Leu | Leu | Val | Glu | Ile | Leu | Lys  |
|     |     | 555 |     |     |     |     | 560 |     |     |     |     | 565 |     |     |      |
| GAT | GAC | GGG | GTT | AGA | GAA | GCC | AGG | TCT | GGC | TAGTTGAGTC | | AACTATGAAA | | | | 1842 |
| Asp | Asp | Gly | Val | Arg | Glu | Ala | Arg | Ser | Gly |     |     |     |     |     |      |
|     |     | 570 |     |     |     |     | 575 |     |     |     |     |     |     |     |      |

GAGTTGGAAA GATGGCATTG TATCACCTAT CTTCTGCGAC ATCAAGAATC AAACCGAATG 1902

CCGGC 1907

(2) INFORMATION FOR SEQ ID NO:30:

(i) SEQUENCE CHARACTERISTICS:
        (A) LENGTH: 577 amino acids
        (B) TYPE: amino acid
        (D) TOPOLOGY: linear (ii) MOLECULE TYPE: protein (xi) SEQUENCE DESCRIPTION: SEQ ID NO:30:

|     |     |     |     |     |     |     |     |     |     |     |     |     |     |     |
| --- | --- | --- | --- | --- | --- | --- | --- | --- | --- | --- | --- | --- | --- | --- |
| Met | Asp | Arg | Ala | Val | Ser | Gln | Val | Ala | Leu | Glu | Asn | Asp | Glu | Arg | Glu |
| 1   |     |     |     | 5   |     |     |     |     | 10  |     |     |     |     | 15  |
| Ala | Lys | Asn | Thr | Trp | Arg | Leu | Ile | Phe | Arg | Ile | Ala | Ile | Leu | Phe | Leu |
|     |     |     | 20  |     |     |     |     | 25  |     |     |     |     | 30  |     |
| Thr | Val | Val | Thr | Leu | Ala | Ile | Ser | Val | Ala | Ser | Leu | Leu | Tyr | Ser | Met |
|     |     | 35  |     |     |     |     | 40  |     |     |     |     | 45  |     |     |
| Gly | Ala | Ser | Thr | Pro | Ser | Asp | Leu | Val | Gly | Ile | Pro | Thr | Arg | Ile | Ser |
|     | 50  |     |     |     |     | 55  |     |     |     |     | 60  |     |     |     |
| Arg | Ala | Glu | Glu | Lys | Ile | Thr | Ser | Thr | Leu | Gly | Ser | Asn | Gln | Asp | Val |
| 65  |     |     |     |     | 70  |     |     |     |     | 75  |     |     |     |     | 80  |
| Val | Asp | Arg | Ile | Tyr | Lys | Gln | Val | Ala | Leu | Glu | Ser | Pro | Leu | Ala | Leu |
|     |     |     |     | 85  |     |     |     |     | 90  |     |     |     |     | 95  |
| Leu | Asn | Thr | Glu | Thr | Thr | Ile | Met | Asn | Ala | Ile | Thr | Ser | Leu | Ser | Tyr |
|     |     |     | 100 |     |     |     |     | 105 |     |     |     |     | 110 |     |

```
Gln Ile Asn Gly Ala Ala Asn Asn Ser Gly Trp Gly Ala Pro Ile His
            115                 120                 125
Asp Pro Asp Tyr Ile Gly Gly Ile Gly Lys Glu Leu Ile Val Asp Asp
    130                 135                 140
Ala Ser Asp Val Thr Ser Phe Tyr Pro Ser Ala Phe Gln Glu His Leu
145                 150                 155                 160
Asn Phe Ile Pro Ala Pro Thr Thr Gly Ser Gly Cys Thr Arg Ile Pro
                165                 170                 175
Ser Phe Asp Met Ser Ala Thr His Tyr Cys Tyr Thr His Asn Val Ile
            180                 185                 190
Leu Ser Gly Cys Arg Asp His Ser His Ser His Gln Tyr Leu Ala Leu
        195                 200                 205
Gly Val Leu Arg Thr Ser Ala Thr Gly Arg Val Phe Phe Ser Thr Leu
    210                 215                 220
Arg Ser Ile Asn Leu Asp Asp Thr Gln Asn Arg Lys Ser Cys Ser Val
225                 230                 235                 240
Ser Ala Thr Pro Leu Gly Cys Asp Met Leu Cys Ser Lys Ala Thr Glu
                245                 250                 255
Thr Glu Glu Glu Asp Tyr Asn Ser Ala Val Pro Thr Arg Met Val His
            260                 265                 270
Gly Arg Leu Gly Phe Asp Gly Gln Tyr His Glu Lys Asp Leu Asp Val
        275                 280                 285
Thr Thr Leu Phe Gly Asp Trp Val Ala Asn Tyr Pro Gly Val Gly Gly
    290                 295                 300
Gly Ser Phe Ile Asp Ser Arg Val Trp Phe Ser Val Tyr Gly Gly Leu
305                 310                 315                 320
Lys Pro Asn Thr Pro Ser Asp Thr Val Gln Glu Gly Lys Tyr Val Ile
                325                 330                 335
Tyr Lys Arg Tyr Asn Asp Thr Cys Pro Asp Glu Gln Asp Tyr Gln Ile
            340                 345                 350
Arg Met Ala Lys Ser Ser Tyr Lys Pro Gly Arg Phe Gly Gly Lys Arg
        355                 360                 365
Ile Gln Gln Ala Ile Leu Ser Ile Lys Val Ser Thr Ser Leu Gly Glu
    370                 375                 380
Asp Pro Val Leu Thr Val Pro Pro Asn Thr Val Thr Leu Met Gly Ala
385                 390                 395                 400
Glu Gly Arg Ile Leu Thr Val Gly Thr Ser His Phe Leu Tyr Gln Arg
                405                 410                 415
Gly Ser Ser Tyr Phe Ser Pro Ala Leu Leu Tyr Pro Met Thr Val Ser
            420                 425                 430
Asn Lys Thr Ala Thr Leu His Ser Pro Tyr Thr Phe Asn Ala Phe Thr
        435                 440                 445
Arg Pro Gly Ser Ile Pro Cys Gln Ala Ser Ala Arg Cys Pro Asn Ser
    450                 455                 460
Cys Val Thr Gly Val Tyr Thr Asp Pro Tyr Pro Leu Ile Phe Tyr Arg
465                 470                 475                 480
Asn His Thr Leu Arg Gly Val Phe Gly Thr Met Leu Asp Gly Glu Gln
                485                 490                 495
Ala Arg Leu Asn Pro Ala Ser Ala Val Phe Asp Ser Thr Ser Arg Ser
            500                 505                 510
Arg Ile Thr Arg Val Ser Ser Ser Ile Lys Ala Ala Tyr Thr Thr
        515                 520                 525
Ser Thr Cys Phe Lys Val Val Lys Thr Asn Lys Thr Tyr Cys Leu Ser
    530                 535                 540
```

Ile Ala Glu Ile Ser Asn Thr Leu Phe Gly Glu Phe Arg Ile Val Pro
545                 550                 555                 560

Leu Leu Val Glu Ile Leu Lys Asp Asp Gly Val Arg Glu Ala Arg Ser
                565                 570                 575

Gly ( 2 ) INFORMATION FOR SEQ ID NO:31:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 538-46.26 (Junction A)

( x i ) SEQUENCE DESCRIPTION: SEQ ID NO:31:

CACATACGAT TTAGGTGACA CTATAGAATA CAAGCTTTAT ACCATTATAG ATACATT 57

( 2 ) INFORMATION FOR SEQ ID NO:32:

( i ) SEQUENCE CHARACTERISTICS:
        ( A ) LENGTH: 108 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 538-46.26 (Junction B)

( i x ) FEATURE:
        ( A ) NAME/KEY: exon
        ( B ) LOCATION: 88..102
        ( D ) OTHER INFORMATION: /codon_start= 88
            / function= "Translational start of hybrid protein"
            / product= "N-terminal peptide"
            / number= 1
            / standard_name= "Translation of synthetic DNA sequence"

( i x ) FEATURE:
        ( A ) NAME/KEY: CDS
        ( B ) LOCATION: 103..108
        ( C ) IDENTIFICATION METHOD: experimental
        ( D ) OTHER INFORMATION: /partial
            / codon_start= 103
            / product= "NDV Heamagglutinin-Neuraminidase"
            / evidence= EXPERIMENTAL
            / gene= "HN"

```
TTTTTTTTT TTTTTTTGG CATATAAATG AATTCGGATC CG GAC CGC                    108
                                              Asp Arg
                                               1
```

( 2 ) INFORMATION FOR SEQ ID NO:33:

( i ) SEQUENCE CHARACTERISTICS:
        ( A ) LENGTH: 2 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

```
Asp Arg
 1
```

( 2 ) INFORMATION FOR SEQ ID NO:34:

( i ) SEQUENCE CHARACTERISTICS:
        ( A ) LENGTH: 108 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 538-46.26 (Junction C)

( i x ) FEATURE:
        ( A ) NAME/KEY: CDS
        ( B ) LOCATION: 70..84
        ( D ) OTHER INFORMATION: /codon_start= 70
            / function= "Translational start of hybrid protein"
            / product= "N-terminal peptide"
            / number= 1
            / standard_name= "Translation of synthetic DNA sequence"

( i x ) FEATURE:
        ( A ) NAME/KEY: CDS
        ( B ) LOCATION: 85..108
        ( C ) IDENTIFICATION METHOD: experimental
        ( D ) OTHER INFORMATION: /partial
            / codon_start= 85
            / function= "marker enzyme"
            / product= "Beta-galactosidase"
            / evidence= EXPERIMENTAL
            / gene= "lacZ"
            / number= 2
            / citation= ([1])

( x ) PUBLICATION INFORMATION:
        ( A ) AUTHORS: Ferrari, Franco A
            Trach, Kathleen
            Hoch, James A
        ( B ) TITLE: Sequence Analysis of the spo0B Locus Reveals a Polycistronic Transcription Unit
        ( C ) JOURNAL: J. Bacteriol.
        ( D ) VOLUME: 161
        ( E ) ISSUE: 2
        ( F ) PAGES: 556-562
        ( G ) DATE: Feb.-1985

( x i ) SEQUENCE DESCRIPTION: SEQ ID NO:34:

```
TGCGACATCA AGAATCAAAC CGAATGCCCT CGACTCTAGA ATTTCATTTT GTTTTTTCT         60

ATGCTATAA ATG AAT TCG GAT CCC GTC GTT TTA CAA CGT CGT GAC TGG           108
```

```
     Met  Asn  Ser  Asp  Pro  Val  Val  Leu  Gln  Arg  Arg  Asp  Trp
      1              5    1              5
```

(2) INFORMATION FOR SEQ ID NO:35:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:35:

```
Met  Asn  Ser  Asp  Pro
 1                   5
```

(2) INFORMATION FOR SEQ ID NO:36:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO:36:

```
Val  Val  Leu  Gln  Arg  Arg  Asp  Trp
 1                   5
```

(2) INFORMATION FOR SEQ ID NO:37:

(i) SEQUENCE CHARACTERISTICS:
        (A) LENGTH: 108 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vi) ORIGINAL SOURCE:
        (A) ORGANISM: Plasmid (vii) IMMEDIATE SOURCE:
        (B) CLONE: 538-46.26

(ix) FEATURE:
        (A) NAME/KEY: CDS
        (B) LOCATION: 1..54
        (C) IDENTIFICATION METHOD: experimental
        (D) OTHER INFORMATION: /partial
            / codon_start= 1
            / function= "marker enzyme"
            / product= "Beta-galactosidase"
            / evidence= EXPERIMENTAL
            / gene= "lacZ"
            / number= 1
            / citation= ([1])

(ix) FEATURE:
        (A) NAME/KEY: CDS
        (B) LOCATION: 55..63
        (C) IDENTIFICATION METHOD: experimental
        (D) OTHER INFORMATION: /codon_start= 55
            / function= "Translational finish of hybrid
            protein"
            / product= "C-terminal peptide"
            / evidence= EXPERIMENTAL
            / number= 2
            / standard_name= "Translation of synthetic DNA
            sequence"

( x i ) SEQUENCE DESCRIPTION: SEQ ID NO:37:

| GAA | ATC | CAG | CTG | AGC | GCC | GGT | CGC | TAC | CAT | TAC | CAG | TTG | GTC | TGG | TGT | 48 |
| Glu | Ile | Gln | Leu | Ser | Ala | Gly | Arg | Tyr | His | Tyr | Gln | Leu | Val | Trp | Cys | |
| 1 | | | | 5 | | | | | 10 | | | | | 15 | | |

| CAA | AAA | GAT | CCA | TAATTAATTA | ACCCGGGTCG | AGGGTCGAAG | ACCAAATTCT | 100 |
| Gln | Lys | Asp | Pro | | | | | |
| | | | 1 | | | | | |

AACATGGT                                                                                                   108

( 2 ) INFORMATION FOR SEQ ID NO:38:

( i ) SEQUENCE CHARACTERISTICS:
        ( A ) LENGTH: 18 amino acids
        ( B ) TYPE: amino acid
        ( D ) TOPOLOGY: linear ( i i ) MOLECULE TYPE: protein ( x i ) SEQUENCE DESCRIPTION: SEQ ID NO:38:

| Glu | Ile | Gln | Leu | Ser | Ala | Gly | Arg | Tyr | His | Tyr | Gln | Leu | Val | Trp | Cys |
| 1 | | | | 5 | | | | | 10 | | | | | 15 | |

Gln Lys ( 2 ) INFORMATION FOR SEQ ID NO:39:

( i ) SEQUENCE CHARACTERISTICS:
        ( A ) LENGTH: 2 amino acids
        ( B ) TYPE: amino acid
        ( D ) TOPOLOGY: linear ( i i ) MOLECULE TYPE: protein ( x i ) SEQUENCE DESCRIPTION: SEQ ID NO:39:

Asp Pro
 1

( 2 ) INFORMATION FOR SEQ ID NO:40:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Plasmid ( v i i ) IMMEDIATE SOURCE:
        ( B ) CLONE: 538-46.26 (Junction E)

( x i ) SEQUENCE DESCRIPTION: SEQ ID NO:40:

AGATCCCCGG GCGAGCTCGA ATTCGTAATC ATGGTCATAG CTGTTTCCTG TGTGAAA                57

( 2 ) INFORMATION FOR SEQ ID NO:41:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( v i ) ORIGINAL SOURCE:
      ( A ) ORGANISM: Pseudorabies virus [ ]Synthetic oligonucleotide primer ( x i ) SEQUENCE DESCRIPTION: SEQ ID NO:41:

CGCGAATTCG CTCGCAGCGC TATTGGC 27

( 2 ) INFORMATION FOR SEQ ID NO:42:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: N ( i v ) ANTI-SENSE: N ( v i ) ORIGINAL SOURCE:
        ( A ) ORGANISM: Pseudorabies virus [ ]Synthetic oligonucleotide primer ( x i ) SEQUENCE DESCRIPTION: SEQ ID NO:42:

GTAGGAGTGG CTGCTGAAG 19

( 2 ) INFORMATION FOR SEQ ID NO:43:

( i ) SEQUENCE CHARACTERISTICS:
        ( A ) LENGTH: 70 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Swinepox virus
        ( B ) STRAIN: Kasza
        ( C ) INDIVIDUAL ISOLATE: S-SPV- 001

( v i i ) IMMEDIATE SOURCE:
        ( B ) CLONE: 515-85.1

( v i i i ) POSITION IN GENOME:
        ( B ) MAP POSITION: []23.2
        ( C ) UNITS: %G ( x i ) SEQUENCE DESCRIPTION: SEQ ID NO:43:

AAAAATTGAA AAACTATTCT AATTTATTGC ACGGAGATCT TTTTTTTTTT TTTTTTTTG 60

GCATATAAAT 70

( 2 ) INFORMATION FOR SEQ ID NO:44:

( i ) SEQUENCE CHARACTERISTICS:
        ( A ) LENGTH: 74 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Swinepox virus
    ( B ) STRAIN: Kasza
    ( C ) INDIVIDUAL ISOLATE: S-SPV- 001

( v i i ) IMMEDIATE SOURCE:
    ( B ) CLONE: 515-85.1

( v i i i ) POSITION IN GENOME:
    ( B ) MAP POSITION: []23.2
    ( C ) UNITS: %G ( x i ) SEQUENCE DESCRIPTION: SEQ ID NO:44:

```
TTTTTTTTT  TTTTTTTTT  GGCATATAAA  TAGATCTGTA  TCCTAAAATT  GAATTGTAAT          60

TATCGATAAT  AAAT                                                              74
```

( 2 ) INFORMATION FOR SEQ ID NO:45:

( i ) SEQUENCE CHARACTERISTICS:
        ( A ) LENGTH: 37 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Swinepox virus
        ( B ) STRAIN: Kasza
        ( C ) INDIVIDUAL ISOLATE: S-SPV- 001

( v i i ) IMMEDIATE SOURCE:
        ( B ) CLONE: 515-85.1

( v i i i ) POSITION IN GENOME:
        ( B ) MAP POSITION: []23.2
        ( C ) UNITS: %G ( x i ) SEQUENCE DESCRIPTION: SEQ ID NO:45:

```
GTATCCTAAA  ATTGAATTGT  AATTATCGAT  AATAAAT                                   37
```

( 2 ) INFORMATION FOR SEQ ID NO:46:

( i ) SEQUENCE CHARACTERISTICS:
        ( A ) LENGTH: 41 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Swinepox virus
        ( B ) STRAIN: Kasza
        ( C ) INDIVIDUAL ISOLATE: S-SPV- 001

( v i i ) IMMEDIATE SOURCE:
        ( B ) CLONE: 515-85.1

( v i i i ) POSITION IN GENOME:
        ( B ) MAP POSITION: []23.2
        ( C ) UNITS: %G ( x i ) SEQUENCE DESCRIPTION: SEQ ID NO:46:

```
CGACTCTAGA ATTTCATTTT GTTTTTTTCT ATGCTATAAA T                                    4 1
```

( 2 ) INFORMATION FOR SEQ ID NO:47:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Swinepox virus
        ( B ) STRAIN: Kasza
        ( C ) INDIVIDUAL ISOLATE: S-SPV- 001

( v i i ) IMMEDIATE SOURCE:
        ( B ) CLONE: 515-85.1

( v i i i ) POSITION IN GENOME:
        ( B ) MAP POSITION: []23.2
        ( C ) UNITS: %G ( x i ) SEQUENCE DESCRIPTION: SEQ ID NO:47:

```
CACATACGAT TTAGGTGACA CTATAGAATA CAAGCTTTGA GTCTATTGGT TATTTATACG                60
```

( 2 ) INFORMATION FOR SEQ ID NO:48:

( i ) SEQUENCE CHARACTERISTICS:
        ( A ) LENGTH: 123 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Swinepox virus
        ( B ) STRAIN: Kasza
        ( C ) INDIVIDUAL ISOLATE: S-SPV- 001

( v i i ) IMMEDIATE SOURCE:
        ( B ) CLONE: 515-85.1

( v i i i ) POSITION IN GENOME:
        ( B ) MAP POSITION: []23.2
        ( C ) UNITS: %G ( i x ) FEATURE:
        ( A ) NAME/KEY: CDS
        ( B ) LOCATION: 100..123

( x i ) SEQUENCE DESCRIPTION: SEQ ID NO:48:

```
TGAATATATA GCAAATAAAG GAAAAATTGT TATCGTTGCT GCATTAGATG GAACATAGGT                 60

CGACTCTAGA ATTTCATTTT GTTTTTTTCT ATGCTATAA ATG AAT TCG GAT CCC                   114
                                           Met Asn Ser Asp Pro
                                            1               5

GTC GTT TTA                                                                      123
Val Val Leu
```

( 2 ) INFORMATION FOR SEQ ID NO:49:

( i ) SEQUENCE CHARACTERISTICS:

(A) LENGTH: 8 amino acids
(B) TYPE: amino acid
(D) TOPOLOGY: linear (ii) MOLECULE TYPE: protein (xi) SEQUENCE DESCRIPTION: SEQ ID NO:49:

Met Asn Ser Asp Pro Val Val Leu
1               5

(2) INFORMATION FOR SEQ ID NO:50:

(i) SEQUENCE CHARACTERISTICS:
(A) LENGTH: 132 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Swinepox virus
(B) STRAIN: Kasza
(C) INDIVIDUAL ISOLATE: S-SPV-001

(vii) IMMEDIATE SOURCE:
(B) CLONE: 515-85.1

(viii) POSITION IN GENOME:
(B) MAP POSITION: []23.2
(C) UNITS: %G (ix) FEATURE:
(A) NAME/KEY: CDS
(B) LOCATION: 1..63

(xi) SEQUENCE DESCRIPTION: SEQ ID NO:50:

```
GAA ATC CAG CTG AGC GCC GGT CGC TAC CAT TAC CAG TTG GTC TGG TGT           48
Glu Ile Gln Leu Ser Ala Gly Arg Tyr His Tyr Gln Leu Val Trp Cys
 1               5                  10                  15

CAA AAA GAT CCA TAATTAATTA ACCCGGGTCG ACCTATGAAC GTAAACCATT              100
Gln Lys Asp Pro
             20

TGGTAATATT CTTAATCTTA TACCATTATC GG                                      132
```

(2) INFORMATION FOR SEQ ID NO:51:

(i) SEQUENCE CHARACTERISTICS:
(A) LENGTH: 20 amino acids
(B) TYPE: amino acid
(D) TOPOLOGY: linear (ii) MOLECULE TYPE: protein (xi) SEQUENCE DESCRIPTION: SEQ ID NO:51:

Glu Ile Gln Leu Ser Ala Gly Arg Tyr His Tyr Gln Leu Val Trp Cys
1               5                  10                  15
Gln Lys Asp Pro
             20

(2) INFORMATION FOR SEQ ID NO:52:

(i) SEQUENCE CHARACTERISTICS:
(A) LENGTH: 66 base pairs
(B) TYPE: nucleic acid
(C) STRANDEDNESS: double
(D) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Swinepox virus
                ( B ) STRAIN: Kasza
                ( C ) INDIVIDUAL ISOLATE: S-SPV- 001

( v i i ) IMMEDIATE SOURCE:
                ( B ) CLONE: 515-85.1

( v i i i ) POSITION IN GENOME:
                ( B ) MAP POSITION: []23.2
                ( C ) UNITS: %G ( x i ) SEQUENCE DESCRIPTION: SEQ ID NO:52:

TCTACTATTG TATATATAGG ATCCCCGGGC GAGCTCGAAT TCGTAATCAT GGTCATAGCT            60

GTTTCC            66

( 2 ) INFORMATION FOR SEQ ID NO:53:

( i ) SEQUENCE CHARACTERISTICS:
                ( A ) LENGTH: 51 base pairs
                ( B ) TYPE: nucleic acid
                ( C ) STRANDEDNESS: double
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Swinepox virus
                ( B ) STRAIN: Kasza
                ( C ) INDIVIDUAL ISOLATE: S-SPV- 001

( v i i ) IMMEDIATE SOURCE:
                ( B ) CLONE: 515-85.1

( v i i i ) POSITION IN GENOME:
                ( B ) MAP POSITION: []23.2
                ( C ) UNITS: %G ( x i ) SEQUENCE DESCRIPTION: SEQ ID NO:53:

ACAGGAAACA GCTATGACCA TGATTACGAA TTCGAGCTCG CCCGGGGATC T            51

( 2 ) INFORMATION FOR SEQ ID NO:54:

( i ) SEQUENCE CHARACTERISTICS:
                ( A ) LENGTH: 104 base pairs
                ( B ) TYPE: nucleic acid
                ( C ) STRANDEDNESS: double
                ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Swinepox virus
                ( B ) STRAIN: Kasza
                ( C ) INDIVIDUAL ISOLATE: S-SPV- 001

( v i i ) IMMEDIATE SOURCE:
                ( B ) CLONE: 515-85.1

( v i i i ) POSITION IN GENOME:

(B) MAP POSITION: []23.2
(C) UNITS: %G (ix) FEATURE:
(A) NAME/KEY: CDS
(B) LOCATION: 81..104

(x ( 2 ) INFORMATION FOR SEQ ID NO:57:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( x i ) SEQUENCE DESCRIPTION: SEQ ID NO:57:

```
Glu  Ile  Gln  Leu  Ser  Ala  Gly  Arg  Tyr  His  Tyr  Gln  Leu  Val  Trp  Cys
 1                  5                        10                       15
Gln  Lys  Asp  Pro
                20
```

( 2 ) INFORMATION FOR SEQ ID NO:58:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:58:

```
Met  Asn  Ser  Gly  Met  Ala  Ser
 1                  5
```

( 2 ) INFORMATION FOR SEQ ID NO:59:

( i ) SEQUENCE CHARACTERISTICS:
        ( A ) LENGTH: 109 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Swinepox virus
        ( B ) STRAIN: Kasza
        ( C ) INDIVIDUAL ISOLATE: S-SPV- 001

( v i i ) IMMEDIATE SOURCE:
        ( B ) CLONE: 515-85.1

( v i i i ) POSITION IN GENOME:
        ( B ) MAP POSITION: []23.2
        ( C ) UNITS: %G ( x i ) SEQUENCE DESCRIPTION: SEQ ID NO:59:

```
CCATGCTCTA  GAGGATCCCC  GGGCGAGCTC  GAATTCGGAT  CCATAATTAA  TTAATTAATT      60
TTTATCCCGG  GTCGACCGGG  TCGACCTGCA  GCCTACATGG  AAATCTACC                  109
```

( 2 ) INFORMATION FOR SEQ ID NO:60:

( i ) SEQUENCE CHARACTERISTICS:
        ( A ) LENGTH: 51 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO (v i) ORIGINAL SOURCE:
    (A) ORGANISM: Swinepox virus
    (B) STRAIN: Kasza
    (C) INDIVIDUAL ISOLATE: S-SPV- 001

(v i i) IMMEDIATE SOURCE:
    (B) CLONE: 515-85.1

(v i i i) POSITION IN GENOME:
    (B) MAP POSITION: []23.2
    (C) UNITS: %G (x i) SEQUENCE DESCRIPTION: SEQ ID NO:60:

TAATGTATCT ATAATGGTAT AAAGCTTGTA TTCTATAGTG TCACCTAAAT C    51

(2) INFORMATION FOR SEQ ID NO:61:

(i) SEQUENCE CHARACTERISTICS:
    (A) LENGTH: 51 base pairs
    (B) TYPE: nucleic acid
    (C) STRANDEDNESS: double
    (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
    (A) ORGANISM: Swinepox virus
    (B) STRAIN: Kasza
    (C) INDIVIDUAL ISOLATE: S-SPV- 001

(v i i) IMMEDIATE SOURCE:
    (B) CLONE: 515-85.1

(v i i i) POSITION IN GENOME:
    (B) MAP POSITION: []23.2
    (C) UNITS: %G (x i) SEQUENCE DESCRIPTION: SEQ ID NO:61:

ACAGGAAACA GCTATGACCA TGATTACGAA TTCGAGCTCG CCCGGGGATC T    51

(2) INFORMATION FOR SEQ ID NO:62:

(i) SEQUENCE CHARACTERISTICS:
    (A) LENGTH: 104 base pairs
    (B) TYPE: nucleic acid
    (C) STRANDEDNESS: double
    (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
    (A) ORGANISM: Swinepox virus
    (B) STRAIN: Kasza
    (C) INDIVIDUAL ISOLATE: S-SPV- 001

(v i i) IMMEDIATE SOURCE:
    (B) CLONE: 515-85.1

(v i i i) POSITION IN GENOME:
    (B) MAP POSITION: []23.2
    (C) UNITS: %G (i x) FEATURE:
    (A) NAME/KEY: CDS
    (B) LOCATION: 81..104

(x i) SEQUENCE DESCRIPTION: SEQ ID NO:62:

| | |
|---|---|
| AAATATATAA ATACCATGTT AGAATTTGGT CTGCTGCAGG TCGACTCTAG AATTTCATTT | 60 |

```
TGTTTTTTTC TATGCTATAA ATG AAT TCG GAT CCC GTC GTT TTA                    104
                      Met Asn Ser Asp Pro Val Val Leu
                      1               5
```

( 2 ) INFORMATION FOR SEQ ID NO:63:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( x i ) SEQUENCE DESCRIPTION: SEQ ID NO:63:

```
Met Asn Ser Asp Pro Val Val Leu
1               5
```

( 2 ) INFORMATION FOR SEQ ID NO:64:

( i ) SEQUENCE CHARACTERISTICS:
        ( A ) LENGTH: 182 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Swinepox virus
        ( B ) STRAIN: Kasza
        ( C ) INDIVIDUAL ISOLATE: S-SPV- 001

( v i i ) IMMEDIATE SOURCE:
        ( B ) CLONE: 515-85.1

( v i i i ) POSITION IN GENOME:
        ( B ) MAP POSITION: []23.2
        ( C ) UNITS: %G ( i x ) FEATURE:
        ( A ) NAME/KEY: CDS
        ( B ) LOCATION: 1..63

( i x ) FEATURE:
        ( A ) NAME/KEY: CDS
        ( B ) LOCATION: 156..182

( x i ) SEQUENCE DESCRIPTION: SEQ ID NO:64:

```
GAA ATC CAG CTG AGC GCC GGT CGC TAC CAT TAC CAG TTG GTC TGG TGT          48
Glu Ile Gln Leu Ser Ala Gly Arg Tyr His Tyr Gln Leu Val Trp Cys
1               5                   10                  15

CAA AAA GAT CCA TAATTAATTA ACCCGGTCGA CTCTAGAAAA AATTGAAAAA              100
Gln Lys Asp Pro
            20

CTATTCTAAT TTATTGCACG GAGATCTTTT TTTTTTTTT TTTTTGGCA TATAA ATG           158
                                                             Met
                                                             1

AAT TCC GGC ATG GCC TCG CTC GCG                                          182
Asn Ser Gly Met Ala Ser Leu Ala
            5
```

( 2 ) INFORMATION FOR SEQ ID NO:65:

( i ) SEQUENCE CHARACTERISTICS:
        ( A ) LENGTH: 20 amino acids
        ( B ) TYPE: amino acid (D) TOPOLOGY: linear (ii) MOLECULE TYPE: protein (xi) SEQUENCE DESCRIPTION: SEQ ID NO:65:

Glu Ile Gln Leu Ser Ala Gly Arg Tyr His Tyr Gln Leu Val Trp Cys
1               5                   10                      15

Gln Lys Asp Pro
            20

(2) INFORMATION FOR SEQ ID NO:66:

(i) SEQUENCE CHARACTERISTICS:
    (A) LENGTH: 9 amino acids
    (B) TYPE: amino acid
    (D) TOPOLOGY: linear (ii) MOLECULE TYPE: protein (xi) SEQUENCE DESCRIPTION: SEQ ID NO:66:

Met Asn Ser Gly Met Ala Ser Leu Ala
1               5

(2) INFORMATION FOR SEQ ID NO:67:

(i) SEQUENCE CHARACTERISTICS:
    (A) LENGTH: 109 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Swinepox virus
    (B) STRAIN: Kasza
    (C) INDIVIDUAL ISOLATE: S-SPV- 001

(vii) IMMEDIATE SOURCE:
    (B) CLONE: 515-85.1

(viii) POSITION IN GENOME:
    (B) MAP POSITION: []23.2
    (C) UNITS: %G (xi) SEQUENCE DESCRIPTION: SEQ ID NO:67:

CCATGCTCTA GAGGATCCCC GGGCGAGCTC GAATTCGGAT CCATAATTAA TTAATTAATT    60

TTTATCCCGG GTCGACCGGG TCGACCTGCA GCCTACATGG AAATCTACC              109

(2) INFORMATION FOR SEQ ID NO:68:

(i) SEQUENCE CHARACTERISTICS:
    (A) LENGTH: 51 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Swinepox virus
    (B) STRAIN: Kasza
    (C) INDIVIDUAL ISOLATE: S-SPV- 001

(v i i) IMMEDIATE SOURCE:
  (B) CLONE: 515-85.1

(v i i i) POSITION IN GENOME:
  (B) MAP POSITION: []23.2
  (C) UNITS: %G (x i) SEQUENCE DESCRIPTION: SEQ ID NO:68:

TAATGTATCT ATAATGGTAT AAAGCTTGTA TTCTATAGTG TCACCTAAAT C    51

(2) INFORMATION FOR SEQ ID NO:69:

(i) SEQUENCE CHARACTERISTICS:
    (A) LENGTH: 51 base pairs
    (B) TYPE: nucleic acid
    (C) STRANDEDNESS: double
    (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
    (A) ORGANISM: Swinepox virus
    (B) STRAIN: Kasza
    (C) INDIVIDUAL ISOLATE: S-SPV- 001

(v i i) IMMEDIATE SOURCE:
    (B) CLONE: 515-85.1

(v i i i) POSITION IN GENOME:
  (B) MAP POSITION: []23.2
  (C) UNITS: %G (x i) SEQUENCE DESCRIPTION: SEQ ID NO:69:

ACAGGAAACA GCTATGACCA TGATTACGAA TTCGAGCTCG CCCGGGGATC T    51

(2) INFORMATION FOR SEQ ID NO:70:

(i) SEQUENCE CHARACTERISTICS:
    (A) LENGTH: 104 base pairs
    (B) TYPE: nucleic acid
    (C) STRANDEDNESS: double
    (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
    (A) ORGANISM: Swinepox virus
    (B) STRAIN: Kasza
    (C) INDIVIDUAL ISOLATE: S-SPV- 001

(v i i) IMMEDIATE SOURCE:
    (B) CLONE: 515-85.1

(v i i i) POSITION IN GENOME:
  (B) MAP POSITION: []23.2
  (C) UNITS: %G (i x) FEATURE:
    (A) NAME/KEY: CDS
    (B) LOCATION: 81..104

(x i) SEQUENCE DESCRIPTION: SEQ ID NO:70:

AAATATATAA ATACCATGTT AGAATTTGGT CTGCTGCAGG TCGACTCTAG AATTTCATTT    60

TGTTTTTTTC TATGCTATAA ATG AAT TCG GAT CCC GTC GTT TTA    104
                     Met Asn Ser Asp Pro Val Val Leu
                      1               5

( 2 ) INFORMATION FOR SEQ ID NO:71:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( x i ) SEQUENCE DESCRIPTION: SEQ ID NO:71:

```
Met  Asn  Ser  Asp  Pro  Val  Val  Leu
 1                    5
```

( 2 ) INFORMATION FOR SEQ ID NO:72:

( i ) SEQUENCE CHARACTERISTICS:
        ( A ) LENGTH: 180 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Swinepox virus
        ( B ) STRAIN: Kasza
        ( C ) INDIVIDUAL ISOLATE: S-SPV- 001

( v i i ) IMMEDIATE SOURCE:
        ( B ) CLONE: 515-85.1

( v i i i ) POSITION IN GENOME

```
            1                   5                   10                  15
Gln Lys Asp Pro
            20
```

( 2 ) INFORMATION FOR SEQ ID NO:74:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO:74:

```
Met Asn Ser Gly Met Ala Ser
 1               5
```

( 2 ) INFORMATION FOR SEQ ID NO:75:

( i ) SEQUENCE CHARACTERISTICS:
        ( A ) LENGTH: 109 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Swinepox virus
        ( B ) STRAIN: Kasza
        ( C ) INDIVIDUAL ISOLATE: S-SPV- 001

( v i i ) IMMEDIATE SOURCE:
        ( B ) CLONE: 515-85.1

( v i i i ) POSITION IN GENOME:
        ( B ) MAP POSITION: []23.2
        ( C ) UNITS: %G ( x i ) SEQUENCE DESCRIPTION: SEQ ID NO:75:

```
CCATGCTCTA GAGGATCCCC GGGCGAGCTC GAATTCGGAT CCATAATTAA TTAATTAATT        60

TTTATCCCGG GTCGACCGGG TCGACCTGCA GCCTACATGG AAATCTACC                  109
```

( 2 ) INFORMATION FOR SEQ ID NO:76:

( i ) SEQUENCE CHARACTERISTICS:
        ( A ) LENGTH: 51 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Swinepox virus
        ( B ) STRAIN: Kasza
        ( C ) INDIVIDUAL ISOLATE: S-SPV- 001

( v i i ) IMMEDIATE SOURCE:
        ( B ) CLONE: 515-85.1

( v i i i ) POSITION IN GENOME:
        ( B ) MAP POSITION: []23.2
        ( C ) UNITS: %G (x i) SEQUENCE DESCRIPTION: SEQ ID NO:76:

TAATGTATCT ATAATGGTAT AAAGCTTGTA TTCTATAGTG TCACCTAAAT C  51

(2) INFORMATION FOR SEQ ID NO:77:

(i) SEQUENCE CHARACTERISTICS:
        (A) LENGTH: 51 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
        (A) ORGANISM: Swinepox virus
        (B) STRAIN: Kasza
        (C) INDIVIDUAL ISOLATE: S-SPV- 001

(v i i) IMMEDIATE SOURCE:
        (B) CLONE: 515-85.1

(v i i i) POSITION IN GENOME:
        (B) MAP POSITION: []23.2
&

(D) TOPOLOGY: linear (ii) MOLECULE TYPE: protein (xi) SEQUENCE DESCRIPTION: SEQ ID NO:79:

Met Asn Ser Gly Phe Ser Asn Ile
1               5

(2) INFORMATION FOR SEQ ID NO:80:

(i) SEQUENCE CHARACTERISTICS:
        (A) LENGTH: 126 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV- 001

(vii) IMMEDIATE SOURCE:
        (B) CLONE: 515-85.1

(iv) ANTI-SENSE: NO (vi) ORIGINAL SOURCE:
  (A) ORGANISM: Swinepox virus
  (B) STRAIN: Kasza
  (C) INDIVIDUAL ISOLATE: S-SPV-001

(vii) IMMEDIATE SOURCE:
  (B) CLONE: 515-85.1

(viii) POSITION IN GENOME:
  (B) MAP POSITION: []23.2
  (C) UNITS: %G (ix) FEATURE:
  (A) NAME/KEY: CDS
  (B) LOCATION: 1..63

(xi) SEQUENCE DESCRIPTION: SEQ ID NO:82:

| GAA | ATC | CAG | CTG | AGC | GCC | GGT | CGC | TAC | CAT | TAC | CAG | TTG | GTC | TGG | TGT | 48 |
| Glu | Ile | Gln | Leu | Ser | Ala | Gly | Arg | Tyr | His | Tyr | Gln | Leu | Val | Trp | Cys | |
| 1 | | | | 5 | | | | | 10 | | | | | 15 | | |

| CAA | AAA | GAT | CCA | TAATTAATTA | ACCCGGGTCG | ACCTGCAG | 88 |
| Gln | Lys | Asp | Pro | | | | |
| | | | 20 | | | | |

(2) INFORMATION FOR SEQ ID NO:83:

(i) SEQUENCE CHARACTERISTICS:
    (A) LENGTH: 20 amino acids
    (B) TYPE: amino acid
    (D) TOPOLOGY: linear (ii) MOLECULE TYPE: protein (xi) SEQUENCE DESCRIPTION: SEQ ID NO:83:

| Glu | Ile | Gln | Leu | Ser | Ala | Gly | Arg | Tyr | His | Tyr | Gln | Leu | Val | Trp | Cys |
| 1 | | | | 5 | | | | | 10 | | | | | 15 | |

| Gln | Lys | Asp | Pro |
| | | | 20 |

(2) INFORMATION FOR SEQ ID NO:84:

(i) SEQUENCE CHARACTERISTICS:
    (A) LENGTH: 51 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Swinepox virus
    (B) STRAIN: Kasza
    (C) INDIVIDUAL ISOLATE: S-SPV-001

(vii) IMMEDIATE SOURCE:
    (B) CLONE: 515-85.1

(viii) POSITION IN GENOME:
    (B) MAP POSITION: []23.2
    (C) UNITS: %G (xi) SEQUENCE DESCRIPTION: SEQ ID NO:84:

TAATGTATCT ATAATGGTAT AAAGCTTGTA TTCTATAGTG TCACCTAAAT C    51

(2) INFORMATION FOR SEQ ID NO:85:

(i) SEQUENCE CHARACTERISTICS:
    (A) LENGTH: 51 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Swinepox virus
    (B) STRAIN: Kasza
    (C) INDIVIDUAL ISOLATE: S-SPV-001

(vii) IMMEDIATE SOURCE:
    (B) CLONE: 515-85.1

(viii) POSITION IN GENOME:
    (B) MAP POSITION: []23.2
    (C) UNITS: %G (xi) SEQUENCE DESCRIPTION: SEQ ID NO:85:

```
ACAGGAAACA GCTATGACCA TGATTACGAA TTCGAGCTCG CCCGGGGATC T                51
```

(2) INFORMATION FOR SEQ ID NO:86:

(i) SEQUENCE CHARACTERISTICS:
    (A) LENGTH: 119 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Swinepox virus
    (B) STRAIN: Kasza
    (C) INDIVIDUAL ISOLATE: S-SPV-001

(vii) IMMEDIATE SOURCE:
    (B) CLONE: 515-85.1

(viii) POSITION IN GENOME:
    (B) MAP POSITION: []23.2
    (C) UNITS: %G (ix) FEATURE:
    (A) NAME/KEY: CDS
    (B) LOCATION: 99..119

(xi) SEQUENCE DESCRIPTION: SEQ ID NO:86:

```
GCGGCCGCCT GCAGGTCGAC TCTAGATTTT TTTTTTTTT TTTTTGGCA TATAAATAGA         60

TCTGTATCCT AAAATTGAAT TGTAATTATC GATAATAA ATG AAT TCG CTA CTT          113
                                          Met Asn Ser Leu Leu
                                           1               5

GGA ACT                                                                 119
Gly Thr
```

(2) INFORMATION FOR SEQ ID NO:87:

(i) SEQUENCE CHARACTERISTICS:
    (A) LENGTH: 7 amino acids
    (B) TYPE: amino acid
    (D) TOPOLOGY: linear (ii) MOLECULE TYPE: protein ( x i ) SEQUENCE DESCRIPTION: SEQ ID NO:87:

Met Asn Ser Leu Leu Gly Thr
1               5

( 2 ) INFORMATION FOR SEQ ID NO:88:

( i ) SEQUENCE CHARACTERISTICS:
        ( A ) LENGTH: 126 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Swinepox virus
        ( B ) STRAIN: Kasza
        ( C ) INDIVIDUAL ISOLATE: S-SPV- 001

( v i i ) IMMEDIATE SOURCE:
        ( B ) CLONE: 515-85.1

( v i i i ) POSITION IN GENOME:
        ( B ) MAP POSITION: []23.2
        ( C ) UNITS: %G ( i x ) FEATURE:
        ( A ) NAME/KEY: CDS
        ( B ) LOCATION: 1..12

( i x ) FEATURE:
        ( A ) NAME/KEY: CDS
        ( B ) LOCATION: 103..126

( x i ) SEQUENCE DESCRIPTION: SEQ ID NO:88:

```
ATA AAA ATG TGATTAAGTC TGAATGTGGA TCCATAATTA ATTAATTTTT           49
Ile Lys Met
1

ATCCCGGCGC GCCTCGACTC TAGAATTTCA TTTTGTTTTT TTCTATGCTA TAA ATG   105
                                                             Met
                                                             1

AAT TCG GAT CCC GTC GTT TTA                                      126
Asn Ser Asp Pro Val Val Leu
            5
```

( 2 ) INFORMATION FOR SEQ ID NO:89:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: protein ( x i ) SEQUENCE DESCRIPTION: SEQ ID NO:89:

Ile Lys Met
1

( 2 ) INFORMATION FOR SEQ ID NO:90:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( x i ) SEQUENCE DESCRIPTION: SEQ ID NO:90:

```
Met  Asn  Ser  Asp  Pro  Val  Val  Leu
  1                  5
```

( 2 ) INFORMATION FOR SEQ ID NO:91:

( i ) SEQUENCE CHARACTERISTICS:
        ( A ) LENGTH: 111 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Swinepox virus
        ( B ) STRAIN: Kasza
        ( C ) INDIVIDUAL ISOLATE: S-SPV- 001

( v i i ) IMMEDIATE SOURCE:
        ( B ) CLONE: 515-85.1

( v i i i ) POSITION IN GENOME:
        ( B ) MAP POSITION: []23.2
        ( C ) UNITS: %G ( i x ) FEATURE:
        ( A ) NAME/KEY: CDS
        ( B ) LOCATION: 1..63

( x i ) SEQUENCE DESCRIPTION: SEQ ID NO:91:

```
GAA  ATC  CAG  CTG  AGC  GCC  GGT  CGC  TAC  CAT  TAC  CAG  TTG  GTC  TGG  TGT         48
Glu  Ile  Gln  Leu  Ser  Ala  Gly  Arg  Tyr  His  Tyr  Gln  Leu  Val  Trp  Cys
  1                   5                        10                        15

CAA  AAA  GAT  CCA  TAATTAATTA  ACCCGGGTCG  AGGCGCGCCG  GGTCGACCTG                    100
Gln  Lys  Asp  Pro
                20

CAGGCGGCCG  C                                                                         111
```

( 2 ) INFORMATION FOR SEQ ID NO:92:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( x i ) SEQUENCE DESCRIPTION: SEQ ID NO:92:

```
Glu  Ile  Gln  Leu  Ser  Ala  Gly  Arg  Tyr  His  Tyr  Gln  Leu  Val  Trp  Cys
  1                   5                        10                        15

Gln  Lys  Asp  Pro
                20
```

( 2 ) INFORMATION FOR SEQ ID NO:93:

( i ) SEQUENCE CHARACTERISTICS:
        ( A ) LENGTH: 51 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Swinepox virus
( B ) STRAIN: Kasza
( C ) INDIVIDUAL ISOLATE: S-SPV- 001

( v i i ) IMMEDIATE SOURCE:
( B ) CLONE: 515-85.1

( v i i i ) POSITION IN GENOME:
( B ) MAP POSITION: []23.2
( C ) UNITS: %G ( x i ) SEQUENCE DESCRIPTION: SEQ ID NO:93:

TAATGTATCT ATAATGGTAT AAAGCTTGTA TTCTATAGTG TCACCTAAAT C        51

( 2 ) INFORMATION FOR SEQ ID NO:94:

( i ) SEQUENCE CHARACTERISTICS:
( A ) LENGTH: 51 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Swinepox virus
( B ) STRAIN: Kasza
( C ) INDIVIDUAL ISOLATE: S-SPV- 001

( v i i ) IMMEDIATE SOURCE:
( B ) CLONE: 515-85.1

( v i i i ) POSITION IN GENOME:
( B ) MAP POSITION: []23.2
( C ) UNITS: %G ( x i ) SEQUENCE DESCRIPTION: SEQ ID NO:94:

ACAGGAAACA GCTATGACCA TGATTACGAA TTCGAGCTCG CCCGGGGATC T        51

( 2 ) INFORMATION FOR SEQ ID NO:95:

( i ) SEQUENCE CHARACTERISTICS:
( A ) LENGTH: 119 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Swinepox virus
( B ) STRAIN: Kasza
( C ) INDIVIDUAL ISOLATE: S-SPV- 001

( v i i ) IMMEDIATE SOURCE:
( B ) CLONE: 515-85.1

( v i i i ) POSITION IN GENOME:
( B ) MAP POSITION: []23.2
( C ) UNITS: %G ( i x ) FEATURE:
( A ) NAME/KEY: CDS
( B ) LOCATION: 99..119

( x i ) SEQUENCE DESCRIPTION: SEQ ID NO:95:

|  |  |  |  |  |  |  |
|---|---|---|---|---|---|---|
| GCGGCCGCCT | GCAGGTCGAC | TCTAGATTTT | TTTTTTTTT | TTTTTGGCA | TATAAATAGA | 60 |

TCTGTATCCT AAAATTGAAT TGTAATTATC GATAATAA ATG AAT TCC CCT GCC 113
                                                                        Met Asn Ser Pro Ala
                                                                          1                              5

GCC CGG                                                                                                                                        119
Ala Arg (2) INFORMATION FOR SEQ ID NO:96:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:96:

Met Asn Ser Pro Ala Ala Arg
 1                 5

(2) INFORMATION FOR SEQ ID NO:97:

(i) SEQUENCE CHARACTERISTICS:
        (A) LENGTH: 126 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Swinepox virus
        (B) STRAIN: Kasza
        (C) INDIVIDUAL ISOLATE: S-SPV-001

(vii) IMMEDIATE SOURCE:
        (B) CLONE: 515-85.1

(viii) POSITION IN GENOME:
        (B) MAP POSITION: []23.2
  &

( i i ) MOLECULE TYPE: protein ( x i ) SEQUENCE DESCRIPTION: SEQ ID NO:98:

```
Leu  Gln  Glu  Pro  Ala  Arg  Leu  Glu  Arg  Asp  Pro
 1              5                        10
```

( 2 ) INFORMATION FOR SEQ ID NO:99:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: protein ( x i ) SEQUENCE DESCRIPTION: SEQ ID NO:99:

```
Met  Asn  Ser  Asp  Pro  Val  Val  Leu
 1              5
```

( 2 ) INFORMATION FOR SEQ ID NO:100:

( i ) SEQUENCE CHARACTERISTICS:
        ( A ) LENGTH: 111 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Swinepox virus
        ( B ) STRAIN: Kasza
        ( C ) INDIVIDUAL ISOLATE: S-SPV- 001

( v i i ) IMMEDIATE SOURCE:
        ( B ) CLONE: 515-85.1

( v i i i ) POSITION IN GENOME:
        ( B ) MAP POSITION: []23.2
        ( C ) UNITS: %G ( i x ) FEATURE:
        ( A ) NAME/KEY: CDS
        ( B ) LOCATION: 1..63

( x i ) SEQUENCE DESCRIPTION: SEQ ID NO:100:

```
GAA  ATC  CAG  CTG  AGC  GCC  GGT  CGC  TAC  CAT  TAC  CAG  TTG  GTC  TGG  TGT         48
Glu  Ile  Gln  Leu  Ser  Ala  Gly  Arg  Tyr  His  Tyr  Gln  Leu  Val  Trp  Cys
 1              5                        10                       15

CAA  AAA  GAT  CCA  TAATTAATTA  ACCCGGGTCG  AGGCGCGCCG  GGTCGACCTG                      100
Gln  Lys  Asp  Pro
                20

CAGGCGGCCG  C                                                                          111
```

( 2 ) INFORMATION FOR SEQ ID NO:101:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: protein ( x i ) SEQUENCE DESCRIPTION: SEQ ID NO:101:

```
Glu  Ile  Gln  Leu  Ser  Ala  Gly  Arg  Tyr  His  Tyr  Gln  Leu  Val  Trp  Cys
 1              5                        10                       15
```

Gln Lys Asp Pro
        20

( 2 ) INFORMATION FOR SEQ ID NO:102:

( i ) SEQUENCE CHARACTERISTICS:
        ( A ) LENGTH: 51 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Swinepox virus
        ( B ) STRAIN: Kasza
        ( C ) INDIVIDUAL ISOLATE: S-SPV- 001

( v i i ) IMMEDIATE SOURCE:
        ( B ) CLONE: 515-85.1

( v i i i ) POSITION IN GENOME:
        ( B ) MAP POSITION: []23.2
        ( C ) UNITS: %G ( x i ) SEQUENCE DESCRIPTION: SEQ ID NO:102:

TAATGTATCT ATAATGGTAT AAAGCTTGTA TTCTATAGTG TCACCTAAAT C     51

( 2 ) INFORMATION FOR SEQ ID NO:103:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Swinepox virus
        ( B ) STRAIN: Kasza
        ( C ) INDIVIDUAL ISOLATE: S-SPV- 001

( v i i ) IMMEDIATE SOURCE:
        ( B ) CLONE: 515-85.1

( v i i i ) POSITION IN GENOME:
        ( B ) MAP POSITION: []23.2
        ( C ) UNITS: %G ( x i ) SEQUENCE DESCRIPTION: SEQ ID NO:103:

CCGAATTCCG GCTTCAGTAA CATAGGATCG     30

( 2 ) INFORMATION FOR SEQ ID NO:104:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO (v i) ORIGINAL SOURCE:
    (A) ORGANISM: Swinepox virus
    (B) STRAIN: Kasza
    (C) INDIVIDUAL ISOLATE: S-SPV- 001

(v i i) IMMEDIATE SOURCE:
    (B) CLONE: 515-85.1

(v i i i) POSITION IN GENOME:
    (B) MAP POSITION: []23.2
    (C) UNITS: %G (x i) SEQUENCE DESCRIPTION: SEQ ID NO:104:

GTACCCATAC TGGTCGTGGC                                                           20

(2) INFORMATION FOR SEQ ID NO:105:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
        (A) ORGANISM: Swinepox virus
        (B) STRAIN: Kasza
        (C) INDIVIDUAL ISOLATE: S-SPV- 001

(v i i) IMMEDIATE SOURCE:
        (B) CLONE: 515-85.1

(v i i i) POSITION IN GENOME:
        (B) MAP POSITION: []23.2
        (C) UNITS: %G (x i) SEQUENCE DESCRIPTION: SEQ ID NO:105:

CCGGAATTCG CTACTTGGAA CTCTGG                                                    26

(2) INFORMATION FOR SEQ ID NO:106:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
        (A) ORGANISM: Swinepox virus
        (B) STRAIN: Kasza
        (C) INDIVIDUAL ISOLATE: S-SPV- 001

(v i i) IMMEDIATE SOURCE:
        (B) CLONE: 515-85.1

(v i i i) POSITION IN GENOME:
        (B) MAP POSITION: []23.2
        (C) UNITS: %G (x i) SEQUENCE DESCRIPTION: SEQ ID NO:106:

CATTGTCCCG AGACGGACAG                                                           20

( 2 ) INFORMATION FOR SEQ ID NO:107:

( i ) SEQUENCE CHARACTERISTICS:
        ( A ) LENGTH: 19 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Swinepox virus
        ( B ) STRAIN: Kasza
        ( C ) INDIVIDUAL ISOLATE: S-SPV- 001

( v i i ) IMMEDIATE SOURCE:
        ( B ) CLONE: 515-85.1

( v i i i ) POSITION IN GENOME:
        ( B ) MAP POSITION: []23.2
        ( C ) UNITS: %G ( x i ) SEQUENCE DESCRIPTION: SEQ ID NO:107:

CGCGATCCAA CTATCGGTG        19

( 2 ) INFORMATION FOR SEQ ID NO:108:

( i ) SEQUENCE CHARACTERISTICS:
        ( A ) LENGTH: 26 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Swinepox virus
        ( B ) STRAIN: Kasza
        ( C ) INDIVIDUAL ISOLATE: S-SPV- 001

( v i i ) IMMEDIATE SOURCE:
        ( B ) CLONE: 515-85.1

( v i i i ) POSITION IN GENOME:
        ( B ) MAP POSITION: []23.2
        ( C ) UNITS: %G ( x i ) SEQUENCE DESCRIPTION: SEQ ID NO:108:

GCGGATCCAC ATTCAGACTT AATCAC        26

( 2 ) INFORMATION FOR SEQ ID NO:109:

( i ) SEQUENCE CHARACTERISTICS:
        ( A ) LENGTH: 30 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Swinepox virus
        ( B ) STRAIN: Kasza
        ( C ) INDIVIDUAL ISOLATE: S-SPV- 001

(v i i) IMMEDIATE SOURCE:
    (B) CLONE: 515-85.1

(v i i i) POSITION IN GENOME:
    (B) MAP POSITION: []23.2
    (C) UNITS: %G (x i) SEQUENCE DESCRIPTION: SEQ ID NO:109:

ATGAATTCCC CTGCCGCCCG GACCGGCACC                                    30

(2) INFORMATION FOR SEQ ID NO:110:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
        (A) ORGANISM: Swinepox virus
        (B) STRAIN: Kasza
        (C) INDIVIDUAL ISOLATE: S-SPV- 001

(v i i) IMMEDIATE SOURCE:
        (B) CLONE: 515-85.1

(v i i i) POSITION IN GENOME:
        (B) MAP POSITION: []23.2
        (C) UNITS: %G (x i) SEQUENCE DESCRIPTION: SEQ ID NO:110:

CATGGATCCC GCTCGAGGCG AGCGGGCTCC                                    30

(2) INFORMATION FOR SEQ ID NO:111:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
        (A) ORGANISM: Swinepox virus
        (B) STRAIN: Kasza
        (C) INDIVIDUAL ISOLATE: S-SPV- 001

(v i i) IMMEDIATE SOURCE:
        (B) CLONE: 515-85.1

(v i i i) POSITION IN GENOME:
        (B) MAP POSITION: []23.2
        (C) UNITS: %G (x i) SEQUENCE DESCRIPTION: SEQ ID NO:111:

CTGGTTCGGC CCAGAATTCT ATGGGTCTCG CGCGGCTCGT GG                      42

(2) INFORMATION FOR SEQ ID NO:112:

(i) SEQUENCE CHARACTERISTICS:
        (A) LENGTH: 42 base pairs
        (B) TYPE: nucleic acid

```
            ( C ) STRANDEDNESS: double
            ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
            ( A ) ORGANISM: Swinepox virus
            ( B ) STRAIN: Kasza
            ( C ) INDIVIDUAL ISOLATE: S-SPV- 001

( v i i ) IMMEDIATE SOURCE:
            ( B ) CLONE: 515-85.1

( v i i i ) POSITION IN GENOME:
            ( B ) MAP POSITION: []23.2
            ( C ) UNITS: %G ( x i ) SEQUENCE DESCRIPTION: SEQ ID NO:112:

CTCGCTCGCC  CAGGATCCCT  AGCGGAGGAT  GGACTTGAGT  CG                                    4 2
```